US008828335B2

(12) United States Patent
Prakash et al.

(10) Patent No.: US 8,828,335 B2
(45) Date of Patent: Sep. 9, 2014

(54) MICROFLUIDIC BUBBLE LOGIC DEVICES

(71) Applicants: Manu Prakash, Cambridge, MA (US);
Neil Gershenfeld, Somerville, MA (US)

(72) Inventors: Manu Prakash, Cambridge, MA (US);
Neil Gershenfeld, Somerville, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 27 days.

(21) Appl. No.: 13/778,103

(22) Filed: Feb. 26, 2013

(65) Prior Publication Data

US 2013/0167958 A1 Jul. 4, 2013

Related U.S. Application Data

(60) Division of application No. 13/079,774, filed on Apr. 4, 2011, now Pat. No. 8,383,061, which is a division of application No. 12/028,776, filed on Feb. 8, 2008, now Pat. No. 7,918,244, and a continuation-in-part of application No. 11/416,449, filed on May 2, 2006, now Pat. No. 7,784,495.

(60) Provisional application No. 60/900,301, filed on Feb. 8, 2007, provisional application No. 60/676,910, filed on May 2, 2005.

(51) Int. Cl.
*G01N 15/06* (2006.01)
*G01N 33/00* (2006.01)
*G01N 33/48* (2006.01)
*G01N 15/14* (2006.01)

(52) U.S. Cl.
USPC .......... 422/503; 422/68.1; 422/502; 422/504; 422/81; 422/82; 436/43; 436/174; 436/179; 436/180

(58) Field of Classification Search
CPC .............. G01N 15/14; G01N 15/1425; G01N 15/1434; G01N 15/1463; G01N 15/147; G01N 15/1475; G01N 15/1484; B01L 3/5027; B01L 3/502707; B01L 3/502715; B01L 3/502776
USPC ................... 422/68.1, 502, 503, 504, 81, 82; 436/43, 174, 179, 180
See application file for complete search history.

(56) References Cited

U.S. PATENT DOCUMENTS

| 2005/0092662 | A1* | 5/2005 | Gilbert et al. | 210/97 |
| 2008/0236669 | A1* | 10/2008 | Unger et al. | 137/2 |
| 2009/0071541 | A1* | 3/2009 | Gilbert et al. | 137/2 |
| 2009/0151422 | A1* | 6/2009 | Unger et al. | 73/1.16 |

* cited by examiner

*Primary Examiner* — Brian J Sines
(74) *Attorney, Agent, or Firm* — Norma E. Henderson

(57) ABSTRACT

Fluid-based no-moving part logic devices are constructed from complex sequences of micro- and nanofluidic channels, on-demand bubble/droplet modulators and generators for programming the devices, and micro- and nanofluidic droplet/bubble memory elements for storage and retrieval of biological or chemical elements. The input sequence of bubbles/droplets encodes information, with the output being another sequence of bubbles/droplets or on-chip chemical synthesis. For performing a set of reactions/tasks or process control, the modulators can be used to program the device by producing a precisely timed sequence of bubbles/droplets, resulting in a cascade of logic operations within the micro- or nanofluidic channel sequence, utilizing the generated droplets/bubbles as a control. The devices are based on the principle of minimum energy interfaces formed between the two fluid phases enclosed inside precise channel geometries. Various devices, including logic gates, non-volatile bistable memory, ring oscillators, bubble synchronizers, analysis chips, and printers have been designed.

20 Claims, 46 Drawing Sheets

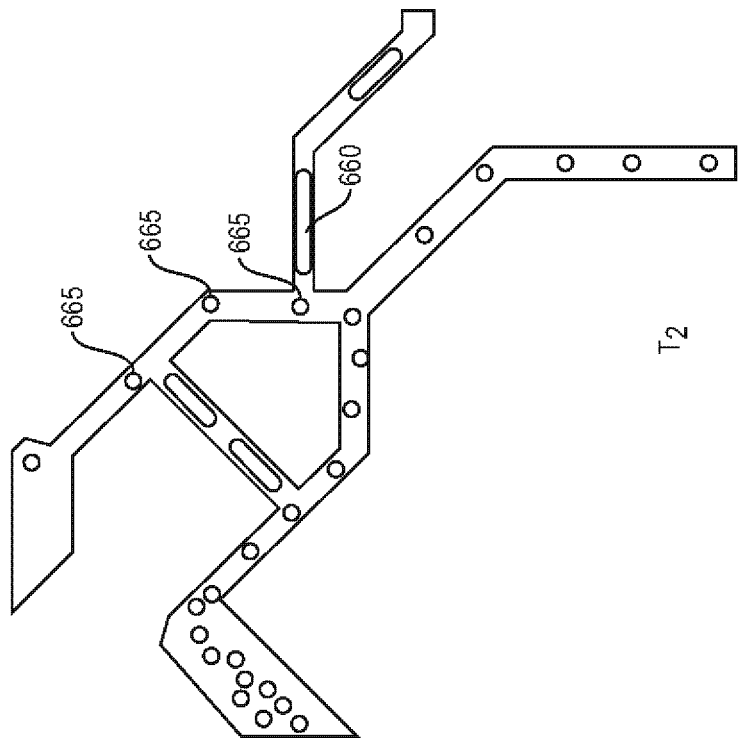
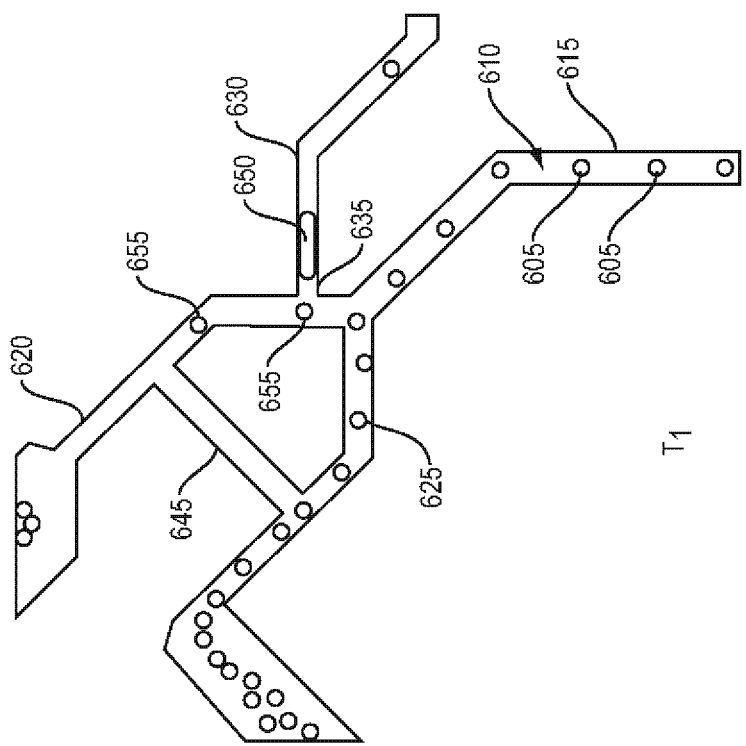
FIG. 6A
FIG. 6B

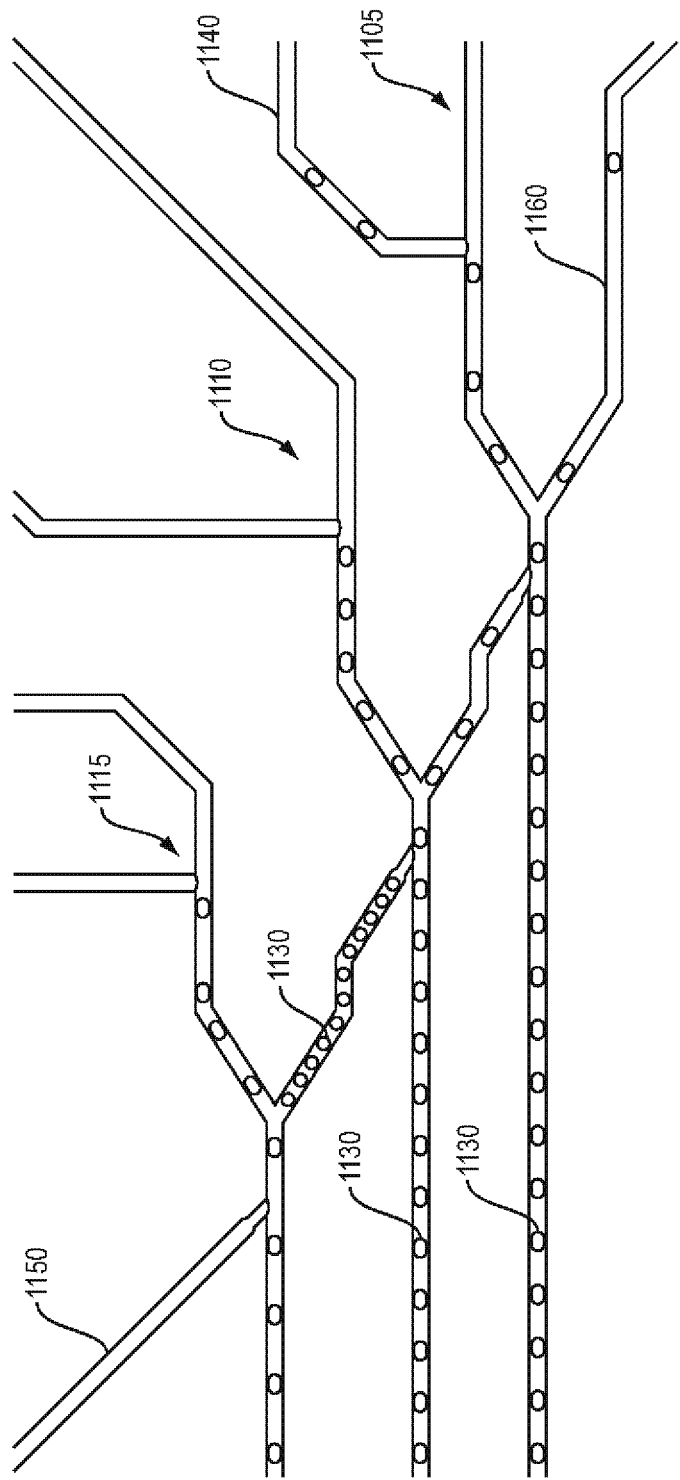

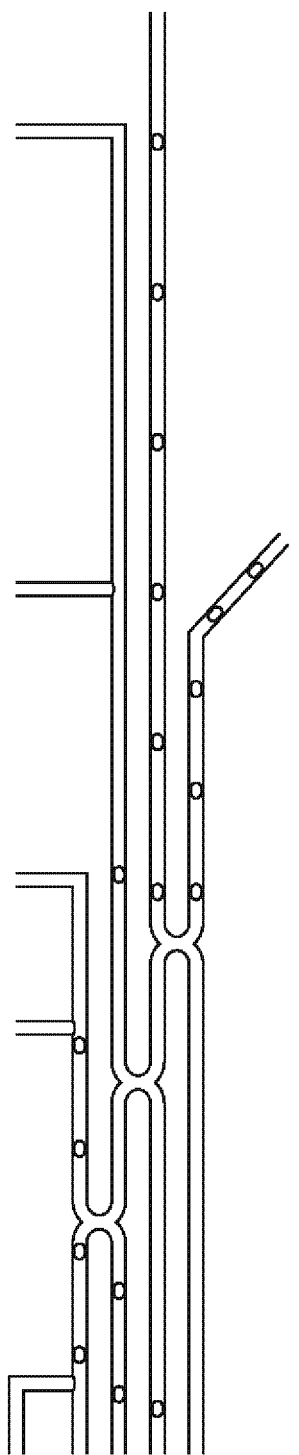

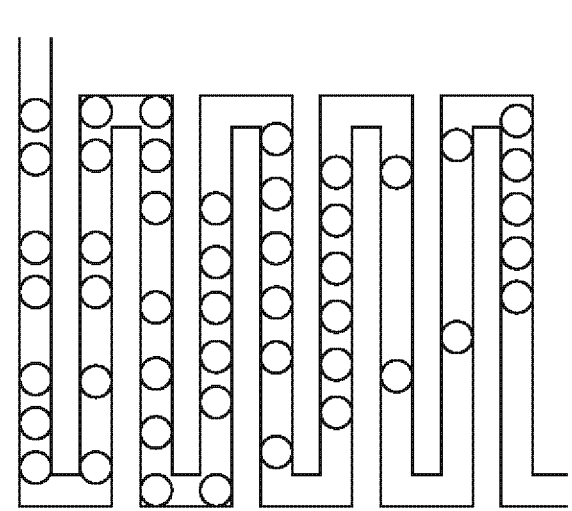
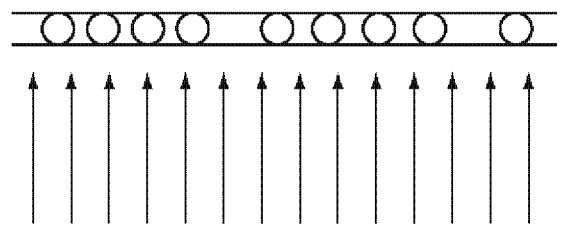
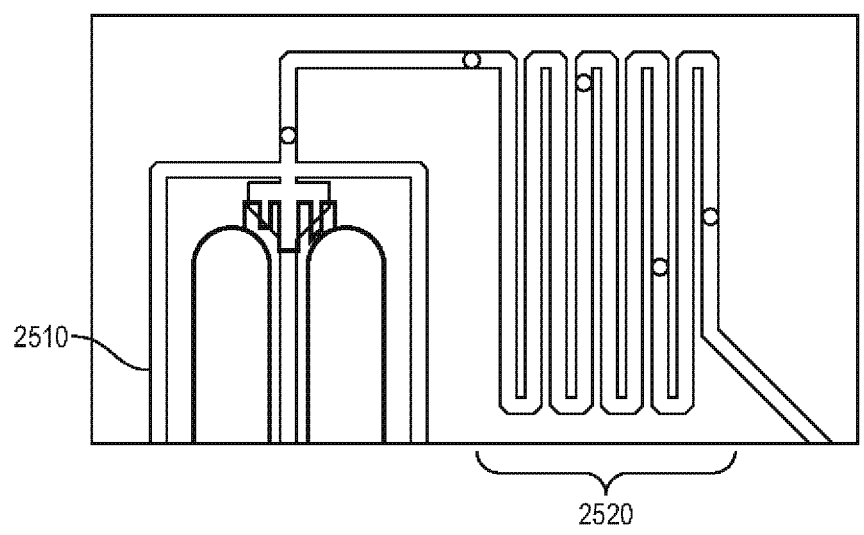
FIG. 25

MICROFLUIDIC BUBBLE LOGIC DEVICES

RELATED APPLICATIONS

This application is a divisional application of U.S. patent application Ser. No. 13/079,774, filed Apr. 4, 2011, now U.S. Pat. No. 8,383,061, issued Feb. 26, 2013, the entire disclosure of which is herein incorporated by reference, which is a divisional application of U.S. patent application Ser. No. 12/028,776, filed Feb. 8, 2008, now U.S. Pat. No. 7,918,244, issued Apr. 5, 2011, the entire disclosure of which is herein incorporated by reference, which claims the benefit of U.S. Provisional Application Ser. No. 60/900,301, filed Feb. 8, 2007, the entire disclosure of which is herein incorporated by reference.

This application is a continuation-in-part of U.S. patent application Ser. No. 11/416,449, filed May 2, 2006, now U.S. Pat. No. 7,784,495, issued Aug. 31, 2010, the entire disclosure of which is herein incorporated by reference, which claims the benefit of U.S. Provisional Application Ser. No. 60/676,910, filed May 2, 2005, the entire disclosure of which is herein incorporated by reference.

STATEMENT REGARDING FEDERALLY SPONSORED RESEARCH OR DEVELOPMENT

This invention was made with U.S. government support under Grant Number NSF CCR-0122419, awarded by the National Science Foundation. The government has certain rights in this invention.

FIELD OF THE TECHNOLOGY

The present invention relates to micromechanical logic circuits and, in particular, to fluidic logic devices employing multi-phase Newtonian fluid dynamic systems.

BACKGROUND

Fluidics was a competing technology to solid-state electronics in the 1960's and 1970's [Belsterling, Charles A., *Fluidic System Design,* 1971, Wiley Interscience; Conway, Arthur, *A Guide to Fluidics,* 1972, MacDonald and Co.]. Device physics for these fluidic devices was based primarily on inertial effects in fluid-like jet interaction, working on the basis of inertial forces present at larger (~1 cm) scales (higher Reynolds number). Several large-scale all-fluidic control systems were demonstrated during that time. Such fluidic gates were used to build a trajectory controller, an all-fluidic display, non-destructive memory and a simple computer. Because viscous and surface tension forces dominate fluid dynamics at small scales, these devices could not be miniaturized further, resulting in limitations in large-scale integration. With miniaturization, which was necessary for higher operating speeds and integration, it was impossible to maintain high Reynolds number flow in microscopic geometries. Fluidic approaches to control and logic applications were therefore eventually abandoned due to the inherent disadvantage that they could not be scaled down below millimeter scale because of their dependence on inertial effects. Furthermore, fluidic technology in the 1960's primarily used analog representations. This did not provide the state restoration benefits obtained with digital logic.

Various researchers have tried to exactly scale down the inertial effect devices using silicon micromachining [Zemel, Jay N., "Behaviour of microfluidic amplifiers, *Sensors and Actuators,* 1996]. As expected, the performance of these inertial effect devices falls down sharply with smaller length scales. High pressure and fluid flow velocity can be employed to improve upon performance, but this approach is not feasible if good performance for fluidic devices is required at reasonable pressure differentials.

Scalable control of droplet based microfluidic systems is one route to integrated mass-processing units at miniature length scales. Currently used external electronic control schemes use large arrays of electrodes, such as in electrowetting-based microfluidic droplet systems, thus limiting scaling properties of the devices. Moreover, electric field can cause unwanted interference effects on biomolecules. The problem is further complicated by difficulties arising due to packaging and merging of silicon based technology with PDMS based soft lithography techniques. Due to the absence of a scalable control strategy for droplet based microfluidic systems, most droplet systems are currently designed as linear channels. Multi-layer soft lithography-based microfluidic devices use external solenoids that are much larger than the fluidic chip and are external to the device. As the complexity of the chip increases, the number of control lines increases drastically, making it intractable as a scalable control strategy. Moreover, control elements made using multi-layer soft lithography cannot be cascaded, resulting in limitation of scaling. As an analogy to the microelectronics revolution that occurred in the 1960's and 1970's, massive scaling of electronic circuits was only possible by moving every element of the circuit on a single integrated chip itself. Similarly, for micro-fluidic chips to provide the same complexity commonly seen in electronic counter parts, all control and logic elements must be designed to be completely on-chip.

Table 1 lists relevant forces in fluid dynamics and their dependence on Reynolds number, with examples of their use as a flow control technique.

TABLE 1

| | Re | Programmability | Flow control eg. |
|---|---|---|---|
| * Surface Tension | independent | surface energy patterning; D. Bebee et al. | Passive capillary valves and control |
| Boundary layer separation | Re > O(100) | Structure of the channel | Drag reduction using active control |
| Electro-hydro dynamic instabilities | Re < O(10) | HighV electrodes integrated in microchannels | Electro kineatic chips |
| * Two phase flow Inertial forces | independent high; Re > O(500) | device structure flow interaction | None Diodes, triodes, amplifiers, gates centrifugal force "lab on CD" |
| Wall attachment | Re > O(100) | flow interaction | bistable amplifiers |

An all-fluid control and logic circuit using non-newtonian fluids was proposed recently [Groisman, Alex et al., "A microfluidic rectifier: Anisotropic flow resistance at low Reynolds numbers", *Physics Review Letters,* 2004; Groisman et al., "Microfluidic memory and control devices, *Science,* 2003]. Several devices, including a bistable memory and a microfluidic rectifier, were proposed. The nonlinearity of the system comes from using non-newtonian fluids. A polymer-based solution is used as the acting fluid, with polymer chains stretching and compressing, which provides a nonlinear behavior to the fluid. Use of non-newtonian fluids severely limits the applicability of these devices in various situations.

Fluids with polymer additives have been used to implement a constant flow source and a bistable gate [Groisman, Alex et al., "A microfluidic rectifier: Anisotropic flow resistance at low Reynolds numbers", *Physics Review Letters*, 2004; Groisman et al., "Microfluidic memory and control devices, *Science*, 2003] but the operation of these devices is dependent on non-Newtonian fluid properties. Change in flow resistance has been used [T. Vestad, D. W. Marr, T. Munakata, *Appl. Phys. Lett.* 84, 5074 (2004)] to build Boolean logic in a single-phase Newtonian fluid, but since its input and output representation are not the same these devices could not be cascaded. Bubble logic, based on hydrodynamic bubble-to-bubble interactions, is similar in bit representation to theoretical billiard ball logic [E. Fredkin, T. Toffoli, *Int. J. Phys.* 21, 219 (1982)] based on the elastic collision of particles, and magnetic bubble memory [H. Chang, Magnetic Bubble Logic: Integrated-Circuit Magnetics for Digital Storage and Processing (IEEE Press, 1975)] relying on interactions of magnetic domains in garnet films. These schemes all conserve information because, during a logic operation, a bit is neither created nor destroyed.

Various control strategies for microfluidic devices have been proposed using thermally generated vapor bubbles. Thermally generated bubbles from micro-heating elements have been previously used in ink jet applications. A vapor bubble is used to push on a fluid layer that is ejected out of the channel. A mechanical structure can also be moved using a thermally generated vapor bubble [Schabmueller, C G J et al., "Design and fabrication of a microfluidic circuit board", *Journal of Micromechanics and Microengineering*, 1999]. However, the device requires integration of heating elements in fluidic channels with mechanical structures, and the control is limited by the rate of generation of thermally induced vapor bubbles. Thermally generated vapor bubbles are transient in nature, and vapor bubbles dissolve in surrounding liquid as soon as the heat source is removed, so any effect caused by presence of vapor bubbles is short lived. Using a heating element for bubble generation also results in unwanted thermal effects on the biomolecules and reactions being carried in the microfluidic device.

Microfluidic "lab-on-a-chip" devices, where picoliters of fluids can be precisely manipulated in microscopic channels under controlled reaction conditions, have revolutionized analytical chemistry and biosciences. Recent advances in elastomeric pneumatic micro-valves [Marc A. Unger and Hou-Pu Chou and Todd Thorsen and Axel Scherer and Stephen R. Quake, *Science* 288, 113 (2000) and large scale integration [Todd Thorsen and Sebastian J. Maerkl and Stephen Quake, *Science* 298, 580 (2002)] have enabled complex process control for a wide variety [C. C. Lee et al., *Science* 310, 1793 (2005), F. K. Balagadde, L. You, C. L. Hansen, F. H. Arnold, S. R. Quake, *Science* 309, 137 (2005)] of applications in single phase micro-reactors. Pneumatic elastomeric micro-valves require external macroscopic solenoids for their operation. Cascadability and feedback (where a signal acts on itself), which are common in electronic control circuits, are currently lacking in microfluidic control architectures.

Another problem in microfluidics is reagent interaction with channel walls, which causes dispersion and non-uniform residence time distribution due to Poiseuille flow (parabolic flow profile). Several reaction chemistries have been implemented in segmented-flow two-phase micro-reactors, where individual nanoliter droplets traveling inside microchannels are used as reaction containers [K. Jensen, A. Lee, *Lab Chip* 4, 31 (2004), B. Zheng, L. S. Roach, R. F. Ismagilov, *J. Am. Chem. Soc.* 125, 11170 (2003)]. Di-electrophoretic [P. R. C. Gascoyne et al., *Lab Chip* 4, 299 (2004)] and electrostatic [D. Link et al., *Angew Chem. Int. Ed.* 45, 2556 (2006)] force based external control schemes have been proposed on-chip droplet management, but they all require independent control of a large number of external electrodes and provide only single gate level control, which limits scalability. Flow control that exploits the dynamics of droplets inside microchannels would make high-throughput screening and combinatorial studies possible [M. Joanicot, A. Ajdari, *Science* 309, 887 (2005)], but preliminary implementation of passive control techniques [Y. C. Tan, J, S. Fisher, A. I. Lee, V. Cristini, A. P. Lee, *Lab Chip* 4, 292 (2004), G. Cristobal, J. P. Benoit, M. Joanicot, A. Ajdari, *Appl. Phys. Lett.* 89, 034104 (2006)] has not provided single droplet control.

Current printing technologies are dependent on numerous droplet-on-demand generation mechanisms using piezo, thermal, acoustic as actuation element. The head is mounted on a mechanical moving stage, which is translated precisely on a receiver substrate utilized for printing. Scaling for high-throughput printing thus requires a very large number of integrated printing nozzles on the same cartridge, which are controlled simultaneously. Current printing methods directly take a small amount of ink from the ink reservoir and transfer it to the receiving substrate. Thus very little manipulation/chemical processing/pre-arrangement is possible before the drop is transferred on the substrate. Also colors are generated via a multiple number of steps by printing with different colors at the same spot, increasing the printing time. This is due to the limitation that only a very fixed number of ink reservoirs (typically four) can be stored and accessed by the cartridge. Finally, pre-processing like dithering, font generation and numerous other operations are performed electronically by the printer before an image is generated.

In-line sample analysis, to evaluate the quality of a given product/output, requires installation of a detection/measurement instrumentation inline with the production site. To sample a large number of locations over a long period of time is cost prohibitive. For example, tracking the water supply of a location over a period of 24 hrs (at a given rate, say every 15 minutes) requires large amount of automation in generating time stamped samples and performing an online analysis or measurements. The method for tagging a sample with date/time/location and other parameters is also cumbersome in conventional methods. This is crucial for correctly labeling a sample, thus requiring storage of information with the sample.

Two methods of fabrication/assembly of different materials exist. One is top-down fabrication where a complex object is made from bulk material by subtracting parts. The other approach is a bottom-up approach, where parts are assembled from small entities using numerous approaches such as self-assembly and/or directed-assembly. Self-assembly techniques suffer from errors that are incorporated in the device. Also, it is not possible to program the structure of the object to be made. This limits the type of objects that can be fabricated by self-assembly. Directed assembly can be guided to form the exact parts/shapes/objects required. The current bottleneck in directed assembly exists in limitations that exist in precise manipulation of a large number of very small parts forming the object/device. Thus the throughput from a directed assembly technique is low. To form complex parts, the capability to handle a very large number of parts to be assembled in a seamless, integrated manner is required.

Single-cell analysis platforms provide the capability to study a large cell population, one at a time. Current cytometry techniques allow fast sorting and classification of cells into several clusters. Thus a population of cells can be studied and classified based on various selection criteria such as type, size, expression and so forth. This is achieved by high-end microscopy techniques such as multi-color florescence detection, which make it possible to detect small amount of signals from individual cells. Current techniques use bulky fluid handling and delivery techniques which also limit post-processing capabilities where the identified sampled could be further processed. In a similar situation, Single molecule studies are usually performed in solution using bulky and expensive optical probes or patch clamp techniques. Current techniques require tedious manipulation mechanisms and hence can not be automated or used for high-throughput analysis of a large number of individual molecules, such as mixture of things that exist inside a cell.

Previous fluid logic demonstrations at low reynolds number therefore have various shortcomings, including use of non-newtonian fluids, with consequent non-linear flow properties, use of an external switching element like a solenoid, limiting achievable device speed, difference in representation of input and output signal thus inability to cascade logic gates to form a complex boolean gate, and an inability to scale to large and complex microfluidic droplet/bubble circuits. In addition, there is a limitation in providing input to microfluidic chips, because the input must be provided serially using valves based on solenoids located outside the chip. With increasing complexity of the chips, more and more information needs to be input into the system, so this limitation results in a bottleneck. In addition, the number of control lines needed to run a microfluidic chip currently increases drastically with the complexity of the designed chip. This is because the switching elements cannot be cascaded to form complex control networks. What has been needed, therefore, is a system that uses only newtonian liquids, logic elements that are cascadable, exhibit gain and fan-out, and can switch faster than previous devices, and a system that is scalable to large and complex microfluidic droplet/bubble circuits.

SUMMARY

The present invention is an all fluid-based no-moving part micro-mechanical logic family that works for very low Reynolds number, thus making it possible to build devices at micron-sized scales. The working principle is based on minimum energy interfaces in two-phase newtonian fluid-dynamic systems. The devices also utilize the principle of dynamic resistance, which can be described as a large increase in flow resistance of a channel due to presence of an air bubble/droplet in the channel. The input to the system is a sequence of bubbles or droplets that encodes information, with the output being another sequence of bubbles or droplets. The micro-mechanical logic family of the present invention includes logic devices, modulators, pressure sensors, actuators, and an all-fluidic means to control them based on two-phase fluid flow in microchannels. The present invention demonstrates non-linear behavior for logic operations, bistability, gain, and fan-out, which are necessary and sufficient for universal computation.

Various devices, including AND, OR, and NOT logic gates, non-volatile bistable memory, shift registers, multiplexers, and ring oscillators have been designed and fabricated. Complex microfluidic circuits are easily formed by cascading individual logic gates into larger circuits. The devices work on the principle of minimum energy interfaces formed between the two fluid phases enclosed inside precise channel geometries. Thus, bubbles/droplets inside another immiscible fluid take the path of least resistance while flowing through a complex network of microfluidic channels. If there is a drastic increase in the resistance of a channel caused by the presence of a bubble/droplet, the path of least resistance for another bubble/droplet can be dynamically reconfigured. Systems employing air in water, water in oil, oil in water, and other immiscible fluids are all suitable. For an air-water system, information is represented as the presence (high bit) or absence (low bit) of an air bubble. Thus, the input and output for the system is encoded as a precise pulse sequence of air bubbles. This results in a digital representation of information in the system. Another representation, wherein the rate of bubbles arriving at a point encodes information, can also be used. A hybrid representation where both rate-based encoding and exact bubble pulse-based encoding can also be employed in the devices of the present invention. On-demand bubble generators and annihilators are used to encode and destroy information in the bubble logic devices. Micron-sized bubbles can therefore be precisely produced and routed with temporal and spatial control within these microfluidic circuits. Since no information is lost regarding bubble operations, conservative logic using bubble logic devices can be built.

The typical microfluidic bubble logic device of the present invention consists of some sequence of complex microfluidic channels, a set of microfluidic bubble modulators that are used to program the device, and microfluidic droplet/bubble memory elements that are used for chemical storage and retrieval. In one particular embodiment, the system can be envisioned as a three-phase system, with oil being a dispersion phase, air bubbles being used as control elements, and water droplets being used as tightly confined reaction sites. For performing a set of reactions/tasks on chip, the modulators program the device by producing a sequence of bubbles/droplets precisely timed, resulting in a cascade of logic operations of generated bubbles as control, and input bubbles/droplets from the reagents. The final products from the device are trapped in bubble traps and can then be extracted. Since the operations can be either sensed on-chip or visually monitored, feedback can be provided to the chip providing the possibility of closing the control loop.

In one aspect of the present invention, universal Boolean logic is implemented in physical fluid dynamics. This provides a droplet-level, internal, inherently digital, flow control mechanism for microfluidic processors. The present invention does not require off-chip components and can scale to complex structures. A bubble traveling in a micro-channel can represent a bit of information as well as carry a chemical payload, thus making it possible to integrate chemistry with computation for process control. Using such bubbles, the present invention demonstrates the nonlinearity, gain, bistability, synchronization, cascadability and feedback required for a scalable universal logic family. Bubble logic preserves the information representation from input to output, thus devices can be cascaded allowing implementation of combinatorial and sequential Boolean circuits. A bubble can be transported to a desired location in a complex microfluidic network via a series of cascaded logic gates corresponding to an equivalent Boolean circuit. Such an implementation of digital logic for process control also provides a modular design approach for droplet control architectures, where individual logic gates can be connected in a hierarchal structure.

In the present invention, universal computation and bistability is demonstrated in an all-fluidic two-phase microfluidic system. Nonlinearity is introduced in an otherwise linear, reversible, low Reynolds number flow via bubble-to-bubble hydrodynamic interactions. A bubble traveling in a channel represents a bit, providing the capability to simultaneously transport materials and perform logical control operations. Bubble logic AND/OR/NOT gates, a toggle flip-flop, a ripple counter, a timing restoration device, a ring oscillator and an electro-bubble modulator are possible. These show the nonlinearity, gain, bistability, synchronization, cascadability, feedback and programmability required for scalable universal computation. With increasing complexity in large-scale microfluidic processors, bubble logic provides an on-chip process control mechanism integrating chemistry and computation.

BRIEF DESCRIPTION OF THE DRAWINGS

Other aspects, advantages and novel features of the invention will become more apparent from the following detailed description of the invention when considered in conjunction with the accompanying drawings wherein:

FIGS. 6A and 6B depict an example embodiment of a bifurcating channel logic gate with gain according to one aspect of the present invention;

FIG. 12 depicts an example embodiment of cascaded logic gates according to one aspect of the present invention;

FIG. 25 is an example embodiment of a bubble modulator employed as a display element, according to one aspect of the present invention;

DETAILED DESCRIPTION

Figure 1:
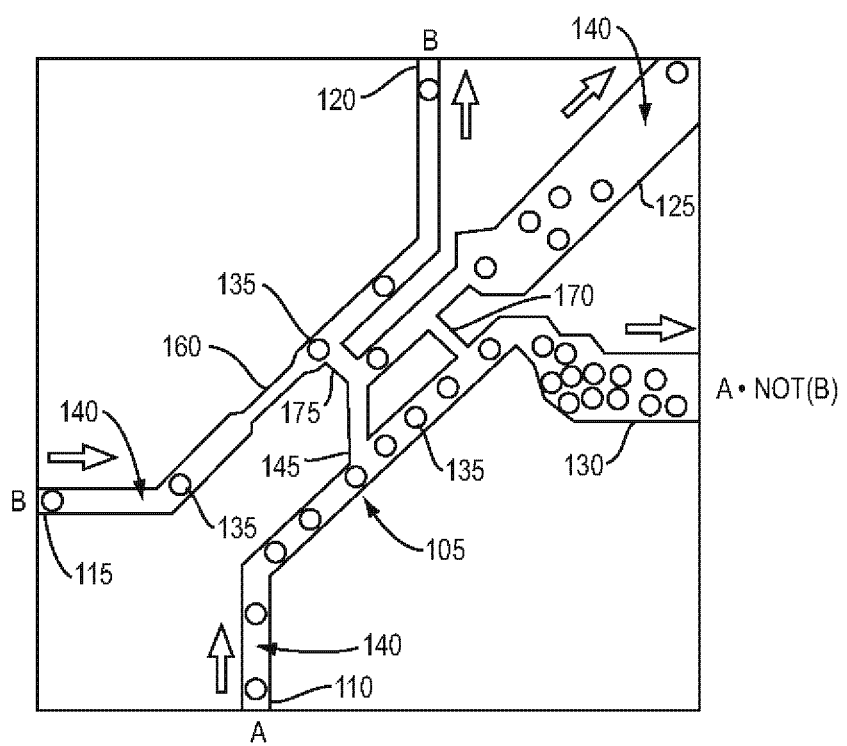
FIG. 1 is an example embodiment of a microfluidic bubble logic gate according to one aspect of the present invention.

The present invention is an all fluid-based no-moving part micro-mechanical logic family. The fluidic logic of the present invention works for very low reynolds number, thus making it possible to build devices at micron-sized scales. This is the first time an all-fluidic, no moving-part logic family has been designed that employs newtonian fluids at small length scales. The working principle is based on minimum energy interfaces in two-phase newtonian fluid-dynamic systems. The input to the system is a sequence of air bubbles encoding information, with the output being another sequence of air bubbles.

The micro-mechanical logic family of the present invention includes logic devices, modulators, pressure sensors, actuators, and an all-fluidic means to control them based on two-phase fluid flow in micro-channels. Miniaturized microfluidic devices based on micron-sized channels and complex plumbing networks are extensively used as a research platform in several areas including biotechnology and analytical chemistry. With the invention of these miniaturized networks, logic and control circuits for very large-scale integrated microfluidic systems have become necessary if it is desirable to take advantage of the high-throughput and massive parallelization that is possible. The present invention is micro-mechanical fluidic logic machinery capable of providing complex control logic for microfluidic devices. Microfluidic circuits can thus be designed in a modular fashion with control logic embedded in the fluidic devices themselves, thus requiring no external electronic control or off-chip control elements. This also makes the microfluidic system highly integrated and portable, permitting its use in field applications.

Bubble logic technology can also be employed to build mechanical information processing devices and micro-mechanical control systems. Moreover, since the system employs mass transport as a means to propagate information and perform various operations, it provides a platform for logically processing small amounts of different fluids (much like a traditional microcontroller processes electrons), thus making miniature large-scale materials-processing units possible. Thus the information carrying unit, a bubble/droplet in a channel, can also carry a material payload (such as, for example, bio-molecules, single cells, reactants, etc.). This results in a highly integrated material and information processing platform. The elements are field-produceable and can be manufactured on a desktop size setup. The functioning of these devices is based on liquid-liquid interfaces (which is a highly accessible nonlinearity), avoiding the use of highly ordered semiconductor materials used in the information processing industry. The nonlinearity in the devices is introduced from the boundary conditions of the air-water interface using only newtonian liquids.

The present invention demonstrates non-linear behavior, bistability, gain, and fan-out, which are necessary and sufficient for building universal computation and non-volatile memory elements. Fluid dynamics of single-phase flow at low reynolds number in micro-geometries is inherently linear due to negligible inertial forces. Nonlinearities in two-phase flow devices have been studied before [Thorsen, Todd et al., "Dynamic pattern formation in a vesicle-generating microfluidic device", *Physics Review Letters*, 86(18):4163-4166, April 2001]. In a two-phase system with moving interface boundary, the equations describing the flow conditions are highly nonlinear. This nonlinearity is exploited in the fluidic devices of the present invention. Various devices, including AND, OR, and NOT logic gates, complex boolean logic, diodes, counters, non-volatile bistable memory, shift registers, multiplexers, and ring oscillators have been designed and fabricated. Furthermore, complex microfluidic circuits are easily formed by cascading individual logic gates into larger circuits. The logic implementation can be further subdivided as static or dynamic. The dynamic logic family employs moving bubbles and bubble-bubble interaction as a nonlinear phenomenon. The static implementation of logic gates involves air bubbles trapped in specified geometries.

Two schemes are utilized for analog and digital bit representation for the present invention. This provides the state restoration benefits associated with digital logic. The structures are simple to fabricate and consist of no moving parts. Well-known soft-lithography techniques are used to fabricate current embodiment of the devices. The devices employ planar fabrication techniques accessible on a desktop scale. Thus, it is possible to produce logic elements in the field. The initial aspects of the research from which the present invention arose are described in "Micro-mechanical Logic for Field Produceable Gate Arrays", Manu Prakash, Department of Media Arts and Sciences, School of Architecture and Planning, Massachusetts Institute of Technology, 2005, which is herein incorporated by reference in its entirety.

The present invention allows implementation of a microfluidic universal logic family at low reynolds numbers using only newtonian liquids. The mechanism involves bubble-bubble interaction in designed geometries that provide for the required non-linearity. The interaction can be either direct bubble-bubble interaction or indirect bubble-bubble interaction via hydrodynamic forces communicated through the surrounding liquid. The non-linearity arises from boundary conditions representing the air-liquid (or liquid-liquid) interface. The logic family represents input and output signal as a sequence of bubbles/droplets. Since the input and output signals use the same representation, the devices can be easily cascaded to form complex all-fluidic circuits. A particular benefit of the described logic family is its switching speed.

The devices work at a kHz range, thus making them the fastest available switching elements (two orders of magnitude faster, as compared to currently used microfluidic elements) for an all-fluidic system. The logic family has fan-out, which is achieved by splitting bubbles at junctions. Although the embodiments described may employ air bubbles in water, as the currently preferred implementation, the present invention is not limited to air bubbles in water and can alternatively use droplets of one material in another immiscible liquid as dispersion phase.

The devices work on the principle of minimum energy interfaces formed between the two fluid phases enclosed inside precise channel geometries/confinements due to surface energy minimization. An air-water based two-phase system where air bubbles are suspended inside water is described, but similar schemes employing water in oil, oil in water, and other immiscible fluids are also suitable. For an air-water system, information is represented as presence (high bit) or absence (low bit) of an air bubble. Thus, the input and output for the system is encoded as a precise pulse sequence of air bubbles. On-demand on-chip air bubble generators and annihilators are used to encode and destroy information in the bubble logic devices. Micron-sized air bubbles can therefore be precisely produced and routed with temporal and spatial control within these microfluidic circuits.

The mechanical logic devices and derived cascaded circuits can be used for many applications. The logic family makes possible design of an entirely mechanical family of complex control circuits. The circuits can be used for logic applications requiring high resistance to electromagnetic fields. Non-volatile bistable fluidic memory can be designed using the proposed scheme. The devices can be used for non-volatile all-fluidic displays. The devices can be employed as a control strategy for droplet-based microfluidic systems. The control system only employs a fluid-based control, as opposed to an electronic control scheme. Several advantages include a more scalable control scheme, extremely simple fabrication techniques, and no unwanted side effects due to induced electric fields in case of electronic control. Various fluidic micro-mechanical actuation schemes are also conceivable. The devices can be used for various combinatorial and large-scale automated reagent-based processes, thus replacing the need for expensive mechanical robots used for combinatorial chemistry and drug discovery applications. Currently, various schemes exist for embedding bio-molecules, cells, and reaction agents inside droplets in microfluidic system. The logic family of the present invention can also be used as an on-chip high throughput sorting device that separates different type of elements in a microfluidic device.

The typical microfluidic bubble logic device of the present invention consists of some sequence of complex microfluidic channels, a set of microfluidic bubble modulators that are used to program the chip, and microfluidic droplet/bubble memory (e.g., loop memory) elements that are used for on-chip chemical storage and retrieval. For performing a set of reactions/tasks on chip, the modulators program the chip by producing a sequence of bubbles/droplets precisely timed. This results in a cascade of logic operations of generated bubbles as control, and input bubbles/droplets from the reagents. Finally, the products from the chip are trapped in bubble traps, and can then be extracted.

FIG. 1 is an example embodiment of a microfluidic bubble logic gate according to one aspect of the present invention. In FIG. 1, a sequence of microfluidic channels 105 of varying diameters is interconnected in a complex pattern. Similar to an electrical signal-based digital logic gate, there are multiple input channels, in this case, A 110 and control input B 115, and multiple outputs, B 120, B 125, and A.NOT(B) 130. For performing a set of reactions/tasks on chip, one or more microfluidic bubble modulators produce a timed sequence of bubbles/droplets 135 that are sent within fluid 140 into the microfluidic channels at inputs A 110 and B 115 as the input to the logic gate, producing outputs B 120, B 125, and A.NOT (B) 130 that result from the interactions between the bubbles and the microchannel geometry and the bubbles with each other. Bubbles 135 represent information, as the presence of a bubble implies a bit of information. Channel A 110 is divided at bifurcation 145 into two channels, while channel B 115 has constriction 160 right before joining a branch from channel A 110. There are two pressure bypass connections 170, 175, one between two branches of input channel A 110 after the bifurcation and another one between channel B 115 and one branch of channel A after narrow constriction 160. Bypass connections 170, 175 help to normalize the pressure between the two branches, thus cutting off any variations in pressure far away from the device. The example of FIG. 1 is specifically a bifurcating channel-based bubble A AND (NOT (B)) gate, but any type of digital logic gate may be constructed according to the principles of the present invention, including, but not limited to, the specific examples described herein.

The device of FIG. 1 can be used as a NOT gate with a constant stream of bubbles in channel A 110. Thus, whenever there is a bubble in channel B 115, a bubble from channel A 110 is pulled in the upper part of bifurcation 145, removing it from downward part of the bifurcated channel. Thus an operation NOT(B) can be performed using a constant stream of bubbles in channel A 110. The reason that the bubble from channel A goes into the upper branch only when there is a bubble in channel B is that, once the bubble in channel B 115 passes through constriction 160, it blocks the net flow of water in channel B, greatly increasing the flow resistance of the channel. Thus, this behavior can be described by dynamic resistance, a steep increase of resistance of the microchannel to flow whenever the channel is carrying an air bubble/droplet. This increase in resistance reduces the net flow in the topmost channel coming from channel B 115, causing flow switching to occur at bifurcation 145, thereby resulting in more flow from channel A going into the upper bifurcation of channel A as compared to the lower one. More flow in a channel means more net force on a bubble in the channel, which then results in a bubble getting pulled from channel A into the upper channel. With no control bubble in channel B, all bubbles from A end up entering the lower branch of channel A.

From combinations of NOT gates and AND gates, any universal Boolean logic circuit may be constructed. Thus, FIG. 1 demonstrates that the present invention comprises a universal logic family. The bubbles can alternatively be replaced by droplets, which can carry required chemical species as a payload in a water in oil based system. Thus, the system is capable of performing both information and materials processing on a chip in a highly integrated manner. The system can be implemented using various two-phase fluid systems including oil in water, water in oil, air in water, etc. Air in water based bubble logic devices are described for simplicity, but other two-phase immiscible newtonian fluids may also be employed. The non-linearity exploited in the devices is the dynamic interface shape for two immiscible liquids. Since a liquid bubble tries to minimize the interface energy of a liquid gas system, certain energy minima exist for the bubble in a defined geometry. The energy landscape can be changed by applying pressure of inducing flow, thus manipulating the bubbles to a new location. The interaction between the bubbles can also be communicated via hydrodynamic forces through the surrounding liquid.

Utilizing the present invention, logic gates based on bubble-bubble interaction may be created. Bubble-bubble interaction is necessary for designing a non-linear gate. Direct and indirect bubble-bubble interaction phenomena are used in various devices as needed. Direct interaction devices are based either on bubble fusion and fission considering change in bubble volume, or for non-fusing bubbles (stabilized by a surfactant), by change in air-water interface shape. Indirect interaction is governed by the pressure difference across a bubble and hydrodynamic forces generated by presence of a bubble in a confined geometry. Example nonlinear logic devices employing this methodology are described herein and include, but are not limited to, the path of least resistance based AND/OR gate, the bifurcating channel based flow-switching gate, the bifurcating channel gate with positive gain, the cross junction AND/OR gate, the bubble fusion fission based AND/OR gate, and the ring NOT gate.

Different on-chip bubble generators are used along with the logic gates. Spatial and temporal control of bubble interaction is obtained by using shift registers as propagating path for the bubble. For example, for bubble coalescence, employing shift register-like structures ensures temporal control over the coalescence. The described devices can also be driven by a pulsing pressure field, which is equivalent to the clock frequency used in electronic circuits. Bubbles in the logic gates can therefore be driven at a fixed clock frequency.

Path of Least Resistance-Based (Constriction-Based) AND/OR Gate.

Resistance of a bubble contraction can be defined in terms of total free surface energy change when a bubble is moved from a large channel to a narrow channel. Only surface energy change for the bubble is evaluated, with the energy loss due to streamlines converging and various other viscous dissipations being ignored. Consider a channel traveling from a capillary of radius R to a narrow capillary of radius r. An external pressure $P_R$ and $P_L$ is assumed around two bubble interfaces where the total pressure drop across a bubble is given by $P_L-P_R$. Considering isothermal quasi static motion of the bubble, the surface energy loss to move the bubble from a large to a narrow channel can be evaluated. The change in energy can be described as:

$$\Delta E_{total}=E_1-E_2=\sigma_{lg}(A_{lg.1}-A_{lg.2})+\sigma_{lg}\cos\theta(rl-RL)$$

where L and l describe the length of the air bubble in the large and narrow channels respectively.

For a large bubble, numerical evaluations show that energy is required to push the bubble from a large to a narrow geometry [Jensen, Mads Jakob et al., "The clogging pressure of bubbles in hydrophilic microchannel contractions", *J. Micromech. Microeng.*, (14):876-883, May 2004]. An analogy can be established to defining a resistance associated with narrow constriction. For a series of constrictions, the resistance can be added in parallel, if there exists a bubble in a constriction. This assumes that this resistance for an air bubble going across a constriction is much larger than the resistance offered by such a constriction to single-phase flow. Thus, a dynamic resistance in a channel can be established, where the resistance of a particular channel to flow suddenly increases drastically when a bubble passes by. This is clearly seen in drastic deformation of bubble shape, and is also the reason for bubble clogging in the channel. The above principle can be used to switch flow in various geometries, resulting in a net force that can then be employed on another set of bubbles/droplets.

Figure 2A:
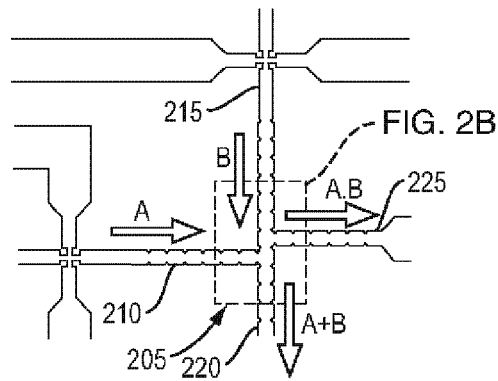
FIGS. 2A-C depict an example embodiment of a constriction-based AND/OR logic gate according to one aspect of the present invention.
Figure 2B:
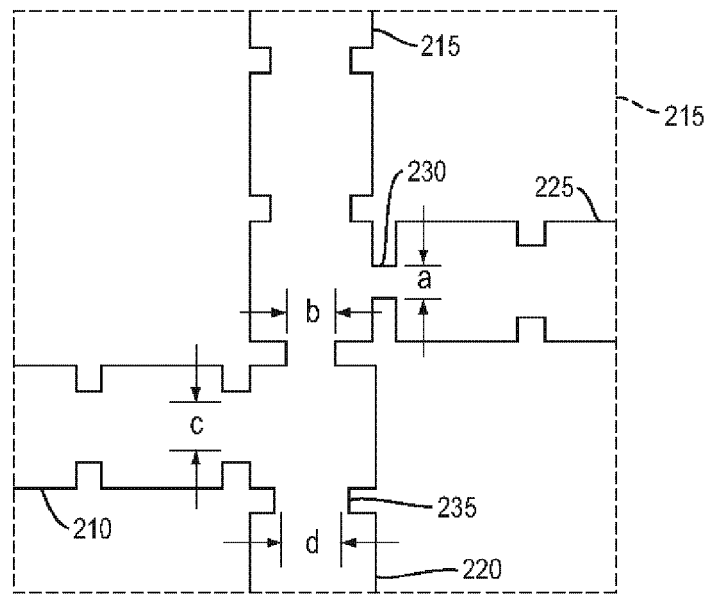
Figure 2C:
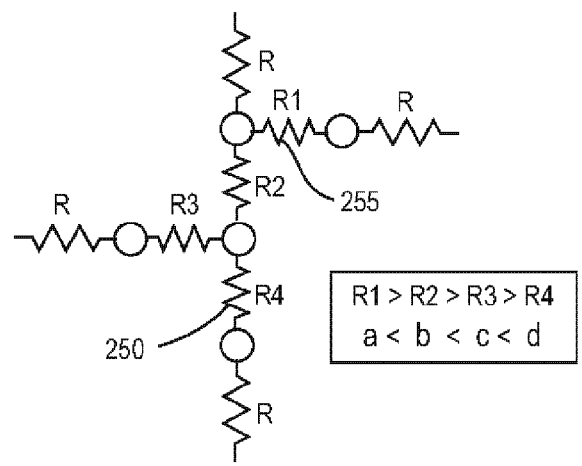

From these principles, a simple resistance based model for the AND/OR gate can be constructed. Thus, devices can be implemented on the basis of path of least resistance. FIGS. 2A-C depict an example embodiment of a constriction-based AND/OR logic gate. In FIGS. 2A-C, a network of channels 205 has two inputs 210, 215 and two outputs 220, 225. The channel geometry is designed for the performance of logic operations. AND and OR gates are implemented simultaneously by this geometry. Thus the logic operation is conservative, in the sense that no information about the input is lost after the logic operation has been performed. In this particular embodiment, input 210 comes from the left channel marked A and input 215 comes from the top channel marked B. The two outputs 220, 225 are generated in channels marked A+B 220 (going downwards) and A.B 225 (going to the right).

Input in the system of FIGS. 2A-C is described as a bubble traveling in a channel. The presence of a bubble is marked as "1" and the absence of a bubble is marked as "0". These bubbles are flowing in another immiscible phase, i.e., water in this particular implementation. Exit channels A.B 225 and A+B 220 have different exit geometries. There exists a narrower constriction 230 in channel A.B 225 (given by length a) than the constriction 235 in channel A+B 220 (given by length d). Thus, if only one bubble arrives at a junction from either A or B, it preferentially goes to the channel with the larger exit path, i.e. the path of least resistance. Thus, when only one bubble arrives, it will always take the path to channel A+B 220. In the case where two bubbles arrive, one each from channels A 210 and B 215 simultaneously, the bubble from channel A 210 goes to channel A+B 220 while the bubble from channel B 215 goes to channel A.B 225. This completes a logical operation on inputs A 210 and B 215.

The same principle is also pictured in FIGS. 2A-C as a compact model depicting the constriction size at a channel as a resistance (in an analogy between the resistance of fluid in a channel to the resistance to the flow of electrons in a wire). Because the smaller the exit constriction, the larger the resistance to flow, channel A+B 220 has a lower resistance $R_4$ 250 than the resistance $R_1$ 255 of channel A.B 225. Step-like geometries on the channel wall act like a shift register, making the bubble travel one length scale in a unit of time. The principle behind the device is based on the fact that air/water interfaces minimize their energy while going through a constriction. Thus, a path of least resistance is offered by the downward going channel A+B. This is the case when either one of A or B is arriving at the junction at an instance of time. If both bubbles arrive at the same time, due to additive nature of pressure drop across a bubble, then the second bubble is forced to take the bath towards A.B. Thus $R_1>R_2>R_3>R_4$ and a<b<c<d, where a, b, c, d represent the constriction in the channel in the order shown in the FIG. 2.

Bubbles from two generators arrive at the intersection, forming an A and B stream. Since the driving pressure is pulsed, the motion of bubbles is in sync, with a unitary shift with every time step. Considering all the possible cases for bubbles arriving from A and B, based on the channel geometry, the path of least resistance for A, whether any bubbles are present or not in channel B is towards channel A+B. For bubbles in channel B, the path of least resistance when no bubbles are present in channel A is also channel A+B. However, when the junction is occupied by a bubble from channel A, that is no longer true, and the bubble from B is instead forced to take channel A.B. Thus, the geometry of the gate of FIGS. 2A-C provides both an AND and an OR gate where, A+B is an OR gate (a bubble flows to channel A+B, if there exists a bubble in A or B) and A.B is an AND gate (a bubble flows to channel A.B only when bubbles are present in both A and B).

AND/OR Gate Based on Bubble Interaction in Parallel Channels.

Figure 3A:
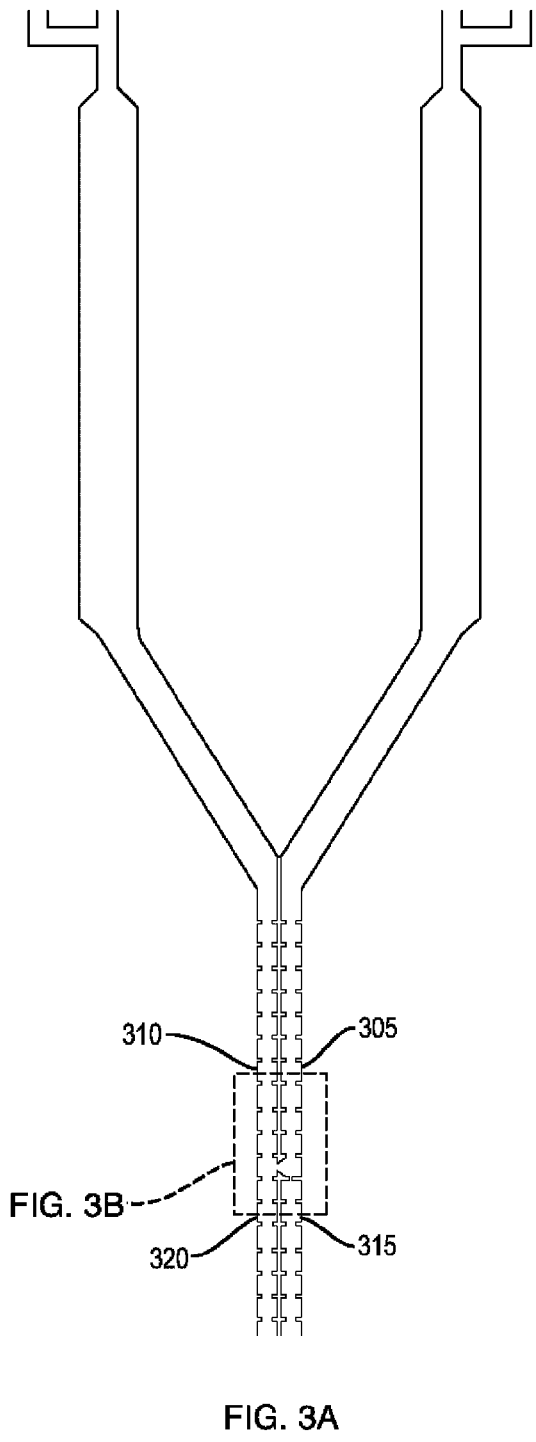
FIGS. 3A and 3B depict an example embodiment of an AND/OR gate based on bubble interaction in parallel channels according to one aspect of the present invention.
Figure 3B:
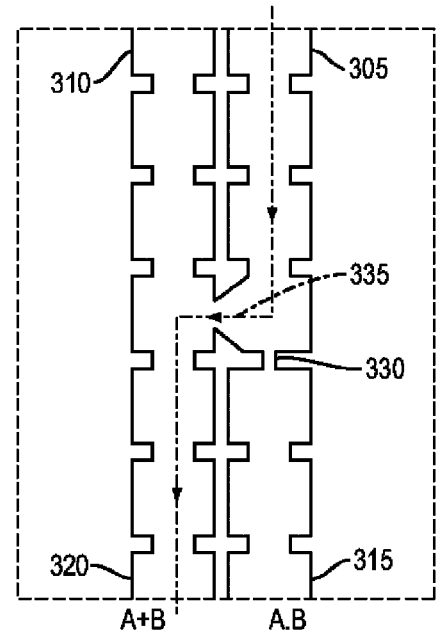

Another device based on path of least resistance is shown in FIGS. 3A and 3B, which is an AND/OR gate based on bubble interaction in parallel channels. The device principle is very similar to the gate of FIGS. 2A-C, though the geometry is based on a lateral interaction of two bubbles in parallel channels. In FIGS. 3A and 3B, an AND/OR logic gate has two input channels 305, 310 and two output channels 315, 320. Each input channel 305, 310 consists of a microfluidic channel with input being represented as the presence or absence of a bubble inside the channel. Each output channel 315, 320 consists of a microfluidic channel having the presence or absence of a bubble. Input channels 305, 310 are marked A and B respectively, while output channels 315, 320 are marked A.B and A+B respectively. Bubbles traveling in a microchannel with another immiscible phase (water in the currently preferred implementation) represent information or a bit stream. Each channel consists of step-like geometry on the sides. This acts like a shift register moving the bubbles forward a unit distance in unit time. At the junction of channels A 305 and B 310, the geometry is designed so that the entry 330 from channel A 305 to channel A.B 315 is very narrow. Thus, a bubble coming from channel A 305, in the absence of a bubble in channel B 310 that is simultaneously coming with a bubble in channel A, results in the bubble in channel A 305 moving sideways 335 into channel A+B 320. This occurs because it requires a higher pressure to push the bubble through narrow constriction 330 into channel A.B 315 as compared to pushing it sideways at junction 335 into channel A+B 320. Also, if there is a bubble coming from channel B 310, it preferentially goes into channel A+B 320, since that is the path of least resistance for the bubble. Once two bubbles simultaneously arrive at junction 335, a bubble in channel A 305 is forced to enter channel A.B 315 due to hydrodynamic feedback from the bubble in channel B 310. The bubble in channel B 310 blocks the flow from A to B, thus reducing the net force applied by the flow field on the bubble in channel A. As pressure in channel A builds up, there is a threshold of pressure that is reached when the force is sufficient to make the bubble in channel A pass through constriction 330 and enter channel A.B 315. Thus, an AND and an OR gate are implemented by the device of FIGS. 3A and 3B. As in the device of FIGS. 2A-C, both channels A and B are driven by a pulsating pressure periodic in time. The pressure acts like a driving clock, providing control over the interaction of the bubbles. With no driving pressure, bubbles are most stable in the enlarged chambers (connected together by narrow constrictions); however, an air bubble present in one channel forces the bubble in the second channel to flow from a path with a larger constriction.

AND/OR Devices Based on Bubble Interaction in Opposing Channels.

Figure 4A:
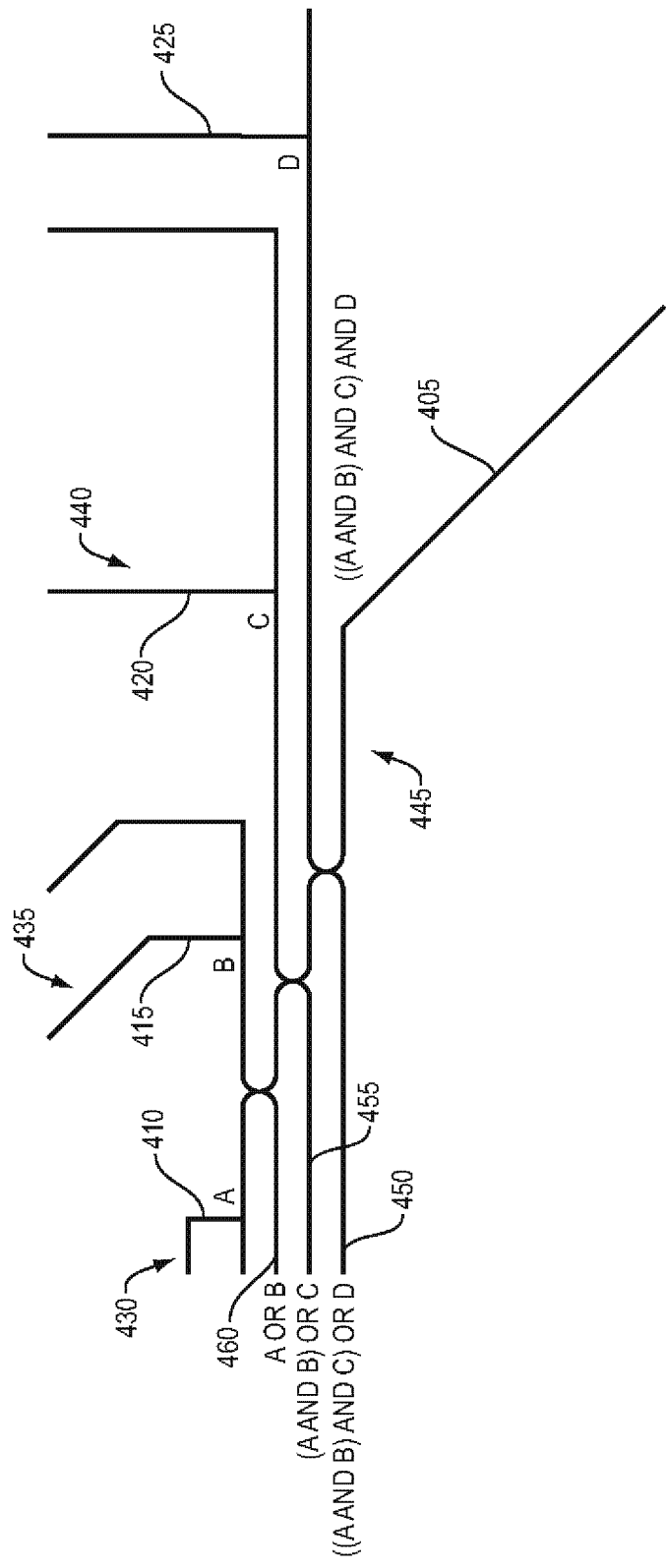
FIGS. 4A and B are representations of example embodiments of AND/OR devices based on bubble interaction in opposing channels, according to one aspect of the present invention.

Another type of AND/OR device based on path of least resistance is based on bubble interaction in opposing channels, as shown in the examples of FIGS. 4A and B. In FIG. 4A, a circuit is constructed from cascaded Boolean logic gates and computes the function (((A AND B) AND C) AND D) as an output 405 from inputs A 410, B 415, C 420, and D 425. A network of channels is formed by cascading (joining in series) three logic gates 430, 435, 440 that each perform both AND and OR logic operations given two inputs. Thus, the three logic gates in series simultaneously compute the following Boolean operations: (((A AND B) AND C) AND D) 405, (((A AND B) AND C) OR D) 450, ((A AND B) OR C) 455, and (A OR B) 460. A bubble in the channel represents a bit, a unit of information. The bubbles are generated at T-junctions A 410, B 415, C 420, D 425. The particular sequence of bubbles generated at an input can be controlled using a bubble modulator. Thus, the cascaded gate of FIG. 4A takes 4 inputs and produces 4 outputs. In this particular embodiment, T-junctions are used to generate the air bubbles in water solution. The particular AND/OR logic gate used in the example embodiment of FIG. 4A is the gate of FIG. 1. Since the input, represented as the presence of a bubble in input channel and the output, represented as the presence of a bubble in output channel are essentially the same entity, logic gates may be cascaded to perform complex Boolean operations on multiple input lines. This results in the ability to perform the scaling that is necessary for very large scale integrated all fluidic circuits.

Figure 4B:
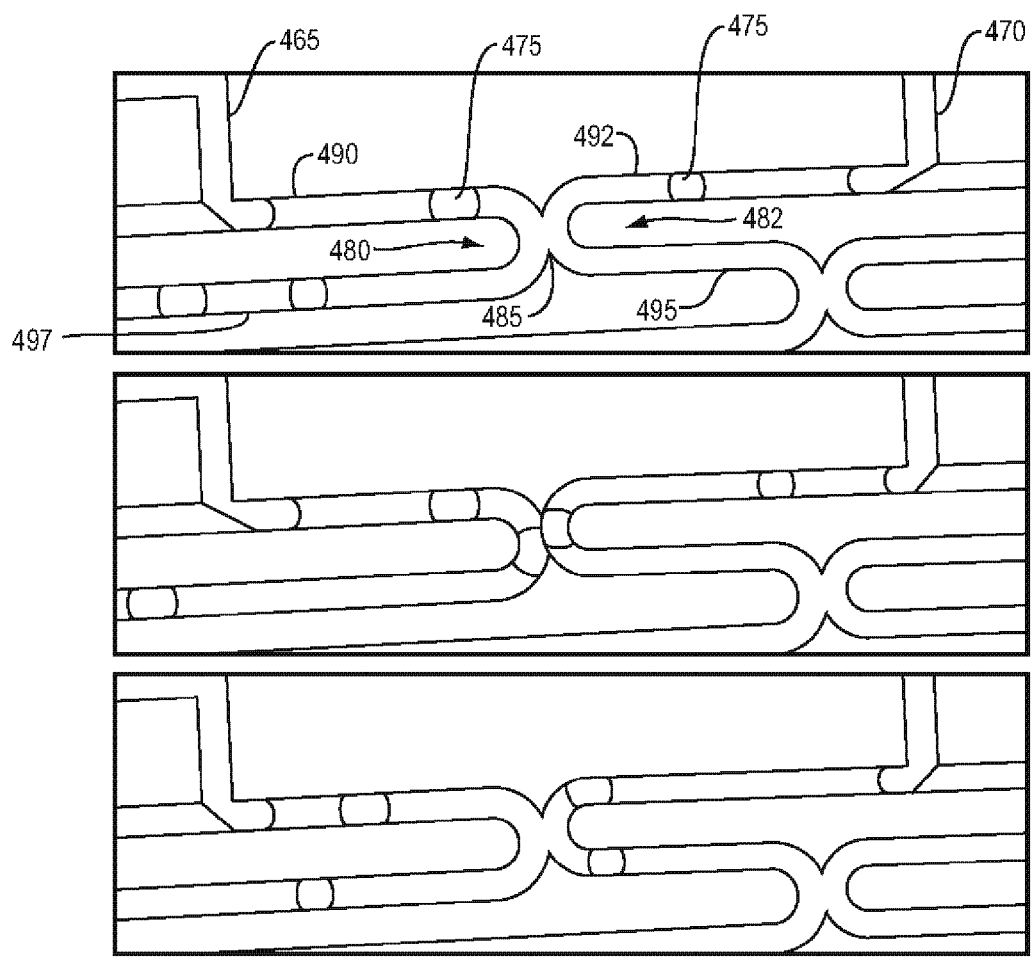

FIG. 4B, depicts a working AND/OR logic gate of FIG. 4A in actual operation. The complex network of channels represents the logic gate and two input and output channels with T-junction based bubble generators. T-junctions 465, 470 in the channels represent inputs A and B. This is where the bubble signals are generated. Air bubbles 475 in the channel appear as circular boundaries, with water surrounding them. The device consists of two C shaped channels 480, 482 joined back to back. An important aspect of the geometry of this embodiment is the asymmetry in junction 485, where input to junction 485 from the top is provided via equal sized channels 490, 492, and the exit has two channels 495, 497, with one on the right 495 having a smaller width than the one going to the left 497. This results in asymmetric distribution of flow in the devices. More flow therefore goes into the channel with the least resistance (larger entry width). Thus, when one input bubble from either of top channels A 465 or B 470 comes to junction 485, it invariably goes to channel 497 on the left. However, when bubbles from both A 465 and B 470 arrive simultaneously at junction 485, the bubble from B 470 is forced to take channel 495 to the right, since the larger channel exit 497 is temporarily blocked by the bubble from channel A. Thus, output channel 497 to the left of junction 485 performs the logic operation A+B, while channel 495 to the right performs the logic operation A.B. In the preferred embodiment, the average channel width of the channels of FIG. 4B is 100 micron wide, operating in a low Reynolds number flow regime (roughly Re=0.1).

Bifurcating Channel-Based Flow Switching Gate.

The working principle for a flow switching bubble logic gate is based on the bifurcation of the flow stream at a junction. Thus, the bubble in an equally distributed bifurcating stream can go to either of the two outgoing streams. With a bias applied to the channel resistance, the bubble will preferentially always go in one direction instead of the other. The bifurcating channel is then coupled to another channel that controls the flow in a one-output channel at the bifurcating junction. This control channel also has a narrow constriction so that when a bubble passes by, the pressure of the flowing fluid suddenly jumps while the net flow drops sharply, because of the increased resistance to flow created by the squeezing of the bubble through the narrow channel. This results in flow from the bifurcating channel increasing in this branch of the device, resulting in the bubble at the junction entering into this channel. As soon as the control bubble passes through the constriction, the resistance falls back to normal, returning the net flow at the bifurcation to the initial state. The channel can optionally be joined by various bypass pressure passages to equalize the pressures at various points. This gives rise to normalized pressure at the output ports of the device, making it prone to noise or fluctuations in pressure at the output ports.

Figure 5A:
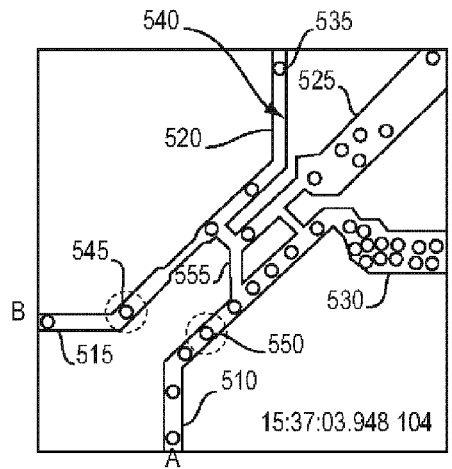
FIGS. 5A-C depict an example embodiment of a bifurcating channel based bubble A AND (NOT(B)) gate according to one aspect of the present invention.
Figure 5B:
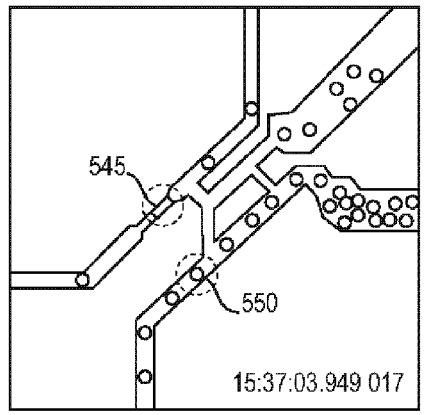
Figure 5C:
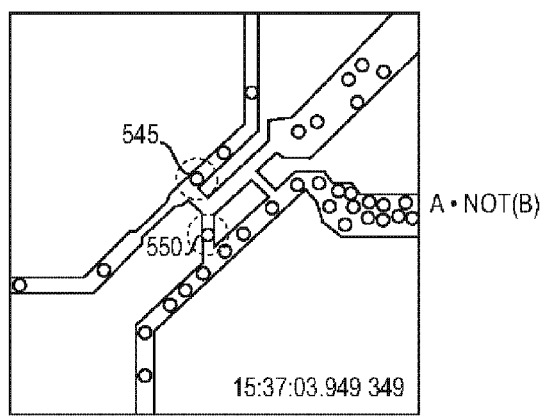

FIGS. 5A-C depict a bifurcating channel-based A AND (NOT(B)) gate over time. In FIGS. 5A-C, three successive image clips from a movie of a working A AND (NOT (B)) gate of FIG. 1 are seen. The time signatures, obtained from the high speed video camera used to capture the movie clip, provide evidence of the fast switching speeds of these devices. As in FIG. 1, the gate of FIGS. 5A-C consists of two inputs 505, 510 and three outputs 520, 525, 530. Only one of the outputs contains useful information, which is channel 530, [A AND(NOT(B)] (lowermost channel). In the preferred implementation, the channels are made in PDMS using soft lithography with a width of 100 microns and height of roughly 75 microns. Circles 535 are air bubbles with de-ionized water 540 flowing around the same. Bubbles 535 are stabilized using a surfactant solutions mixed in water (tween 20, 2% by weight). This reduces the surface tension of the interface, thus avoiding breaking up of drops/bubbles at sharp corners.

Bubble 545 in channel B 515 is a control bubble, while bubble 550 in channel A 510 is an input bubble. As is clear from the three images, bubble 550 from channel A 510 is pulled into middle channel 555 because of the presence of bubble 545 in channel B 515. The rest of the bubbles 535 before and after bubble 550 in channel A 510 proceed to go straight in channel A AND (NOT (B)) 530. Thus, the logic operation is performed on input stream A based on control stream B. The total time of the operation is roughly 1.2 milliseconds, implying that the switching frequency of the operating device is 803 Hz. Therefore, the devices normally operate in the kHz regime, which is two orders of magnitude better than any all-fluidic logic gate shown in prior literature. The gate can be used both as an AND gate or a NOT gate. For operation as a Not gate, the input A is always kept at "1" (i.e. a constant stream of bubbles). The device can also be engineered to have a positive gain (a small bubble switching a larger size bubble).

Bifurcating Channel Gate with Gain.

For scaling of digital devices, gain is an important measure of how well a switching element works. Gain is also crucial in very large scale integration to create complex Boolean circuits. In the present invention, the signal strength of a bubble is measured by its size. Thus, if a smaller bubble can cause switching in a larger channel, that would be positive gain. Similarly, if a control bubble can switch more than one input bubble, that also constitutes positive gain.

FIGS. 6A and 6B depict a bifurcating channel logic gate with gain. In FIG. 6, an A AND (NOT B) gate with gain is depicted at two points in time, $T_1$ and $T_2$. The gate is a complex network of channels containing bubbles 605 with water 610 flowing around them. Input channel A 615 bifurcates into two output channels 620, 625. Second input channel B 630 enters the top branch 620 of the bifurcated channel at narrow constriction 635. Bubbles from channel B 630 are referred to as control bubbles, while bubbles in channel A 615 are called input bubbles. The flow at the bifurcation is divided between the two channels. Bubbles from channel A 615 will go into the branch 620, 625 that has more net flow. Therefore, with no control bubble in channel B 630, all bubbles from channel A 615 will enter channel 620. However, when a control bubble is present in channel B 630, the bifurcated flow is disturbed. This is called a flow switching event, and it results in more net flow from the bifurcation into top channel 625. This is because the net flow from channel B 630 is suddenly reduced, because of the presence of a bubble in constriction 635.

There is also a bypass channel 645 between the two bifurcated branches 620, 625, which equalizes the pressure between the two branches. This hydrodynamic bypass results in isolating the device from variations in pressure far away from the device, making it possible to cascade the device without one device affecting the other. Gain in the device of FIGS. 6A and 6B is described as the ratio of the total volume of bubbles switched to the volume of bubbles used in the control channel, or $n.L_i/L_c$ where n is number of bubbles switched, $L_i$ is size of the input bubble and $L_c$ is the size of the control bubble. It is also possible to switch a larger bubbles using a much smaller bubble, thus providing a positive gain from the system. In FIGS. 6A and 6B, at time $T_1$, smaller control bubble 650 switches two input bubbles 655, while at time $T_2$, longer control bubble 660 switches three input bubbles 665. The gain is therefore in proportion to the size of the control bubble. Longer bubbles have a larger resident time in the constriction, thus allowing a much longer flow transition at the bifurcation, resulting in larger gain. Changing the constriction geometry (making it narrower) results in a smaller bubble switching a larger bubble. Thus, even though the size of a bubble might get smaller after a cascade of cycles, it can be restored by applying the principle of gain.

Cross Junction AND/OR Gate.

One embodiment of a cross junction AND/OR gate according to the present invention is somewhat similar in functionality to the billiard ball logic gates proposed in Fredkin, Edward et al., "Conservative Logic", *International Journal of Theoretical Physics,* 21:219-253, 1982, where the notion of conservative logic was introduced. In this embodiment, non-coalescing bubbles are used as carriers that are repelled at a junction to take different output paths. The bubbles are stabilized by using a very small quantity of a surfactant in the liquid solution (2% Tween 20 in de-ionized water from Millipore). At the junction, the constriction size determines the preferred path for the bubble. Various variations in geometry have been successfully fabricated for the cross junction device.

Figure 7:
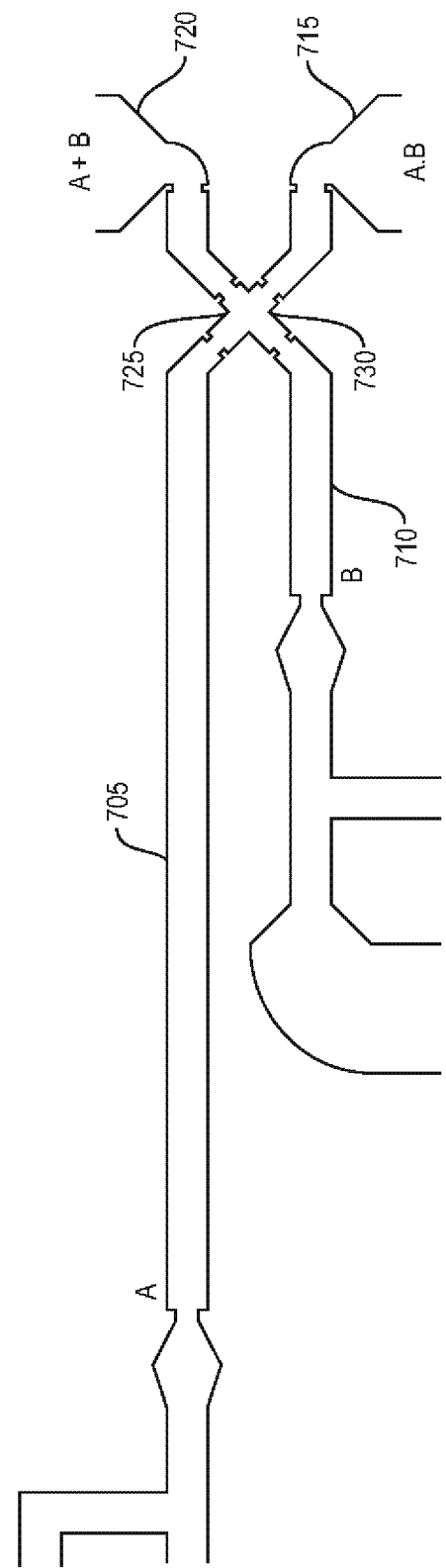
FIG. 7 is an example embodiment of a cross junction AND/OR gate according to one aspect of the present invention.

FIG. 7 is a depiction of one embodiment of a crossover-based AND/OR gate. In FIG. 7, the gate implementation is again based on the principle of path of least resistance. T-junctions are used in this device to generate the bubbles in input channels A 705 and B 710. The device has two output channels, A.B 715 and A+B 720. The entry channels 725, 730 to channel A.B 715 and channel A+B 720 have different geometry. Channel 725, which joins the junction to channel A+B 720 is larger in width than channel 730, which joins the junction to channel A.B 715. Thus, if only one bubble enters the channel from either channel A 705 or channel B 720, the path of least resistance for the bubble leads it into channel A+B 720. When two bubbles arrive at the junction simultaneously, the bubble from channel B 710 is forced into channel A.B 715, since the entrance to channel A+B 720 is blocked hydrodynamically by the bubble from channel A 705.

Fusion Fission Based Logic Device.

Figure 8:
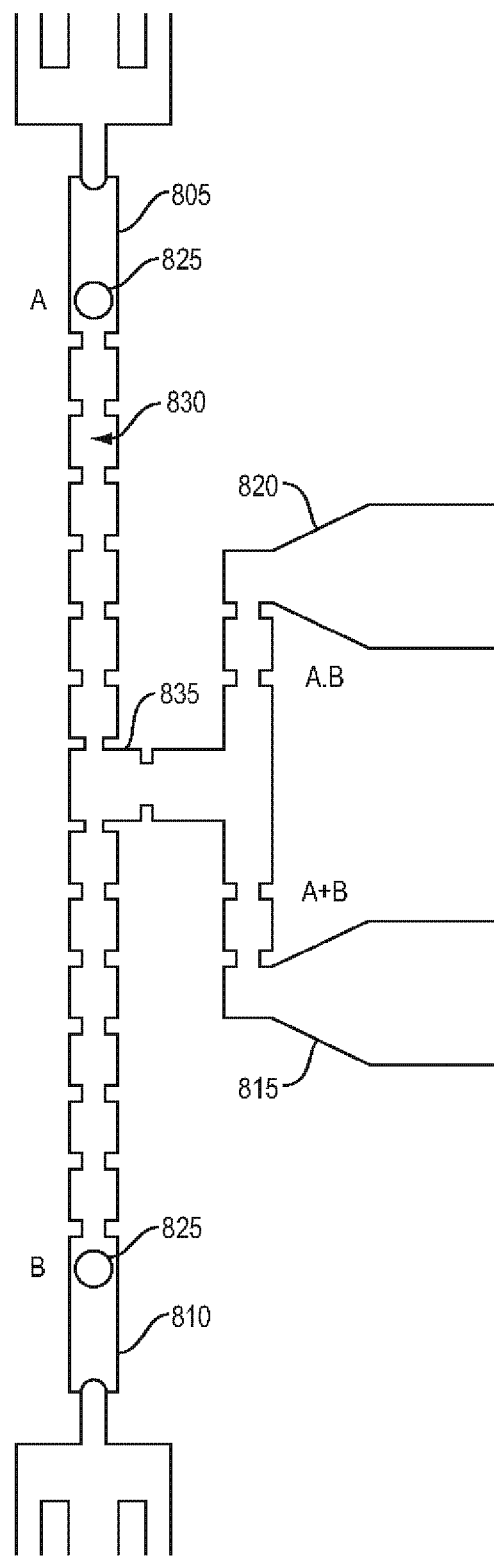
FIG. 8 is an example embodiment of an AND/OR gate based on fusion and fission of air bubbles according to one aspect of the present invention.

Fusion and fission of droplets in microfluidic channels have been studied previously [Chronis, Nikolas et al., "Tunable liquid-filled microlens array integrated with microfluidic network", *Optics Express,* 2003; Jeong, Ki-Hun et al., "Tunable microdoublet lens array", *Microstructure Devices,* 2004]. An AND/OR logic gate using controlled coalescence and splitting (fusion and fission) of bubbles is shown in FIG. 8. In FIG. 8, two input channels 805, 810 and two output channels 815, 820 contain air bubbles 825 traveling in water 830. If only one bubble arrives at junction 835 of the two channels 805, 810, it takes the path of least flow resistance, resulting in all bubbles going to channel A+B 815. If bubbles from channel A 805 and channel B 810 arrive simultaneously at junction 835, they coalesce to form a larger bubble. This larger bubble is then split into two bubbles, based on interfacial shear on the bubble, each resulting bubble going to one of output channel A.B 820 and A+B 815, resulting in a logic operation on the input bubbles.

In FIG. 8, the channel contains a regular pattern of constrictions that act like a shift register, moving a unit distance in unit time. Since the size of the splitting region is matched with the total volume of fused bubbles, fission only occurs in the limiting case when two bubbles have been joined together in previous step. If a smaller bubble is passed through to the fission geometry, it passes through without splitting towards channel A+B 815, thus performing an OR operation. When a bubble is split (the case when bubbles from both A and B are present), one of the bubbles is forced to take channel A.B 820, thus performing an AND operation.

Ring NOT Gate.

The basic principle for a ring not gate according to the present invention is similar to that of the flow switching gate. Two channels join at a junction forming a ring. With no control bubble, the input bubble enters the channel with larger flow. With a control bubble present, the flow at the junction is blocked due to increased resistance. This results in flow switching at the junction, causing switching of the output channel into which the input stream flows.

Figure 9A:
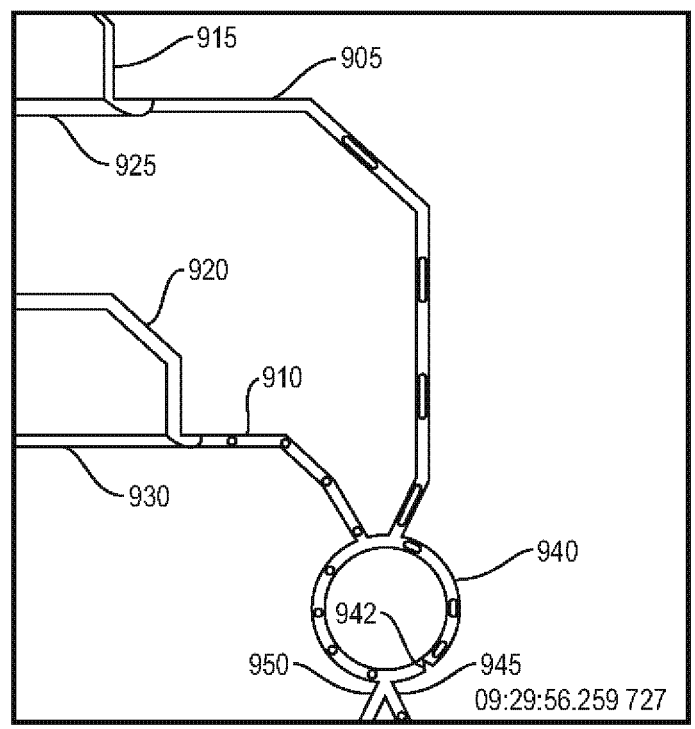
FIGS. 9A and 9B depict an example embodiment of a ring NOT gate according to one aspect of the present invention.
Figure 9B:
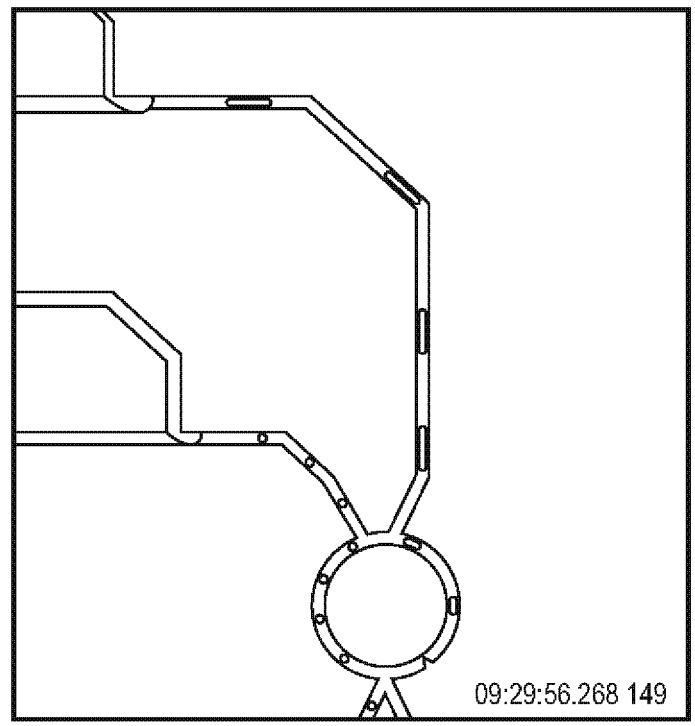

FIGS. 9A and 9B depict an embodiment of a working ring NOT gate according to the present invention at two time intervals. In FIGS. 9A and 9B, the gate consists of a control line 905 (top left) and an input line 910 (to the bottom left). The control and input bubbles are generated using a T-junction. Each T-junction has one channel 915, 920 containing a pressured air line, while the other channel 925, 930 contains a water line. This results in the formation of a bubble stream. A modulator can be used to produce a stream of bubbles that can be precisely programmed. Inputs 905, 910 join together at circular ring structure 940, with the branch carrying control line 905 having a narrow constriction 942. Bubbles flowing in control line 905 are delayed for a fraction of a time unit at constriction 942, building up the pressure in line 905. Once the pressure is high enough, the bubble progresses forward and exits via exit output channel 945. If there is no control bubble, all bubbles from input channel 910 exit from output 950, flowing to the output that has the maximum width flow lines. Once a control bubble blocks one half of ring 940, the flow is switched, with maximum net flow entering output channel 945, resulting in the bubble from input channel 910 entering output channel 945. FIGS. 9A and 9B are taken from image clips from a movie of working devices, so the timestamps shown should put the speed of operation of the device into context. The channels in the working embodiment are roughly 100 microns in width and 75 microns in height.

Bubble Modulator.

A bubble generator that can be synchronized to an electronic signal is used to modulate information in the devices of the present invention. Bubbles can be generated on demand, allowing synchronization of the arrival of bubbles at a gate. The microfluidic bubble modulator of the present invention converts an electrical digital signal into a bubble sequence that may be used as a control sequence in microfluidic bubble logic gates. The size and frequency of the bubbles can be independently controlled. Any given set of bubble sequences can be produced using the device. Since there exists a static balance at the air-water interface present at the junction, a feedback loop can be employed to reduce any variations in pressure and flow conditions. Since the interface can be sensed, e.g. via capacitive electrodes, or optically observed, the control loop can be closed by varying the input pressure in the air line and the flow rate in the water channel in order to maintain the static balance of forces at the interface.

In a preferred embodiment, the bubble modulator utilizes change in surface tension with temperature. A platinum micro-heater is integrated in a flow-focusing device, thus modulating the surface tension at the air-water interface. The interface is static in nature with force balance from pressure, viscous stresses, and surface tension forces at the interface. The applied heat pulse perturbs this delicate balance by decreasing the surface tension at the interface, resulting in a bubble being released in a channel. The modulator is designed with a funnel shaped inlet that stabilizes the interface when the heater is turned off. The bubble generator is driven by a constant air pressure supply and a constant flow of water. The interface is stationary up to a critical pressure, beyond which the air thread penetrates the liquid and pinches to form a drop. With a current pulse applied to the heating element, the static balance is perturbed and a drop is formed every heating pulse. The volume of drops generated is dependent on the length of time that the microheater is switched on, while the frequency of bubble generation is dependent on the periodicity of the total heating cycle. Thus, the above mechanism can be used from very low frequencies (e.g. a couple of Hz), to high frequency (kHz).

Figure 10A:
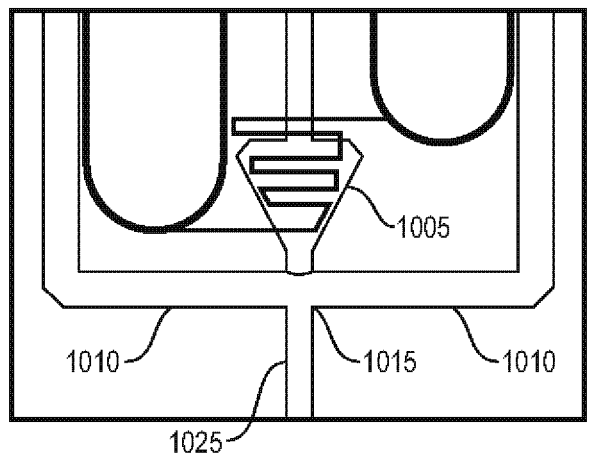
FIG. 10A-C depict an example embodiment of a heating based programmable bubble modulator according to one aspect of the present invention.
Figure 10B:
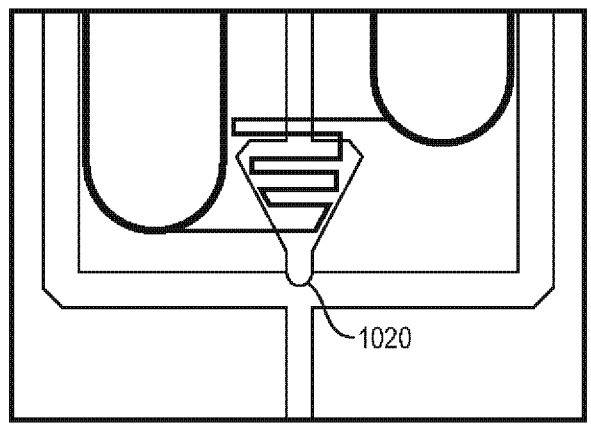
Figure 10C:
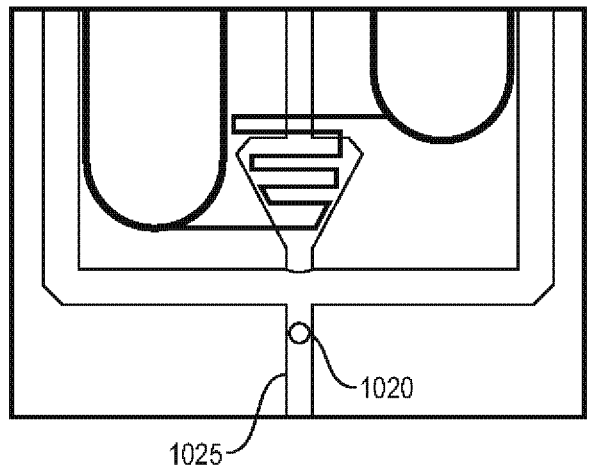

FIGS. 10A-C depict an embodiment of a heating-based programmable bubble modulator. In FIGS. 10A-C, the bubble modulator is running at 30 Hz. The bubble modulator utilizes a constant pressure air line, a constant flow fluid line, and an electrical pulse train as an input pulse and generates a train of output bubbles synchronized to the electrical input pulse. This mechanism is used to generate an information stream in the system and to program the microfluidic devices. The modulator is capable of generating an electrically programmable train of bubbles/droplets with precise time synchronization. Both the size of the generated bubble and the precise time of bubble release can be tuned using the electrical signal.

In FIGS. 10A-C, three microfluidic channels join together into one output channel. Central input channel 1005 contains a constant pressure air line, while outside input channels 1010 have constant water flow. Air input channel 1005 has a funnel geometry that stabilizes the air-water interface at junction 1015. This results in a static balance and a stationary interface without the application of an electrical pulse. In a preferred embodiment, the device is fabricated with channels in PDMS. The device also contains platinum micro-heaters that are deposited on a glass substrate using e-beam and photolithography. The heaters also have a layer of deposited SiO2 to electrically isolate them from the fluidic channels. The PDMS channels and the glass substrate with micro-heaters are bonded, thus forming a sealed micro-electro-fluid device.

When an electrical pulse is applied to the micro-heaters, there is a sudden rise in temperature of the air cavity supporting the air-water interface. In a static situation, there exists a delicate balance of pressure, viscous, and surface tension-based curvature forces. With an applied pulse, the temperature rises suddenly, increasing the pressure and reducing the surface tension of the interface drastically. This results in the air thread piercing and entering the liquid. At this time, the micro-heater is switched off, and the temperature returns to normal. The extended thread develops an instability, resulting in a pinch off, so that a single bubble/droplet 1020 is released into output channel 1025. The length of the heat pulse applied to the micro-heater determines the size of the bubble generated, and the exact timing of the pulse determines when bubble 1020 is generated. The bubble modulator of FIG. 10 therefore provides a completely programmable method for generating bubbles/droplets in microfluidic channels with precise and independent electronic control over the volume of generated bubbles/droplets and the time of their generation. While the preferred embodiment uses micro-heaters for the above tasks, other transducers, such as, but not limited to, piezo, optical, and pressure-based transducers can be used to perturb the delicate static balance of the interface, resulting in a single bubble production.

Circuits.

For scaling of devices, it is important that the gates can be cascaded. Since input and output signals are represented by a bubble in a channel, it is possible to build complex logic circuits utilizing the present invention through cascading simple logic gates. The logic representation is conservative in nature, since the bubbles are not annihilated.

Ring Oscillator.

An odd number of NOT gates can be put together to form a ring oscillator. A ring oscillator built from bubble logic gates according to the present invention is shown in FIG. 11A. In FIG. 11A, an all-fluidic ring oscillator is constructed from three NOT gates 1105, 1110, 1115 in a ring. The ring oscillator has an output that switches from high and low periodically. The signal is represented by bubbles 1130 flowing in the microfluidic channels of NOT gates 1105, 1110, 1115. As an input, a fixed frequency stream of bubbles is applied at channel 1140 using a T-junction. Output 1150 of third NOT gate 1115 is connected to input 1160 of first NOT gate 1105. This results in the output of all gates oscillating from high to low, which is represented by the presence and absence of bubbles 1130 in the microchannels.

Figure 11B:
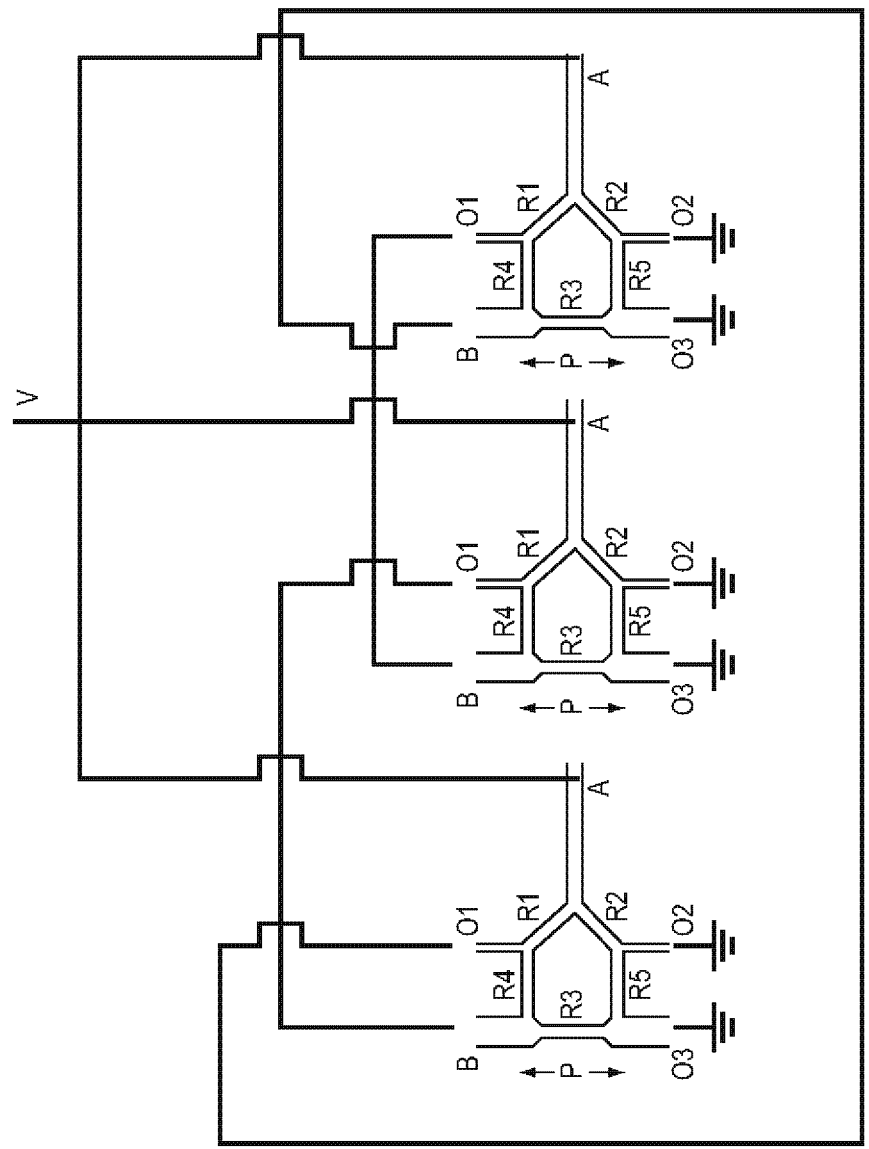
FIGS. 11A and B depict ring oscillators built from bubble logic gates according to one aspect of the present invention.

FIG. 11B depicts an alternate implementation of a ring oscillator. Each NOT gate of FIG. 11B is identical in form and consists of two input and two outputs. The input channel is bifurcated into two channels, while the output channel goes through a constriction that acts like a bypass to the two bifurcated channels. With no control bubble in the channel, bubbles from the input channel all enter the channel in the bottom. When a control bubble is present in the bypass channel, the pressure drop between the top and bottom channel suddenly increases, causing the flow at the bifurcating channel to switch from the bottom channel to the top channel, resulting in a bubble from the input channel entering the top channel. The time it takes to get the bubble from the output of the last NOT gate to input of first NOT gate characterizes the delay in the ring oscillator.

Cascaded Boolean Logic Gates.

The Boolean gates of the present invention can be cascaded to form more complex Boolean gates, since the logic conserves the signal strength (as described by bubble size). Any complex Boolean logic can therefore be built using the bubble logic devices of the present invention. In FIG. 12, an example embodiment of cascaded logic gates that form a Boolean circuit for A.B.C.D is depicted. The circuit also computes (A OR B), ((A AND B) OR C), and (((A AND B) AND C) OR D). In this embodiment, three Boolean gates are connected in series. The top channels have four T-junctions that act as bubble generators. The three logic gates used in this circuit are identical AND/OR logic gates, and the circles in the channels are air bubbles.

Timing Restoration Device.

Figure 13:
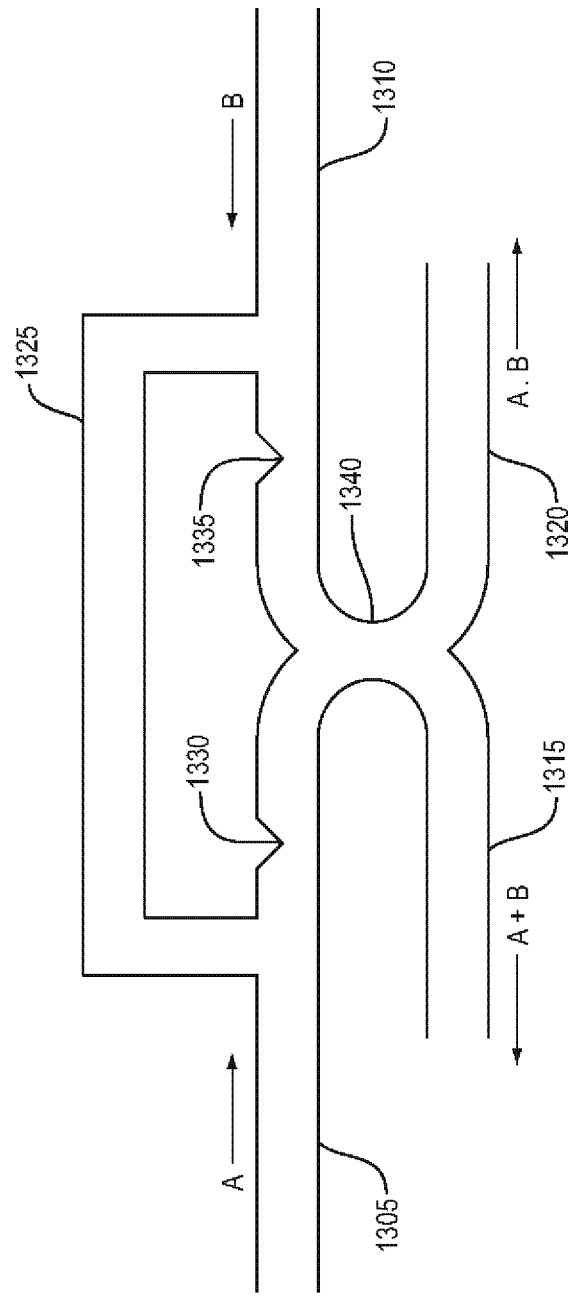
FIG. 13 is an example embodiment of a timing restoration device according to one aspect of the present invention.

Synchronization in arrival timing of bubbles at a junction is important in the present invention. Precise electronically controlled generation of bubbles results in the required synchronization on the chip. However, with any unexpected buildup of time delays, an on-chip correction circuit is needed to remove small amounts of skew that might be present in arrival timings of the devices. This is accomplished by a timing restoration device that synchronizes the signals that are skewed at the arrival of a logic gate. FIG. 13 is an example embodiment of a timing restoration device, added to an AND/OR logic gate, according to one aspect of the present invention. In FIG. 13, there are two inputs A 1305 and B 1310 and two outputs A+B 1315 and A.B 1320. Input channels 1305, 1310 are joined by bypass channel 1325. Input channels 1305, 1310 also include identical constrictions 1330, 1335. When two bubbles arrive at junction 1340 with a skew (delay in timing), one of the bubbles will arrive at an input constriction before the other one. The bubble that arrives first stops at the narrow constriction. Because of bypass flow channel 1325 connecting inputs 1305, 1310, there is no pressure build up because of input channel 1305 clogging. However, once both the bubbles arrive at constrictions 1330, 1335, the pressure builds up and both the bubbles arrive at junction 1340 simultaneously. Small timing errors can therefore be corrected by use of this timing restoration device.

Shift Registers.

The basic principle of bubble clogging is used to construct shift registers. In this manner, air bubbles can be moved with precise temporal control by an applied pressure pulse across a shift register. A large number of propagation geometries have been invented. Since the force needed to push a bubble through a narrow constriction is dependent on the shape of the constriction, various energy profiles can be obtained. As a general principle, the interface shape tries to minimize the total energy of the bubble, thus forcing the bubble to move to the next energy minima. Every profile (except 1405 in FIG. 14) has a periodic minimum along the X-axis, where the interface energy for a bubble trapped is minimized. Thus, precise time control over the movement may be obtained. The present invention includes the concept of clocking for microfluidic devices, since the devices may be run on a fixed pulsating pressure clock.

Figure 14:
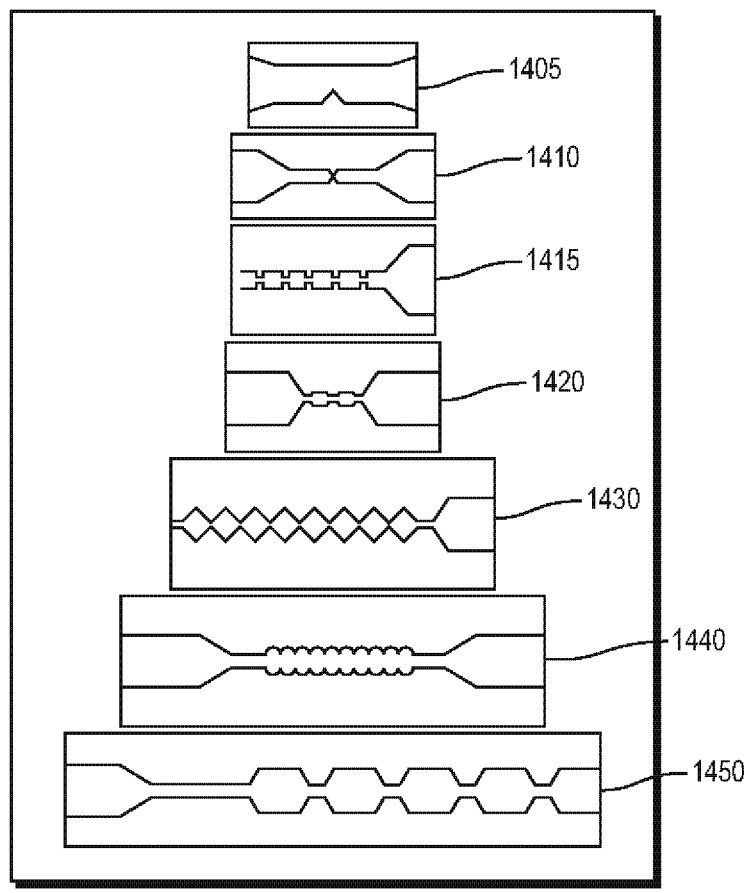
FIG. 14 depicts example embodiments of shift registers for bubbles in microfluidic channels according to one aspect of the present invention.

FIG. 14 depicts example embodiments of shift registers for bubbles in microfluidic channels. In FIG. 14, various geometries used for shift registers in devices according to the present invention are depicted. There exists a commonality in each of the geometries 1405, 1410, 1415, 1420, 1430, 1440, 1450, in that all consist of at least one channel and have at least one symmetric or asymmetric constriction. Thus, the bubbles are forced to contract and relax in a regular pattern while passing through the channel. In this manner, bubbles move a unit distance in unit time. The energy landscape of the geometries consists of a rising and falling energy diagram, taking into account the change in shape of the air-water interface as the bubble passes through the particular geometry. The geometry of the channel wall determines the energy profile along the axis of propagation of the bubble. Because of the differing geometries employed, the shift registers of FIG. 14 all exhibit different energy profiles.

Fan Out (Splitter).

Figure 15:
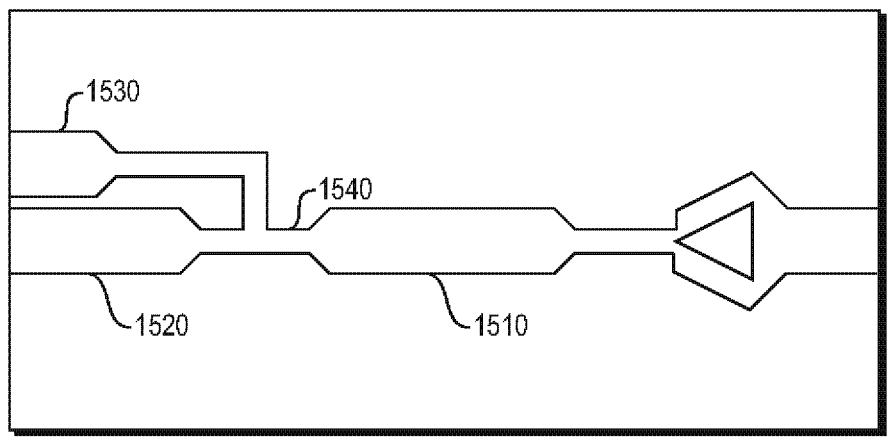
FIG. 15 depicts bubble splitting for the purpose of reproducing information according to one aspect of the present invention.

A single bubble signal, which could be an output of one logic gate, may be used to control multiple gates connected to it, resulting in fan-out. This is achieved by splitting bubbles into multiple smaller-size bubbles. A simple geometry for bubble splitting is shown in FIG. 15. The designed geometry can be used to divide a bubble into two, thus effectively cloning a bit. Bubble splitting at the junction occurs due to shearing flows. It is assumed that the incoming droplet size fills the channel completely. FIG. 15 depicts bubble splitting for the purpose of reproducing information. In FIG. 15, a channel with a T-junction is used to generate bubbles in water channel 1510. Channel 1510 bifurcates into two branches 1520, 1530 having narrow entrance 1540. Such a symmetric split in the channel results in the splitting of an air bubble coming from input 1510 into two bubbles of equal sizes in top and bottom channels 1520, 1530. The output from lower 1520 and upper 1530 channels can be used elsewhere in any device that requires using the input of the splitter for operation. Thus, a single signal stream can be split into two using the above described device. In particular, the embodiment shown FIG. 15 can be used to provide fan-out in the bubble logic devices of the present invention. It is also possible to split a single channel into more than two channels, resulting in a fan out larger than two.

Bistable Memory Element.

Figure 16A:
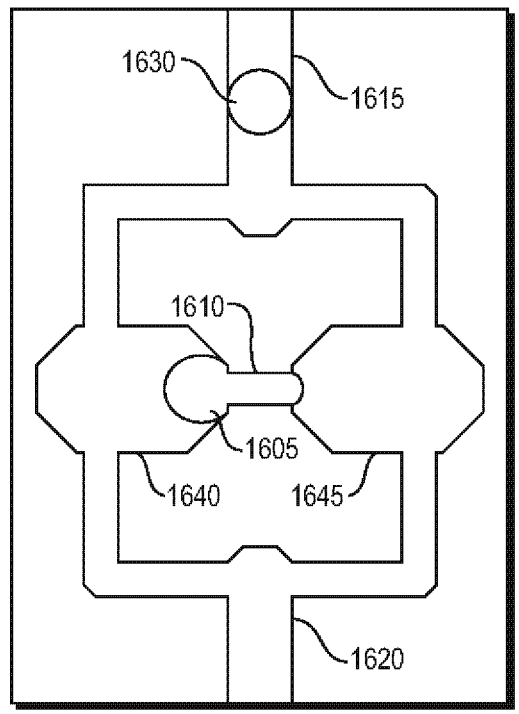
FIGS. 16A and 16B depict the principle of bistability according to one aspect of the present invention.
Figure 16B:
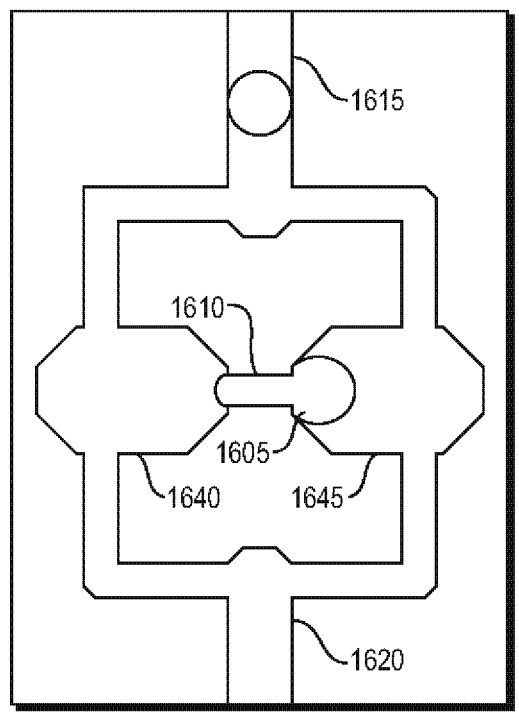

Bistability is an important criterion for information processing devices, because it allows for information storage. A simple constriction-based bistable bubble device is shown in FIGS. 16A and 16B. The channel consists of two chambers tied together by a narrow channel. The two chambers are further bounded by extremely narrow channels, so as to form an energy barrier to escape of the bubble. The energy profile for a bubble in such a geometry is also symmetric, with two energy minima, when the center of mass of the bubble lies at the center of the two chambers. The basic mechanism for bistability is curvature forces at the interface. The most stable position for the bubble trapped in the narrow channel is either to the left of the right, and any slight imbalance in the curvature pushes the bubbles to one side or another, thus providing a bistable nature. A threshold pressure therefore moves the bubble from chamber A to chamber B, thus flipping a bit of information. Readout ports are provided at the chamber that makes non-destructive readout of the memory possible. The state can also be optically read from the device itself. The memory is non-volatile, since it does not require any external energy for the state to remain stable. A large array of such memory elements could find applications in fluidic displays.

FIGS. 16A and 16B depict the two bistable states that are possible in bubble logic devices. Since bubbles/droplets represent not only information in the present invention, but can also be made to carry a payload of chemical/biological species, reactants/reagents can be stored and retrieved on demand in a bubble logic family with bistable states. In FIGS. 16A and 16B, single bubble 1605 is trapped in narrow channel 1610 in the center. The device has one input 1615 and one output channel 1620, with a measurable bistable state that can be switched between states based on entering bubble stream 1630 in input channel 1615. Smaller channel 1610 traps a large bubble that can shuttle from one side 1640 to another 1645 based on the local pressure on the two sides. The pressure can be modulated by introducing a stream of bubbles from input 1615, thus switching the bistable device. The device remains stable when no bubble stream is introduced. The geometry of FIGS. 16A and 16B can be used as the basic memory element in bubble logic family. The memory gates can further be cascaded to form a large array of memory elements.

Bubble Valves and Fluidic Transistors.

Bubble gates that regulate pressure inside a microchannel may be constructed according to one aspect of the present invention. Applications of bubbles for valving in microfluidic devices were proposed in Ki, Y. S. Leung et al., "Bubble engineering for biomedical valving applications", *IEEE-BMBS Special Topics Conference Proceedings,* 2000. However, no location-specific method of generating microbubbles was proposed in this work. The present invention includes valving geometries with a UV transparent glass window that allows for 'writing' bubbles at desired location using excimer laser pulses. This provides a way to generate micro-bubbles of tunable sizes (based on number and frequency of laser excitation).

Figure 17:
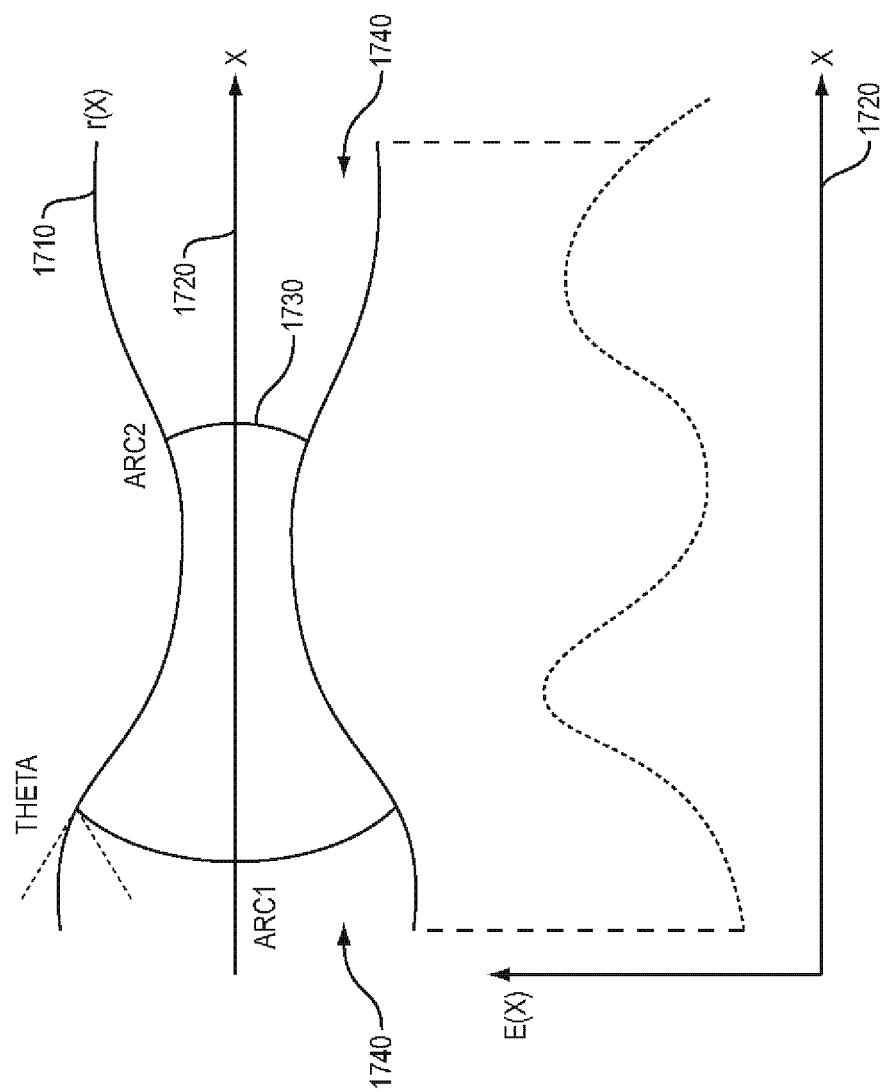
FIG. 17 depicts the surface energy profile of a typical bubble passing through a constriction.

FIG. 17 depicts the surface energy profile of a typical bubble passing through a constriction. In FIG. 17, given a geometry defined by r(x) 1710 varying along x-axis 1720, the energy profile can be calculated along x-axis 1720, where the center of mass for bubble 1730 in liquid 1740 varies along x. The profile varies from geometry to geometry. The partial differential of energy with respect to $x_cm$ gives the force required to balance it.

On/Off Valves.

Families of static logic gates can be used as on/off valves for microfluidic devices. The regulating factor used is differential pressure across the device. Thus, flow can be switched on or off, based on a regulating control pressure. Currently used micro-mechanical valves employ moving parts to control fluid flow. The valves of the present invention have no moving parts. Since pressure is employed as a control factor, the valves can be cascaded together with a positive fan-out. This is currently not possible with existing technologies. The ability to cascade valves permits the design of complex control elements with intricate interdependences. Since the bubble valves are conformable, they perfectly seal the channel with no leakage. The bubbles, once trapped, remain in the confined geometry. They can be used effectively for valving action in microchannels, since they conform to a given geometry thus providing a tight seal around the channel. The simple principle of energy minimization of a bubble is employed to ensure that the bubble comes back to its original position once the control pressure is removed. The bubble in the confined geometry can either be induced using laser cavitation or it may be transferred from an external bubble generator and pushed into the device.

Figure 18B:
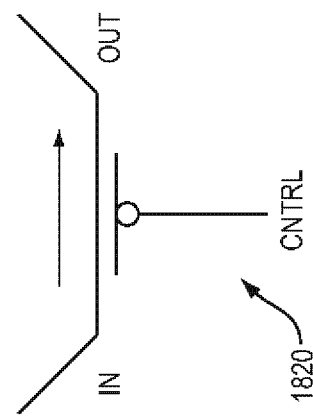
FIGS. 18A and 18B depict a fluid bubble switch based on a confined bubble induced in the chamber according to one aspect of the present invention.
Figure 18A:
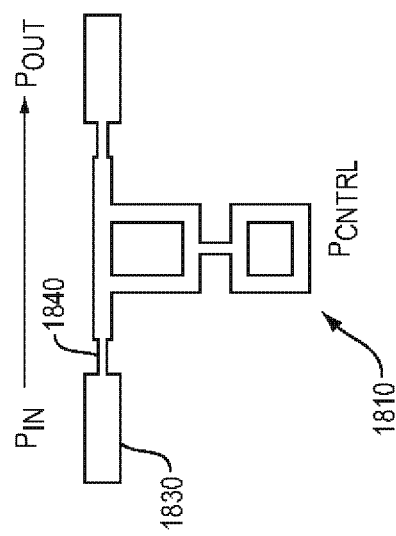

FIGS. 18A and 18B depict a fluid bubble switch 1810 based on a confined bubble induced in a chamber and the electronic circuit equivalent 1820. In FIGS. 18A and 18B, the bubble stays in wider channel 1830 if no control pressure is applied. If a control pressure exists, the bubble is forced to cover narrow region 1840 of the channel, thus shutting the flow in the channel completely. The switching gate of FIGS. 18A and 18B can be used as a valve in a microfluidic device. The advantage of such a valve is that it controls the liquid flow by employing a liquid control pressure. Thus, such valves can also be cascaded in series to perform complex control functions. Also, since the output pressure can be divided into multiple pressure lines, the device has a positive fan-out. The capability of fan-out opens up the possibility of designing complex control networks with interdependent behavior.

Programmatically Writing Vapor Bubbles Inside Micro-Geometries.

For writing air bubbles at specific locations, various techniques to induce vapor bubbles inside microgeometries have been developed. The first technique is based on the use of laser pulses to induce microbubbles in three-dimensional geometries. Cavitation effects occurring in liquid films from short laser pulses have been previously studied in relation to laser based surgery applications [Turovets, Igor et al., "Dynamics of cavitation bubble induced by 193 nm arf excimer laser in concentrated sodium chloride solutions", *Journal of Applied Physics,* 1996]. Thus, stable vapor bubbles of a given size can be written in a microstructure very quickly. The vapor bubbles are induced using a very short (10 nsec) laser pulse at 193 nm. A UV transparent sealing glass is used to make sure the pulse energy is not degraded as it reaches the microchannels.

Another technique uses back pressure from micron-sized pores to induce vapor bubbles. Thus a threshold pressure causes the creation of a bubble on top of the pore. This causes a bubble/droplet of one phase to be suspended inside another.

These small pores can be can programmatically written inside microchannels using wither glass laser micromachining techniques or soft lithography. The described techniques have an advantage over conventionally used methods for generating microbubbles that employ heating elements inside microchannels. This requires integration of fabrication techniques for fluidic networks and heating elements with control circuits.

Air Bubble Based Pressure Sensor.

Pressure distribution with specific flow rates varies with the constructed geometry inside the microchannels. To characterize a device for the pressure loss that occurs due to variations inside a microfluidic channels, various pressure-sensing schemes have been proposed in the literature. Due to the complexity of fabrication of most of the present schemes for pressure sensing, analytical models are more often employed to evaluate the resistance of a microfluidic channel. Pressure sensing inside microchannels is a difficult task, requiring embedded silicon membrane-based pressure probes fabricated inside the microchannels. Optical particle tracking techniques like PIV are highly complex and generally an overkill if only pressure readings along a microchannel are required.

An extremely simple pressure readout device has been implemented based on the present invention. The pressure sensor uses compressibility effects of an air bubble trapped inside a micro-geometry. A simple optical readout of bubble diameter is used to evaluate external pressure outside a micro bubble. Thus, pressure ports can be constructed along a micro-channel with air bubbles trapped inside. A nanosecond laser pulse is employed to direct write air bubbles inside these micro-geometries.

The present invention includes a novel pressure-sensing scheme in complex microfluidic networks. The pressure measurement is based on size of microbubbles in a port connecting to the microchannel. The bubbles do not touch the wall surface and hence are spherical in shape (disregarding gravitation at small length scales). The difference between external and internal pressure of an air bubble is given by $2\sigma/r$, where r is the radius of the microbubble and $\sigma$ refers to the surface tension of air-liquid interface. Hence, the radius of the bubble is directly correlated to external pressure.

Figure 19:
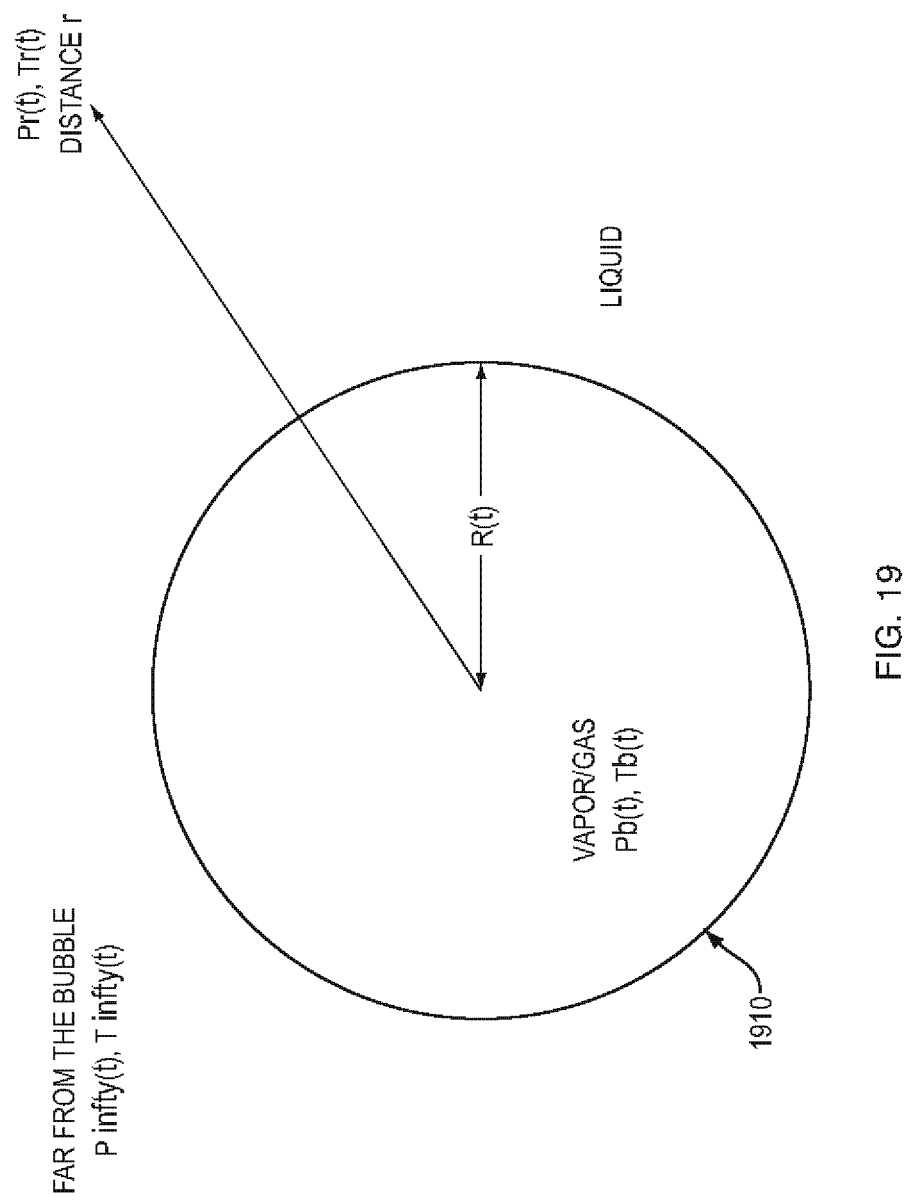
FIG. 19 is a schematic of a spherical bubble in infinite fluid.

A single bubble in an infinite domain of liquid at rest with a uniform temperature is depicted in FIG. 19. The bubble is assumed to maintain spherical symmetry, and nearby solid boundaries are ignored. Bubble dynamics with a radius R(t) and external pressure $p_\infty(t)$ at temperature $T_\infty$ is given by the Rayleigh-Plesset equation [Brennen, Christopher Earls, *Cavitation and Bubble Dynamics*, 1995, Oxford University Press]. A quasi-static case for a bubble radius ignoring all the dynamics involved at the interface is considered. The assumption would be true if the bubble is given sufficient time to evolve and is in equilibrium with the external fluid. Also any compressibility of external liquid is ignored (constant density $\rho_L$). The viscosity of the liquid is also assumed to be constant ($\mu_L$). The contents of the bubble are assumed to be homogenous and the temperature ($T_b$) and pressure ($P_b$) is considered always uniform. Finally the system is assumed to be isothermal and considered to evolve slowly.

For an isothermal compression of ideal gas, $P_1V_1=P_2V_2$. Now, when external liquid pressure at $P_\infty(t)$ changes from $P_\infty(t_1)$ to $P_\infty(t_2)$, the internal bubble pressure changes based on the ideal gas law from $P_b(t_1)$ to $P_b(t_2)$. Also, $$P_b(t_2) = P_\infty(t_2) + \frac{2\sigma_{t_g}}{R(t_2)}$$

where the radius at time $t_1$ is given by $R(t_1)$. Appling the ideal gas law:

$$\frac{P_b(t_1)}{P_b(t_2)} = \frac{R(t_2)^3}{R(t_1)^3}$$

Hence, knowing the external pressure both at time $t_1$ and $t_2$, and the bubble radius at time $t_1$, the final bubble radius at time $t_2$ can be evaluated. For a bubble of 100 μm, stable at external pressure of 10 psi and surface tension for air-liquid interface of 73 mJ/m², the change in radius for a rise of external pressure of 10 psi can be evaluated. The new radius for the bubble at 20 psi should be 96.5 μm. This is a considerable change, which is easily detected by various optical techniques.

In accordance with the present invention, a pressure sensor can be constructed using all passive no moving part integrated components in a microfluidic setup. Such a device can provide an accurate pressure reading at a precise location in a channel. This is crucial in the correct design and operation of complex microfluidic circuits, where a way of evaluating the functioning of the chip is very crucial. The device typically consists of at least one channel with at least one side channel ending in a closed form geometry. The device is fabricated in polymeric materials and the chip is sealed. With fluid (single or multiple phase) flows in the center channel, air pockets equal in size get trapped in narrow side channels. The trapped air forms a compressible pocket that is used to provide the pressure reading in microfluidic channels. By measuring the limit to which the air inside the channel has been compressed, the exact pressure in the channel can be calculated. Since the pressure sensor is a completely passive, no moving part, mechanical method of measuring pressure in complex network of channels, it is much simpler and easier to integrate in microfluid devices. The pressure sensor can also be used to study pressure drop across a bubble passing through a channel.

Figure 20:
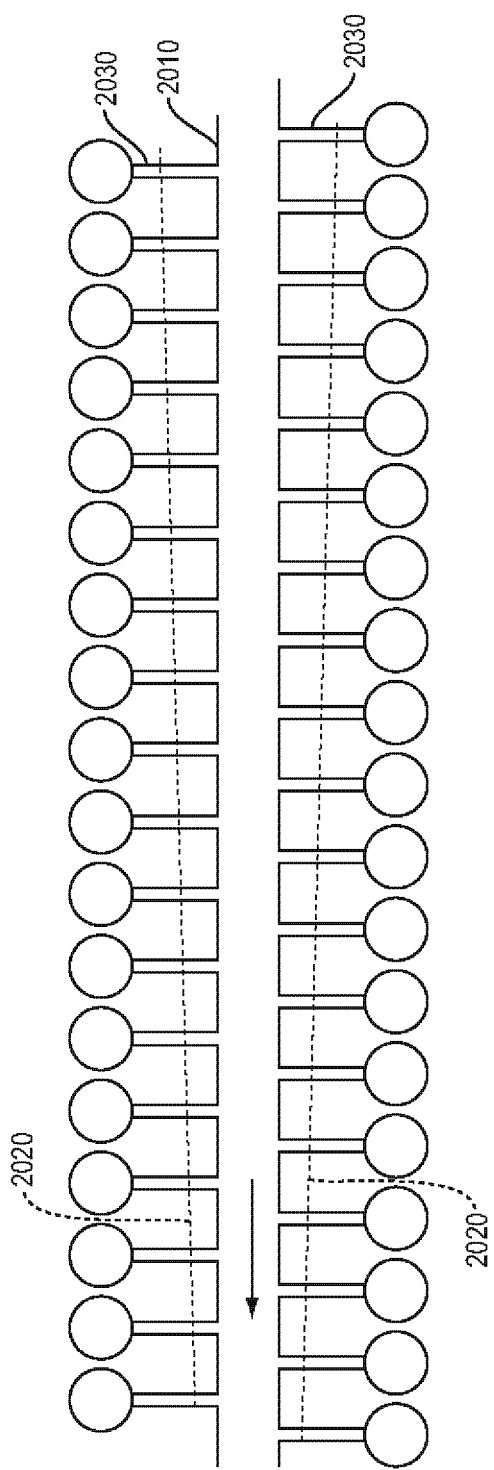
FIG. 20 depicts a bubble pressure sensor according to one aspect of the present invention.

FIG. 20 depicts one embodiment of such a pressure sensor, having the linear decrease in pressure with flow along a channel, as discussed previously. In FIG. 20, central channel 2010 has a flow from right to left. This results in gradual pressure drop from right to left in the device. This is shown by dotted lines 2020, which are formed by joining the air-water interface in all the small side branches 2030 connected to main channel 2010. Numerous variations in geometry for air channels 2030 are possible. For the embodiment of FIG. 20, the devices were fabricated by bonding multiple layers of Kapton, which is a non-porous polymer. The channel height is close to 100 microns. Due to specifically designed geometry, air is trapped inside the smaller side channels in the device when water or a liquid flows from right to the left.

Various other optical and mechanical transducers can also be constructed with the bubble logic technology of the present invention. The presence or absence of an air bubble induces a change in refractive index along an optical path. This property, along with the ability to route air bubbles through logic structures, provides the capability to produce optical transducers for, e.g., a display. The devices can also be used to regulate pressure at the output ports, thus making novel pressure induced actuators.

Fabrication and Testing.

Soft lithography is preferably employed for fabrication of the microfluidic devices of the present invention, as described in [Whitesides, George et al., "Flexible methods for microfluidics", *Physics Today*, 2001]. The fabrication steps are briefly described here, but it is understood that this is not the only method of fabrication that can be used for making the devices described in the document. Many fabrication methods exist, including, but not limited to, embossing, 3D direct writing using laser ablation, and bulk micromachining, any of which can be used for fabricating microfluidic devices. Thus the present invention is not to be limited to any particular fabrication technique.

The soft lithography technique requires negative molds of the required devices. Starting with a clean silicon wafer, a negative photoresist (SU8) is spin-coated onto it to suit the thickness of the channels required. After a pre-exposure bake, the wafer is exposed to a UV light source through a transparency mask printed on a high-resolution digital printer. The photoresist is post-baked to harden and further cross-link the resist at places where it was exposed. An SU8 developer is used to wash away unexposed resist, and the wafer is left with a negative mold of the required device. PDMS is casted off this mold to produce the required microfluidic devices. The rubber molds are further sealed off, and entry ports created. The device is wired using polymer tubing that connects to the reservoirs.

Figure 21:
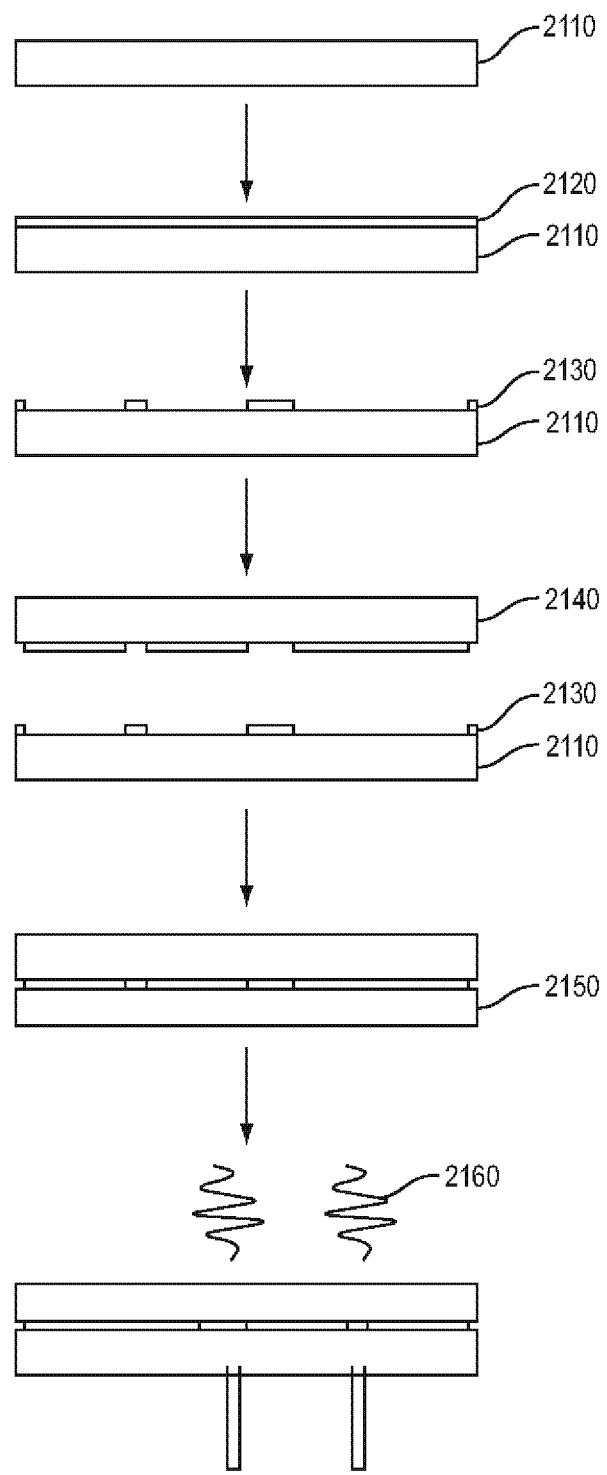
FIG. 21 depicts the elements of the process flow adopted for SU8 based soft lithography and generation of bubbles using laser pulses, according to one aspect of the present invention.

FIG. 21 depicts the steps of the process flow adopted for SU8 based soft lithography. In FIG. 21, quartz wafer (optically clear) 2110 is the substrate for spin coating of SU8 2120. The thin film is exposed to UV light to develop the substrate, creating patterned photoresist 2130. Molds 2140 in PDMS are made, which form the microchannels. The channels are sealed with quartz wafer 2150 that allows UV light to pass through. This setup is used to write bubbles inside the micorochannel geometries using laser beams 2160. Thus, bubbles can be programmatically written anywhere on the chip. For example, location-specific bubbles can be programmatically written by cavitation that is induced by very short laser pulses at 193 nm.

In an example procedure, a 4" silicon wafer (any orientation, bought from Wafernet) is first cleaned in an acetone solution to remove any dirt or dust from the surface. The wafers are dried in nitrogen to remove the solvent. A negative photoresist (SU8-2050, bought from Microchem) is spin coated onto it to suit the thickness of the channels required. Usually for a 10-20 micron channel height, the resist is spin coated for 30 seconds at 1000 rpm on a spin coater. The wafers are then pre-exposure baked at 65 deg C. on a hot plate for 40 seconds. After the pre-exposure bake, the wafer is exposed to a UV light source through a transparency mask printed from a high-resolution digital printer. The mask blocks light everywhere other than the desired features. The method employs 10 second exposures 8 times in order to avoid overheating the substrate. This causes cross-linking in the SU-8 wherever exposed. The photoresist is post baked for a minute at 65 deg C. and for 45 seconds at 90 deg C. to harden and further crosslink the resist at the places where it was exposed. An SU8-2050 developer (nanodeveloper from Microchem) is used to wash away unexposed resist, and the wafer is left with a negative mold of the required device. The mold is further washed in acetone to remove any unwanted SU-8 debris on the surface.

The microfludic devices described have been fabricated in PDMS (Poly-dimethyl siloxane) (Dow corning Sylgard 184) with PDMS curing agent (Dow Corning) in a 10:1 weight distribution. The mixture is de-gassed in a vacuum chamber to remove dissolved particles in the solution. PDMS is poured into a petri dish with the silicon mold at the bottom. The polymer is thermally set by keeping it in an oven for 2-3 hours at 65 deg C. The PDMS positive is carefully removed from the wafer and cut into die sizes. Access holes are made in PDMS mold for ports for the channels. A sharpened needle is employed to make holes in the mold. The mold is then sealed with glass slide on the top. The glass slide (Eric Scientific) and PDMS mold are kept in an air plasma (March Plasma; air flow 2 pps; power 0.9 W for 30 seconds). The mold is put on the glass slide and it self-seals to form the channels between the mold and the glass slide. Polymer Tubing (Intermed) is inserted in the mold and connected to the air/water pressure supply for testing the devices.

The device is then maintained in a test rig with a high-speed video camera (Phantom 1000 fps) for testing. The fluids used in the test setup are nitrogen and water. Research grade nitrogen gas (AirGas) is flown in the gas line, and water with small amount of surfactant (Tween 20) is flown in the liquid line. Different liquids flown in the devices have been studied to characterize viscosity effects. Optical microscopy techniques are used to gather data from the microfluidic devices.

Several devices were also fabricated using a laser ablation-based direct writing system. Glass wafers were chosen for the testing phase. Any of several different materials, including various polymers, may be selected based on various required properties. The pattern for the microfluidic device is directly machined into the glass wafer using hat top profile excimer laser pulses. Device access ports are machined using the laser itself. Multi-wafer thermal glass boding allows for 3D microfluidic networks to be created easily through this process.

Particular Drive Methodology and Instrumentation.

Pulsed pressure driving. The devices are driven using two different fluid supplies. For the case of air-water devices, an air supply and a water supply is used. The input pressure at the device ports is controlled using pressure regulators. Another technique used to provide exact input head pressure uses long capillary tubes where the weight of the fluid column provides exact pressure at the port. To provide pulsed pressure input, electric solenoid valves are used inline. Solenoid valves provide a switching pressure input to the devices that is used to produce on-demand bubble generation in microfluidic devices. The pulsing driving pressure can also be internally generated in the fluidic device itself from a fixed pressure using an oscillator like device. Ring oscillators can be easily fabricated from switching gates, as described previously, and can then be employed to drive the circuit at required frequencies. Thus, no external mechanical valves are required for the input signal. The micro-heaters used in programmable bubble modulators are driven by electronic pulse trains, 5V rail to rail, using a simple transistor circuit. Thus, in one specific embodiment, a microcontroller can be used to drive the modulator Illustrative Example Applications: Droplet Based Combinatorial Chemistry Chips.

A combinatorial system produces all the possible combinations of output compounds given a set of input compounds. Such a system is extremely useful for automating various drug and chemical discovery platforms. Micro-spotting robots have been conventionally used for various combinatorial chemistry needs. Here, several pipettes holding various reagents are mounted on a robotic platform that dispenses the reagents sequentially to perform a given combinatorial operation. Since the operation is based on a mechanical robotics platform, it is fairly expensive, with limits to resolution of micro-spotting, and hence the number of output compounds that can be produced. Several microfluidic combinatorial chemistry platforms have been proposed [Cabral, Jao T. et al., "Microfluidic combinatorial polymer research", *Polymeric Materials Science and Engineering*, (90):337-338, 2004; Watts, Paul et al., "Microfluidic combinatorial chemistry", *Current Opinion in Chemical Biology*, pp. 7380-7387, 2003; Neils, Christopher et al., "Combinatorial mixing of microfluidic streams", *Lab on Chip,* 2004; Ismagilov, Rustem F., "Microfluidic arrays of fluid-fluid diffusional contacts as detection elements and combinatorial tools", *Anal. Chem.,* (73):5207-5213, 2001]. However, previously proposed microfluidic combinatorial chips are continuous flow devices where the end product is produced as a continuous stream. The devices can only be fabricated using multi-layer 3D fabrication technologies that require exact alignment of each layer used.

Figure 22A:
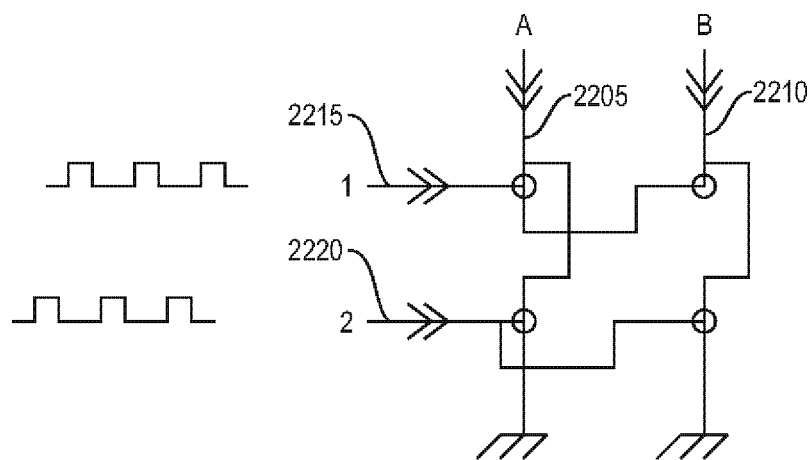
FIGS. 22A and B are example embodiments of droplet-based combinatorial chemistry systems according to one aspect of the present invention.

Based on the present invention, a single layer droplet based combinatorial chemistry chip has been implemented. The advantages include the need for fewer input reagents and extremely simple fabrication techniques. Since it is not a continuous flow system, compounds can be produced in extremely small volumes and then be processed further. On-demand droplets are produced at the inlets and then are routed inside a single layer device. The droplets can be routed and made to coalesce with other droplets, based on the device geometry and the timing of pulsed droplet generation. FIGS. 22A and B depict schematics of combinatorial production based on bubble logic devices. Since the scaling properties are independent of the number of layers in the device, simple device construction can therefore yield a large number of combinatorial compounds by employing this technique.

FIGS. 22A and B are examples of droplet-based combinatorial chemistry systems according to the present invention. Droplet-based logic control is employed to reroute droplets such that all the combinatorial possibilities are covered in a microfluidic system. For a 4×4 device, with inlets designated as A, B, C, D and 1, 2, 3, 4, the following combinations are possible:

$$\begin{bmatrix} 1,A & 1,B & 1,C & 1,D \\ 2,A & 2,B & 2,C & 2,D \\ 3,A & 3,B & 3,C & 3,D \\ 4,A & 4,B & 4,C & 4,D \end{bmatrix}$$

Figure 22B:
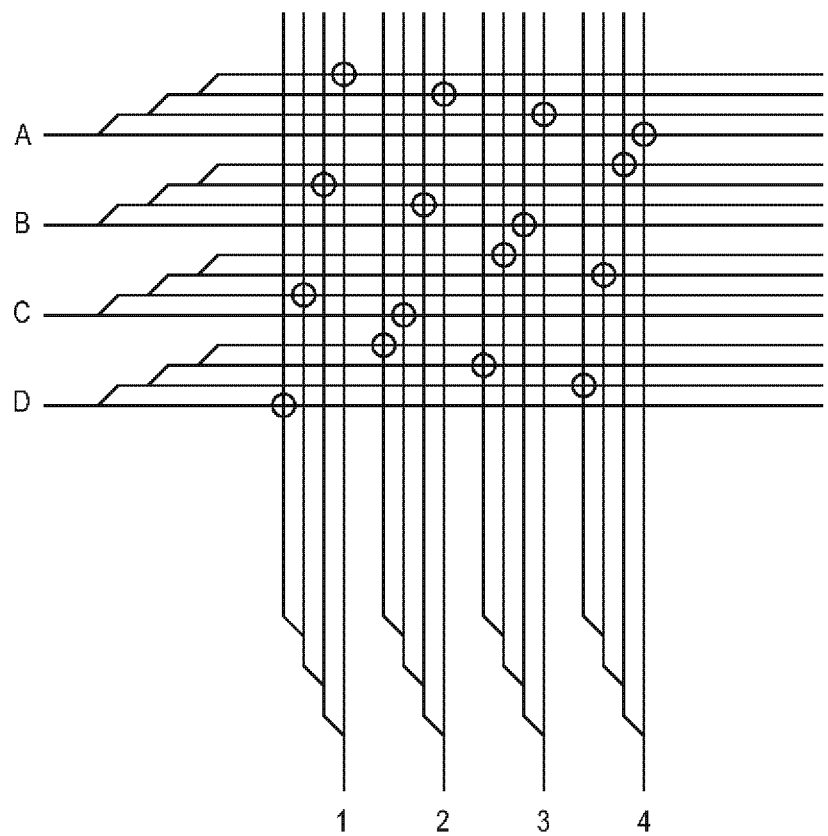

In FIG. 22A, a combinatorial circuit has two reactant inputs A 2205 and B 2210, and two control inputs 2215 and 2220. Control inputs 2215 and 2220 can be used to program the combinatorial chip, thus providing a large number of possible operations. In FIG. 22B, a larger implementation has 4 inputs and 4 control channels. By means of the present invention, it is possible to build a generic combinatorial chip for performing combinatorial operations on reactant species forming a very large set of products that can be quickly tested.

Field-Produceable Micro-Mechanical Controller.

Embedded control systems are ubiquitous in modern systems. A mechanical system being controlled can usually be broken down into its mechanical parts and logical control circuitry. Based on bubble logic devices, various control elements can be designed. An example controller might be a position controller for a multi-axis stage incorporated into a machine tool, e.g., a CNC milling machine. With a simple, single-layer fabrication process, it is possible to fabricate these controllers in the field. It is also possible to fabricate a simple micro-controller with thousands of transistors based on bubble logic technology. Such a controller can be employed as a control element for micro-mechanical systems. Based on the present invention, it is also possible to build all the components needed for a complete computer, including logic, memory, display, keyboard, and various sensors.

Droplet Based Microfluidic Control.

Emulsions in the macro world are usually non-homogenous, with a large array of droplet sizes dispersed in a continuous liquid medium. In a microfluidic system, precise micro-emulsions can be formed via various shearing forces. Many device geometries have been proposed for merging and splitting for such droplets in microfluidic systems. Due to enhanced mixing effects, controlled reaction volume, and no diffusion outside of the miniature droplet-based reaction vessel [Jensen, Klays, "The science & applications of droplets in microfluidic devices", *Lab on Chip*, (4):31-32, 2004], such droplet based microfluidic systems are ideal for implementing programmable reaction networks. The benefits of droplet based microfluidic systems have been demonstrated in various systems.

Effective and flexible control systems play an extremely important role in scalable microfluidic systems [Thorsen, Todd et al., "Dynamic pattern formation in a vesicle-generating microfluidic device", *Physics Review Letters,* 86(18): 4163-4166, April 2001]. This is clear from the extensive use of multi-layer soft lithography based embedded valves reported in numerous microfluidic applications. Though droplet based microfluidic systems have numerous advantages over traditional microfluidic systems, they still lack a scalable control strategy for manipulating droplets inside microchannels. Two strategies currently employed for manipulating droplets in microchannels can be categorized as active and passive [Jeong, Ki-Hun et al., "Tunable microdoublet lens array", *Microstructure Devices,* 2004] control.

Active control [Srinivasan, Vijay et al., "An integrated digital microfluidic lab-on-a-chip for clinical diagnostics on human physiological fluids", *Lab on Chip*, (4), May 2004; Gascoyne, Peter R. C. et al., "Dielectrophoresis-based programmable fluidic processors", *Lab on Chip*, (4):299-309, July 2004] of droplet based systems employs a dense microelectrode array with programmed electric fields that create dielectrophoretic and electrowetting forces used to manipulate these droplets. With the rising complexity of fluidic devices, such a control becomes fairly complex. Also, since the droplets are forced to move on a surface, some benefits which are obtained from purely liquid suspended emulsions are lost (due to surface droplet interactions). Passive control [Jeong, Ki-Hun et al., "Tunable microdoublet lens array", *Microstructure Devices,* 2004] of droplets can be used to merge, split [Chronis, Nikolas et al., "Tunable liquid-filled microlens array integrated with microfluidic network", *Optics Express,* 2003] and sort droplets based on local geometries. Such a system lacks the programmability and flexibility which exists in micro-electrode based control systems.

The present invention includes an all-fluidic active control scheme for droplet-based microfluidic systems. As compared to a constant pressure-driven flow, a pulsating pressure field (analogous to a microprocessor clock) is used to drive bubbles in microfluidic shift registers. This provides a precise temporal and spatial control that is obtained only in micro-electrode array based droplet systems. Rather than passive control elements based solely on geometry, the present invention employs bubble-bubble interaction as a control mechanism. For example, a bubble in one channel can control the path or motion of another bubble. The principle of "path of least resistance", in which a bubble takes a path that has a least interfacial energy barrier, is utilized to design various control gate geometries.

Multiplexer Circuits.

Figure 23:
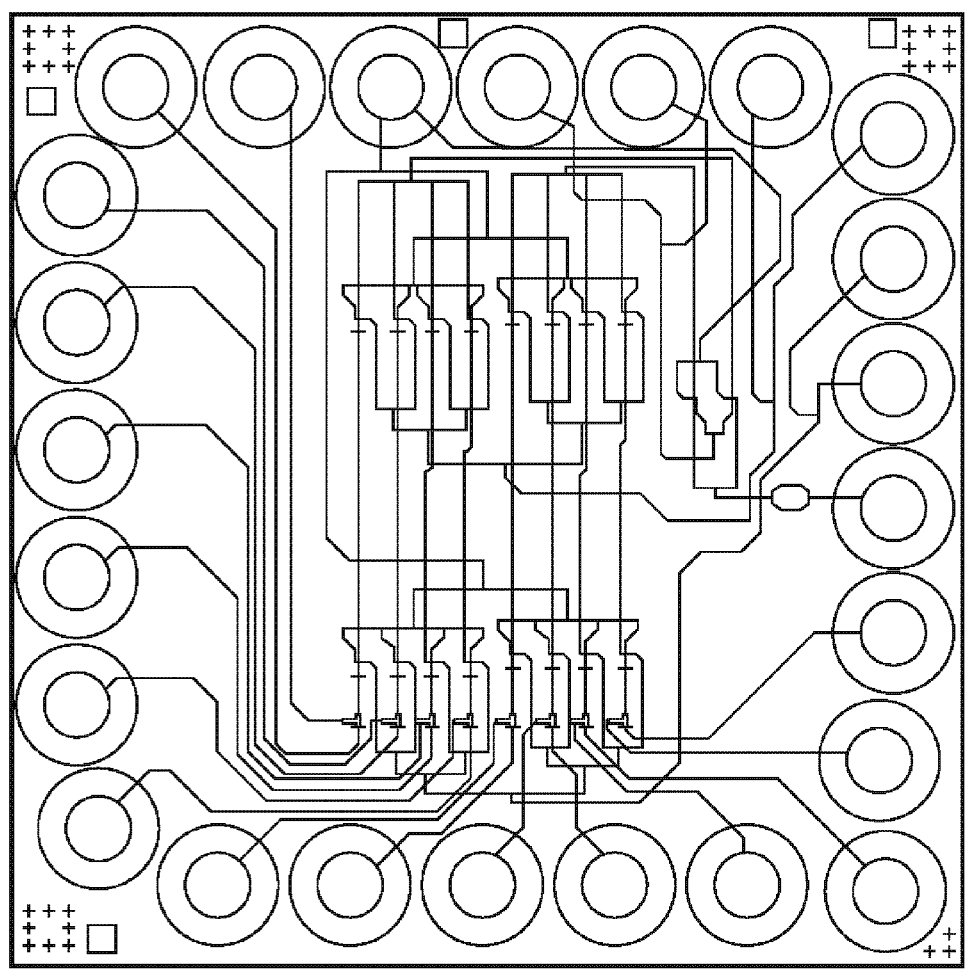
FIG. 23 depicts a multiplexer circuit created from bubble-logic devices according to one aspect of the present invention.

FIG. 23 depicts a multiplexer circuit created from bubble-logic devices. The scheme consists of a 2-stage 8:1 hierarchical bubble multiplexer. The chip can be used to regulate multiple input channels (8 in the above example) using log n (log based 2) control lines. In FIG. 23, the black lines consist of microchannels. The chip can be used as a module in general purpose microfluidic chip. The chip consists of two identical 4:1 multiplexer stages that each take 4 inputs. Two outputs from the 4:1 multiplexers connect into a 2:1 multiplexer with 2 inputs and one output. Thus, the chip is designed in a modular fashion by reusing the fluidic components.

Figure 24:
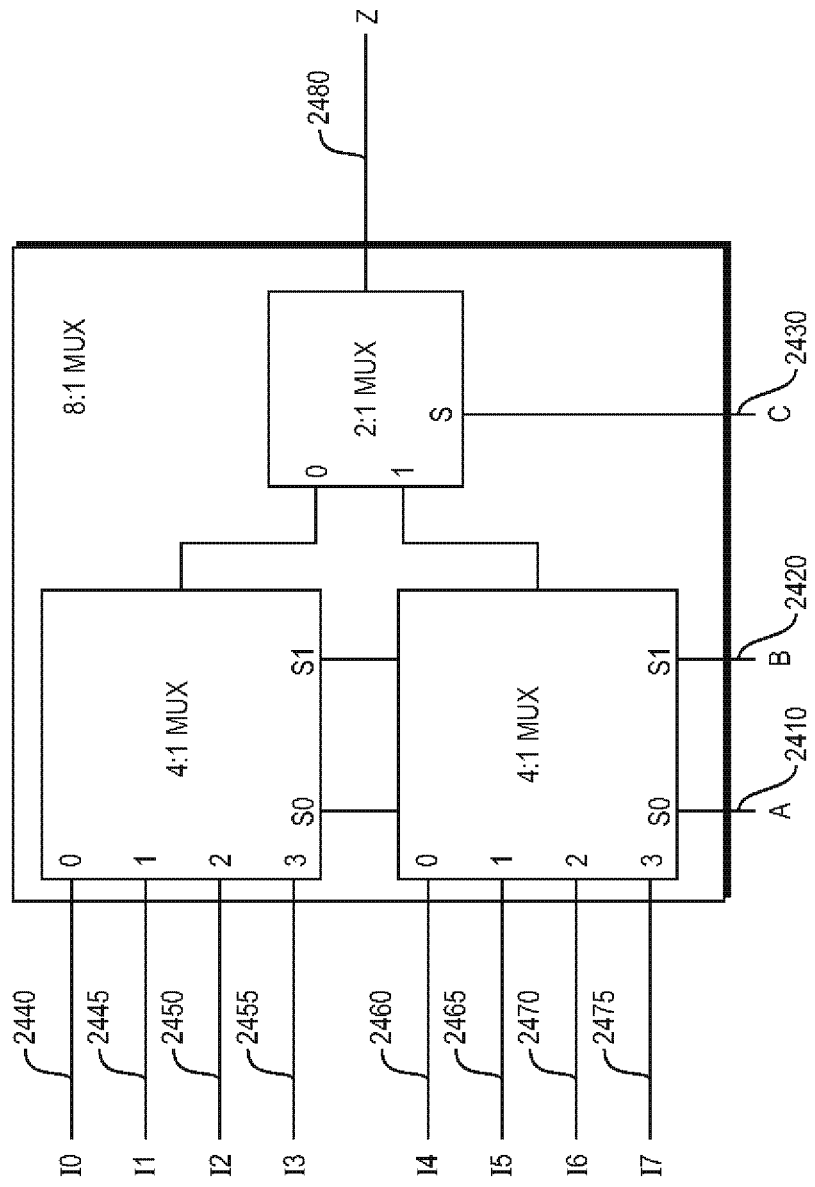
FIG. 24 is the electronic device equivalent of the circuit of FIG. 23.

FIG. 24 is an all-fluidic hierarchical multiplexer implemented in two stages. The multiplexer consists of three fluid input control lines A 2410, B 2420, C 2430 that carry input bubbles and eight other input lines 2440, 2445, 2450, 2455, 2460, 2465, 2470, 2475 with one output line 2480. The multiplexer connects one of the eight input lines into the output line based on the control sequence. Implementation of the multiplexer is possible because of cascading of different logic gates. The device can be used to control a large number of input channels containing droplets using a small number of control channels. Thus, an input bubble/droplet stream from any of the 8 inputs can be directed to the output based on the bubble sequence at A, B and C. The circuit shown is a reusable module in a general-purpose microfluidic device. FIG. 24 demonstrates that cascaded logic gates that can be put together to form complex circuits according to the present invention.

Bubble-Based Displays.

Technology to control the movement of bubbles in microgeometries can be used to build bubble-based displays. The optical transmission properties of a bubble vary from the surrounding fluid that encloses it. Various optical techniques can thus be used to make all-bubble displays, where a pixel is represented by the presence or absence of a bubble. The bubbles can be controlled using the previously described bubble logic machinery. Thus, non-volatile display and projection devices can be formed with no-moving parts. This is strikingly different than the projection devices used currently, which employ moving digital mirrors to project and display images.

FIG. 25 is an example of an electrically programmable bubble modulator employed as a display element. In FIG. 25, programmable bubble generator 2510 is followed by serpentine channel 2520. Bubble generator 2510 produces a programmed sequence which forms the required pattern in serpentine channel 2520. This can be used to form a representation of a digital image in serpentine channel 2520. This is only one embodiment of a bubble display; various other embodiments where the bubbles interact with light in different forms to create a display device is also possible. As described previously, in one embodiment the modulator consists of a funnel-shaped channel at the junction of an air/water interface with an embedded platinum heater in the channel. By modulating the surface tension and pressure at the interface, a programmed sequence of bubbles can be produced in a microchannel. For the particular embodiment shown, the modulator is driven by an electrical signal via a heater. Other modulating elements, such as pressure transducers and light-based modulation are also possible. Since the frequency of the modulated bubble generator is in kHz, it is very simple to run the device much faster than the refresh rates required for most display applications. Various other configurations of a channel with a series of bubbles interacting with light to produce a display are also possible.

Bubble-Based Actuators and Control.

Figure 26:
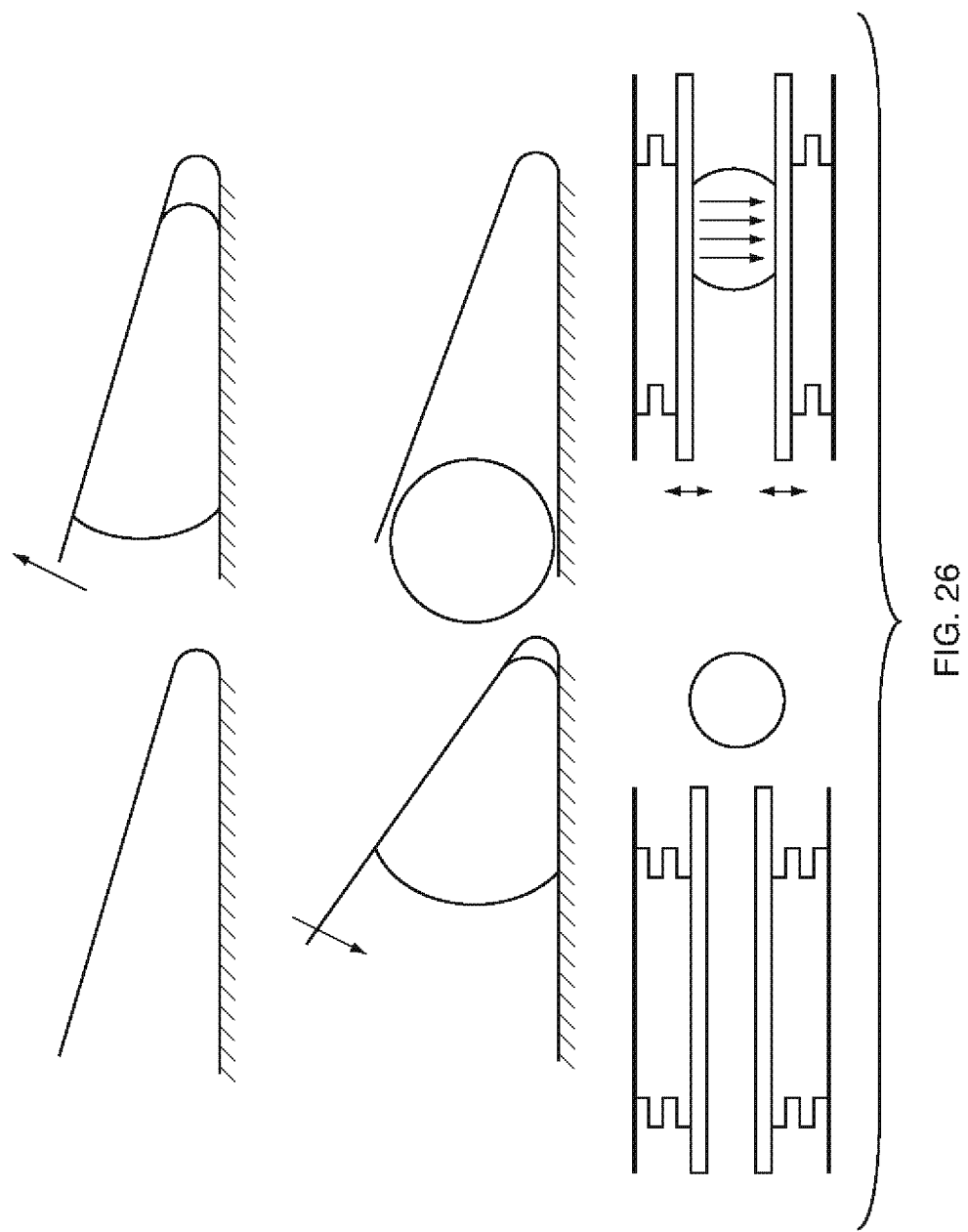
FIG. 26 depicts several configurations of flap actuators that use bubbles as an actuating scheme, according to one aspect of the present invention.

Conventionally, micro-actuators are controlled using high electric fields and electromagnetic phenomena. On/off mechanical moving parts valves actuated by thermally-generated bubbles have been proposed. Various micro-mechanical actuators can be controlled using the present invention. Thus, bubbles are not only information carriers in bubble logic devices, they can also be employed to actuate micromechanical structures. This provides a direct scheme to convert control signals from bubble logic devices into mechanical motion. FIG. 26 depicts several configurations of flap actuators that use bubbles as an actuating scheme.

Previous fluid logic demonstrations at low reynolds have several shortcomings that the present invention does not. They used non-newtonian fluids, with non-linear flow properties. The present invention uses only newtonian liquids, thus there is no limitation on the implementation. Previous logic families use an external switching element like a solenoid, which only can switch at around 50 Hz. The logic elements of the present invention can switch at a ~1000 Hz, couple of orders of magnitude faster than previous devices. The system of the present invention is completely scalable to large and complex microfluidic droplet/bubble circuits because logic gates may be cascaded (input and output signals have the same representation), because fan-in and fan-out can be provided in the circuits, and because there is a provision for gain so that a smaller bubble can cause switching of a larger bubble. Currently, there are limitations in providing input to microfluidic chips, as it must be provided serially using valves based on solenoids located outside the chip. However, with the increasing complexity of chips, more and more information needs to be input into the system, resulting in a bottleneck. In the present invention, information can be sent serially on multiple bubble modulator lines. Thus, the chip can be programmed based on an applied sequence of bubbles/droplets.

Microscopic bubbles traveling in complex fluidic networks exhibit rich nonlinear dynamics. Pressure-driven flow behavior of bubbles in an interconnected microfluidic network can be described using a simplified dynamic flow resistance model [F. Jousse, G. Lian, R. Janes, J. Melrose, *Lab Chip* 5, 646 (2005)]. Single phase flow resistance of a channel at low Reynolds number can be approximated as $\Delta p/Q = \mu L/h^3 w$, where $\Delta p/LQ$ is defined as the hydraulic resistance per unit length, $\mu$ is dynamic viscosity, and h and w are the height and width of the microchannel. The presence of a bubble in a channel drastically increases this flow resistance. The pressure drop due to a long bubble flowing in a channel, where the bubble radius in an unbounded fluid is greater than the channel width and the continuous phase completely wets the channel surface, is nonlinear and is proportional to $\Delta p = \sigma/w (3 Ca^{2/3})$ [F. P. Bretherton, *J. Fluid. Mech.* 10, 166 (1961), H. Woong, C. Radke, S. Morris, *J. Fluid Mech.* 292, 95 (1995)], where Ca is the Capillary number ($Ca = \mu u/\sigma$), $\mu$ is the dynamic viscosity, u is the flow velocity of the continuous phase, w is the channel width and $\sigma$ is the surface tension between liquid and gas phase. For small flow rates this increased flow resistance is primarily due to viscous dissipation in the thin film of liquid surrounding the bubble. With the presence of surfactant molecules on the air-water interface, viscous dissipation in the lubrication film further increases due to the no-slip boundary conditions at the interface. In this case, the pressure drop across a finite length bubble is also linearly dependent on the bubble length until it reaches a critical value, beyond which it is constant [C. W. Park, *Phys. Fluids* 4, 2335 (1992)]. When a bubble traveling in a microchannel arrives at a bifurcation with low Capillary number (where the bubble does not split due to surface tension dominating the viscous stress), it chooses the branch with highest instantaneous flow [D. Link, S. Anna, D. Weitz, H. Stone, *Phys. Rev. Lett.* 92, 054503 (2004)].

With an increased flow resistance due to the presence of a bubble in a micro-channel, flow lines in surrounding interconnected channels can be perturbed. These perturbations can hence be used to route another bubble stream resulting in hydrodynamic interactions between bubbles. Navier-Stokes equations describing low Reynolds number flow are linear due to negligible inertial terms. Nonlinearity in such a system arises from the introduction of interfacial force terms from the boundary conditions due to the presence of a free surface at the fluid interfaces [T. Thorsen, R. W. Roberts, F. H. Arnold, S. R. Quake, *Phys. Rev. Lett.* 86, 4163 (2001)]. Such nonlinear time-dependent interactions are the basis of the bubble logic gates of the present invention. The present invention exploits such interactions to build AND, OR, and NOT gates, forming a universal Boolean logic set. Since bubbles are neither produced nor destroyed during a bubble logic operation, the number of bubbles is conserved from input to output for a given device. In the preferred implementation described, water is employed as the liquid media (with added surfactant 2\% w/w Tween 20) and nitrogen is used for the bubbles. Planar bubble logic devices have been fabricated in PDMS (poly-dimethyl siloxane) using single-layer soft-lithography and plasma bonding to Pyrex substrates.

Figure 27A:
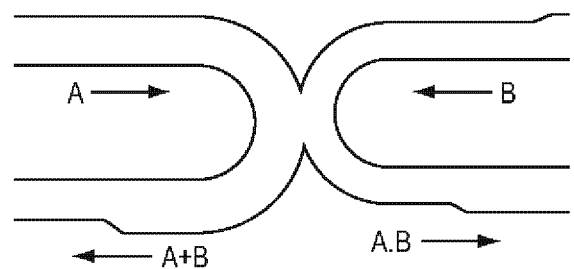
FIGS. 27A and B depict an AND/OR bubble logic gate that evaluates both AND and OR simultaneously, according to one aspect of the present invention.
Figure 27B:
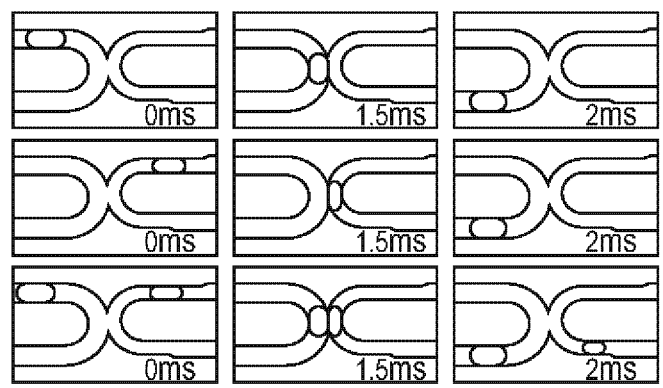
FIG. 27C depicts the bubble logic AND-OR gate time series, obtained from high-speed video, for the gate of FIGS. 27A and B.
Figure 27C:
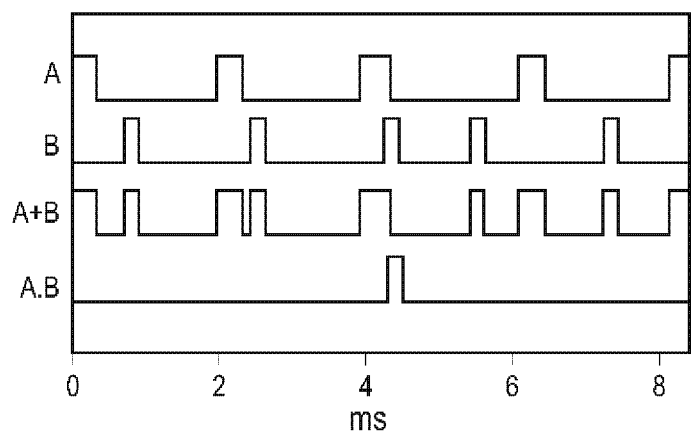

FIGS. 27A and B depict an AND/OR bubble logic gate that evaluates both AND (.) and OR (+) simultaneously, which is necessary to satisfy bit conservation. FIG. 27A is a micrograph of a bubble logic AND-OR gate with arrows depicting the direction of flow. FIG. 27B depicts a bubble logic AND-OR gate in operation for various values of A and B. FIG. 27C depicts the bubble logic AND-OR gate time series for 8 ms obtained from high-speed video. In FIGS. 27A and B, a bubble in a channel represents a bit. A and B mark the T-junction bubble input ports to the devices (planar 2D geometry, channel height 70 µm) which are driven by a constant water input flow (with 2\% w/w Tween 20 surfactant) via syringe pumps (Kent Scientific) and constant pressure driven nitrogen ($P\_0$=0.5 psi). FIG. 27A and B depict a two-input AND-OR gate with symmetric input channels marked A and B (both 50 µm wide) and asymmetric output channels (marked A+B, 65 µm wide and A.B, 40 µm wide), computing both AND and OR simultaneously. Scale bar 100 µm. Gate propagation time delay is 2 ms at an input flow rate of $Q\_A=Q\_B$=0.25 µl/sec. In FIG. 27C, a signal time trace for the device is shown for a period of 8 ms.

In FIGS. 27A and B, a single bubble arriving from either A or B at the junction will choose the wider channel, corresponding to A+B. When bubbles arrive from both A and B simultaneously, both output channels contain a bubble, evaluating both A+B and A.B. The bubble arriving earlier at the junction always enters A+B (the wider channel, with less resistance) increasing the output flow resistance of A+B, thus directing the bubble arriving later to A.B. As shown in the time trace for all four channels of the device, the two bubbles interact only if they arrive within a window $\tau\_0$ (for this gate, $\tau\_0$~0.5 ms at Q=0.25 µl/sec) determined by the residence time of the bubble in the gate geometry. No bubble coalescence was observed in the channels, because of the stabilization of the interface by surfactant molecules.

Figure 28A:
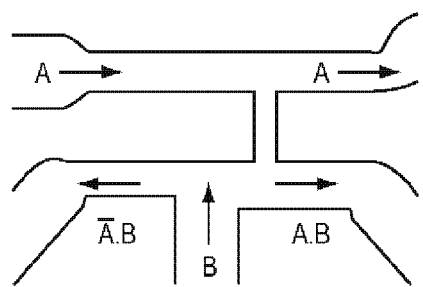
FIGS. 28A and B depict an AND-NOT gate and an AND-NOT gate in operation, respectively, according to one aspect of the present invention.

FIGS. 28A and B depict a NOT gate and an AND gate implemented with the same geometry as a universal switch gate, evaluating NOT(A).B and A.B. The device consists of two counteracting asymmetries, a T-junction (100 µm wide channel input, 50 µm and 65 µm wide channel outputs) and an offset inlet channel (25 µm wide) that provides variable flow from the top control channel (50 µm wide). Scale bar 100 µm. A bubble in the control channel (bubble size r_c) significantly reduces the inlet flow, switching the direction of the bubble at the T-junction (bubble size r_t). Gain is defined as r_t/r_c=1.2 ($Q\_A=Q\_B$=0.92 µl/sec. Propagation delay time is 7 ms.

Figure 28B:
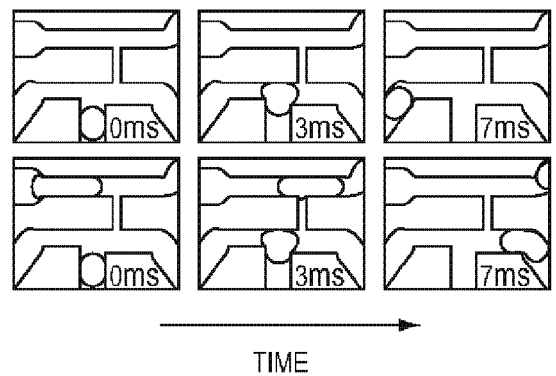

In any logic family, fan-out is necessary for the output signal from one gate to act as an input signal to multiple gates. In the case of bubble logic, this can be simply implemented by splitting bubbles at a T-junction [D. Link, S. Anna, D. Weitz, H. Stone, *Phys. Rev. Lett.* 92, 054503 (2004)] into equal parts. Gain is therefore necessary to restore signal levels (where the signal is represented by the bubble size) in a logic family. Gain is defined as the ratio of the volume of the output bubble to the volume of control bubble. FIGS. 28A and B depict a switching gate that implements a NOT and an AND gate simultaneously, with gain where a small control bubble can switch the output flow direction for a larger bubble. In FIG. 28A, the gate computes A.B and (NOT(A)).B simultaneously. FIG. 28B depicts an AND-NOT gate in operation, where a small bubble switches direction of a larger bubble depicting amplification or gain. A NOT gate is implemented as a NOT (A).B gate where the value of B can be set to 1 by applying a constant frequency bubble train. The switching gate consists of two counteracting asymmetries, an input channel with an asymmetric T-junction (bottom) and a narrow stream of injected flow from the control channel (top) into the wider of the two bifurcations. By introducing a bubble in the control channel, injected side flow can be dynamically turned on and off, and hence control the direction of flow of the output bubble arriving at the bifurcation.

Figure 29:
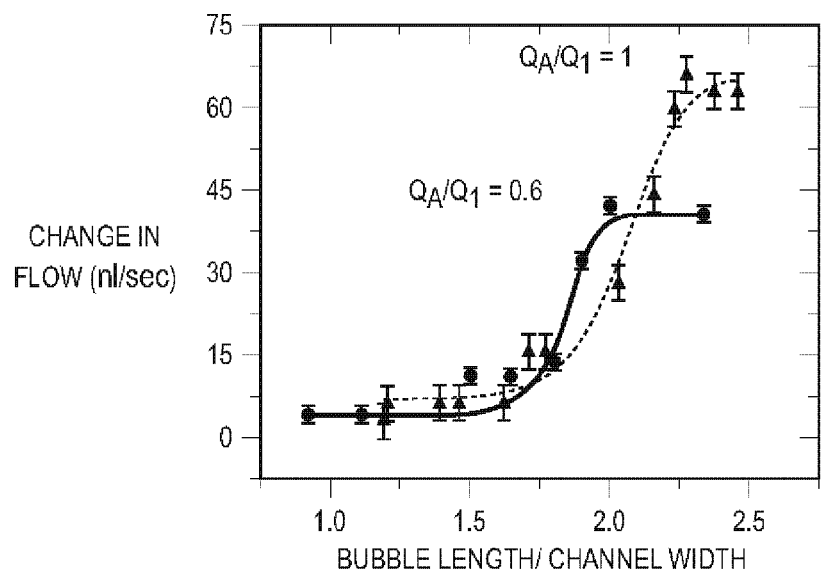
FIG. 29 is a plot of change in flow against dimensionless bubble size, depicting gain for numerous configurations of flow rates.

The change in injected flow from the control channel (Delta Q) when a bubble passes through the control channel is non-linearly related to the size of the bubble. FIG. 29 is a plot of change in flow against dimensionless bubble size (bubble length/channel width), depicting gain for numerous configurations of flow rates. This nonlinearity is used as a gain mechanism, allowing a smaller bubble from A to switch a larger bubble coming from B. Maximum change in inlet flow as a bubble passes through the control channel is shown against dimensionless bubble size (bubble length/channel width), depicting a sharp nonlinearity and saturation with increasing bubble size.

Figure 30A:
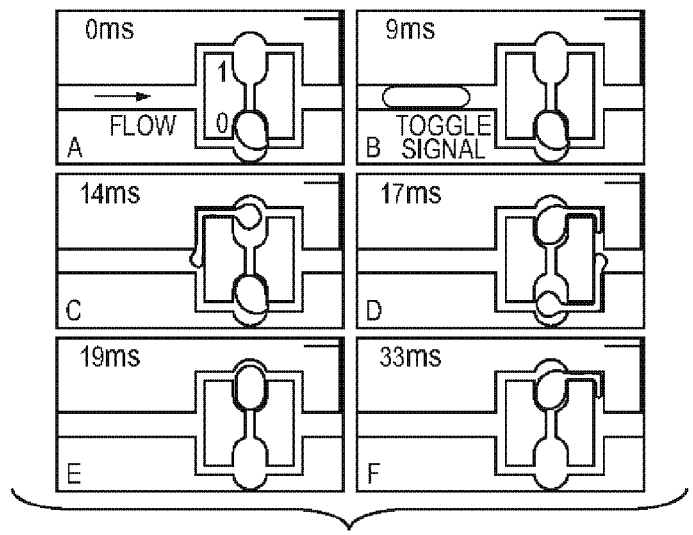
FIG. 30A depicts a microfluidic toggle flip-flop in operation, according to one aspect of the present invention.
Figure 30B:
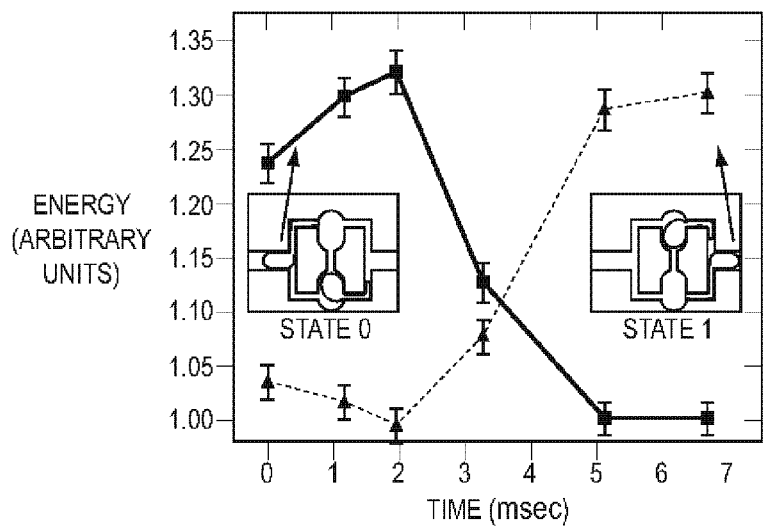
FIG. 30B depicts surface energy curves for bubbles traversing the flip-flop geometry of FIG. 30A.

Segmented-flow reactors often operate at kilohertz frequencies, where the limiting factor for high-throughput screening is the rate of information extraction from individual droplets due to slower measurement processes. In one aspect of the present invention, a bistable mechanism capable of on-demand trapping and release of individual bubbles, has been implemented as a toggle flip-flop. This implementation demonstrates the basic unit of memory in bubble-logic. A bubble minimizes its surface energy by adopting a shape with the smallest surface area. The toggle flip-flop geometry (FIG. 30A) presents an incoming bubble with two elliptical lobes where the surface energy of the bubble is at its minimum, as shown in the plot of energy vs. time (FIG. 30B). This geometry acts like a fluid dynamic bistable trap for a single bubble traveling at low Capillary and Reynolds numbers FIG. 30A depicts a microfluidic toggle flip-flop in operation. The arrow marks the direction of flow. In FIG. 30A, a toggle flip-flop with one bit memory stores a bubble (A) indefinitely against a constant flow (Q=0.25 µl/sec water with 2% w/w Tween 20, driven by a syringe pump, Kent Scientific) in an energy well until a toggle signal arrives (B). The stored bubble is released from the trap while the arriving bubble is simultaneously captured in the opposing lobe, hence toggling the state of the device (C-F). The switching time for the device is 8 ms with an update rate of 30 Hz. The capillary number Ca for given flow rate is 0.013. The device consists of a planar geometry (channel height 70 μm) with two lobes (200 μm wide, 300 μm long) connected via a pressure feedback channel (50 μm wide, 50 \μm long) and a T-junction at inlet and outlet (50 μm wide). Scale bar 100 μm.

FIG. 30B depicts surface energy curves for bubbles traversing the flip-flop geometry. The curve depicts bi-stability that is necessary for building memory gates. In FIG. 30B, the change in free surface energy of the bubble [E-calc] depicting two energy minimas for a single flip-flop event. A toggle signal arrives from the right with an elongated shape with higher surface energy (solid line) while the bubble stored in the device occupies a lower energy state (dashed line). As the toggle bubble expands to find its minimum energy state in the upper lobe, pressure from the feedback and the input channel increases pushing the stored bubble into an elongated higher energy state into the outlet channel (dashed lines). This further stabilizes the toggle bubble by rerouting flow through the empty lobe.

Figure 30C:
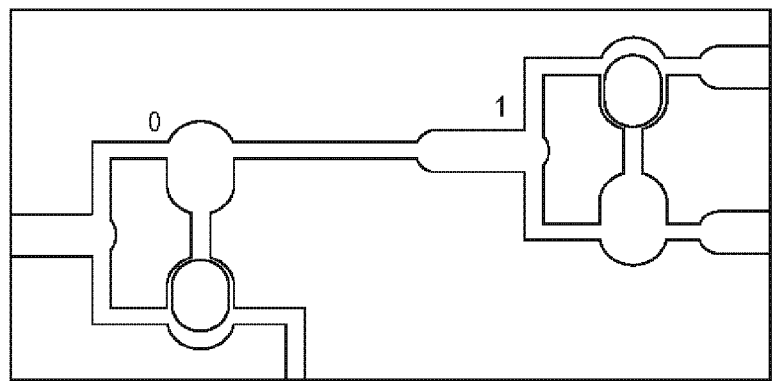
FIG. 30C depicts a ripple counter built by cascading a series of toggle flip-flops, according to one aspect of the present invention.

A two-bit cascaded ripple counter has been demonstrated by connecting toggle flip-flops in series. FIG. 30C depicts a ripple counter built by cascading a series of toggle flip-flops. Toggle flip-flops can be cascaded to build a ripple counter that updates its state on every 1 to 0 transition.

Figure 31A:
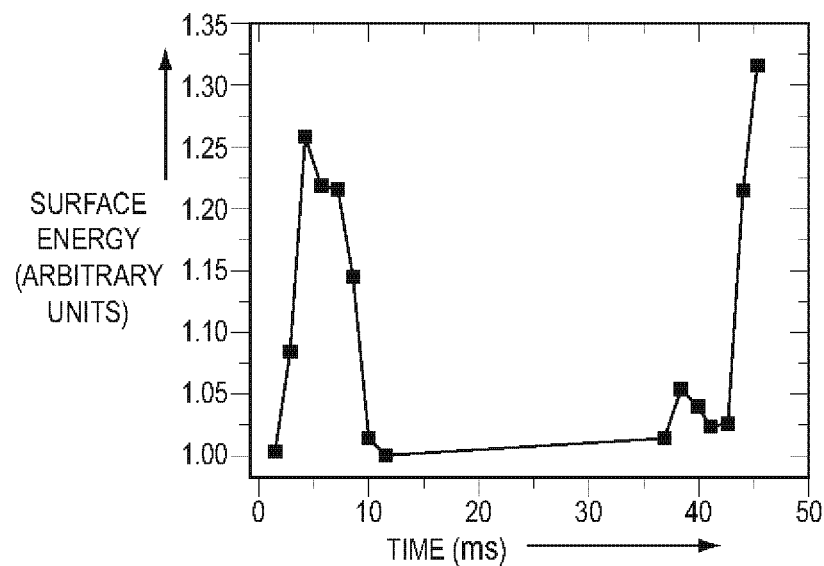
FIG. 31A is a surface energy plot for a single bubble traversing the toggle flip-flop geometry of FIG. 30A vs. time.
Figure 31B:
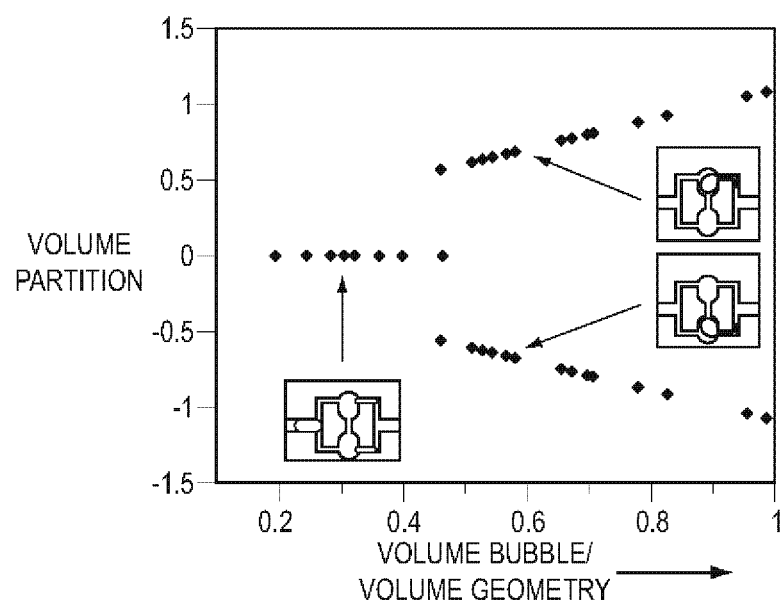
FIG. 31B is a bifurcation diagram for the toggle flip-flop geometry of FIG. 30A depicting a sudden transition from bubble breakup to the onset of bistablity.

FIG. 31A is a surface energy plot for a single bubble traversing the toggle flip-flop geometry vs. time. The large minima in the middle refers to the minimum energy well formed at the two lobes. FIG. 31B is a bifurcation diagram for the toggle flip-flop geometry depicting a sudden transition from bubble breakup to the onset of bistablity. The difference in bubble volume in the two lobes (volume partition of the bubble) is plotted against non-dimensional size of input bubble. All input bubbles considered in the dataset are longer than Rayleigh-Plateau breakup criteria for a T junction ($l/w > \pi$, l is length and w is width of the bubble). The bifurcation from equal bubble breakup to bistable mode occurs sharply. The device also showed no dependence on arrival frequency of bubbles at a junction.

The energy landscape of a single bubble traversing the bistable geometry (FIG. 31A) depicts a minimum energy well required for bistability. In this representation, the bubble in the lower lobe represents state 0 and the bubble in the upper lobe represents state 1. A toggle event occurs when a bubble arriving from the input flips the state of the device from 0 to 1 and vice versa. The device holds a single bubble indefinitely until another toggle signal arrives at the inlet T-junction. Though the incoming bubbles are much longer than the Rayleigh-Plateau criteria for breakup ($l/\pi w > 1$ where l is length of the bubble and w is the width) at a T-junction [D. Link, S. Anna, D. Weitz, H. Stone, *Phys. Rev. Lett.* 92, 054503 (2004)], the presence of a bubble in the flip-flop ensures the bubble travels to a single lobe without breakup (see bifurcation diagram, FIG. 31B). The interconnecting channel allows flow between the two lobes, necessary to dislodge a trapped bubble once a toggle bubble arrives. The repeatability of this device was demonstrated via plotting a signal trace for the device for a period of 12 seconds. Bistability also allows construction of sequential circuits including counters and memory arrays.

To provide an electronic interface to bubble logic devices, a thermal electro-bubble modulator capable of generating bubbles on demand and synchronized to an electric pulse was developed. Methods for high-frequency continuous production of mono-dispersed microbubbles and droplets in microfluidic devices have been extensively studied [T. Thorsen, R. W. Roberts, F. H. Arnold, S. R. Quake, *Phys. Rev. Lett.* 86, 4163 (2001), P. Garstecki et al. *Appl. Phys. Lett.* 85, 2649 (2004), T. Ward, M. Faivre, M. Abkarian, H. Stone, *Electrophoresis* 26, 3716 (2005)]. Electro-generation of on-demand single aqueous droplets [M. He, J. S. Kuo, D. T. Chiu, *Appl. Phys. Lett.* 87, 031916 (2005)] requires high on-chip electric fields of the order of ~1 kV. The thermal electro-bubble generator used employs an integrated micro-heater and modified flow-focusing geometry, operating at low voltages (21V). For the case of pressure-driven flow, a static force balance exists at the air-water interface with the pressure force being balanced by capillary and viscous stresses at the interface. This static balance can be written as $\Delta P + \tau\_v = Ca^{-1} k$ [T. Ward, M. Faivre, M. Abkarian, H. Stone, *Electrophoresis* 26, 3716 (2005)] where Delta P is the difference in pressure, $\tau\_v$ is the viscous stress, and k represents the mean curvature. An applied temperature pulse reduces the surface tension σ at the air-water interface. This lowers the curvature force and the pressure differential across the interface, allowing a gas filament to penetrate the liquid, which breaks to form a single bubble.

Figure 32A:
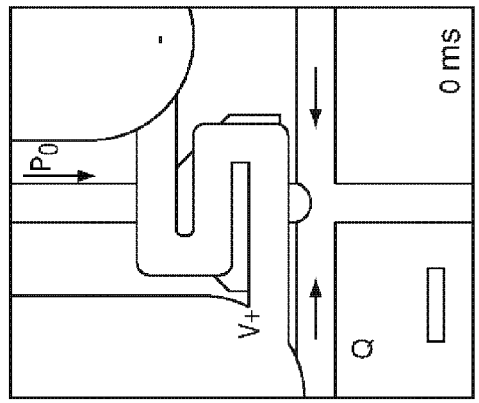
FIGS. 32A-F depict a programmable on-demand electrothermal bubble generator, according to one aspect of the present invention.
Figure 32B:
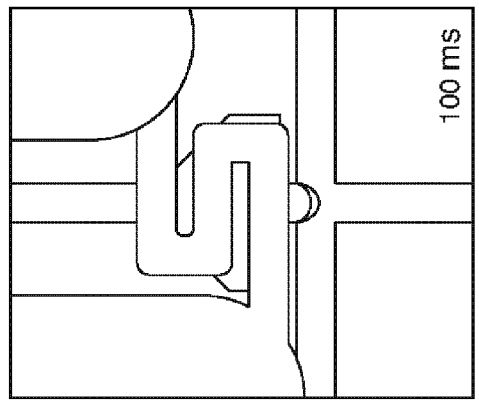
Figure 32C:
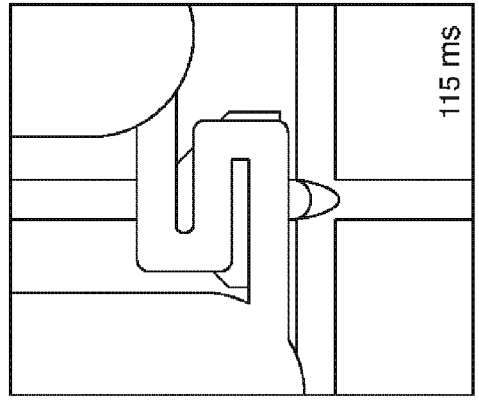
Figure 32D:
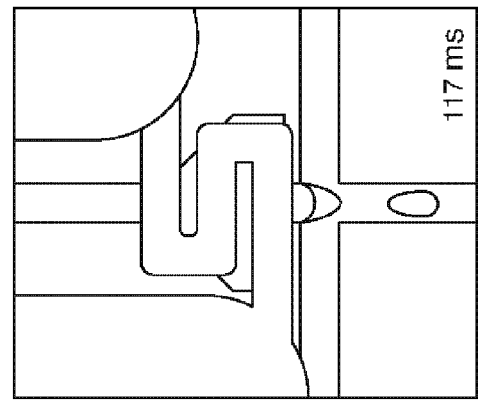
Figure 32E:
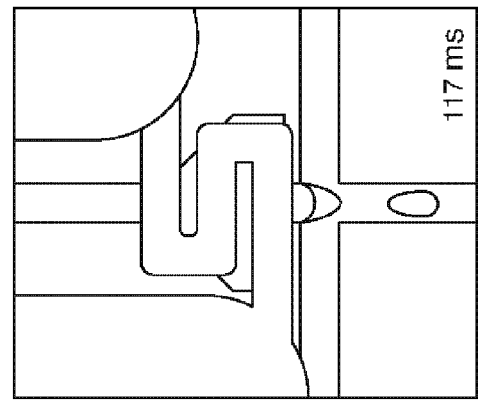
Figure 32F:
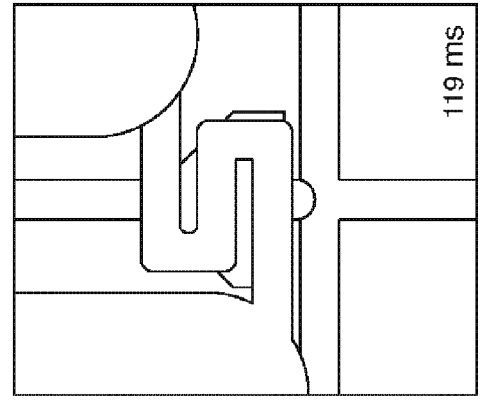

FIGS. 32A-F depict a programmable on-demand electro-thermal bubble generator. The device consists of a 50 μm wide platinum micro-heater (R=95\Omega, 200 nm thick platinum) followed by a 2 μm silicon dioxide dielectric barrier. The heater is embedded below a modified, planar flow focusing geometry (channel height 70 μm, gas inlet orifice 70 μm with a 400 μm expansion before the orifice) which pins the air-water interface, making it stable. The device is driven by a constant flow Q=0.83 μl/sec of water (with 2% w/w Tween 20) and a constant pressure supply P_0=5 psi of nitrogen. The series of photomicrographs depict a single bubble generated at a frequency of 1 Hz. Scale bar is 100 μm. A 21V DC electric pulse is applied to the micro-heater in the first 100 ms of the sequence resulting in a growth period of the meniscus (FIGS. 32A and C). Temperature-induced change in surface tension of water lowers the capillary force allowing a gas filament to penetrate the water (FIG. 32D). The narrow entrained filament (FIG. 32E) breaks into a single drop via flow focusing [P. Garstecki et al., *Appl. Phys. Lett.* 85, 2649 (2004)]. The filament retracts back very quickly due to sharp curvature at the tip (FIG. 32E) and the interface is stabilized again (FIG. 32F). Total time duration of the breakup process followed by a relaxation period is 25 ms.

Figure 33:
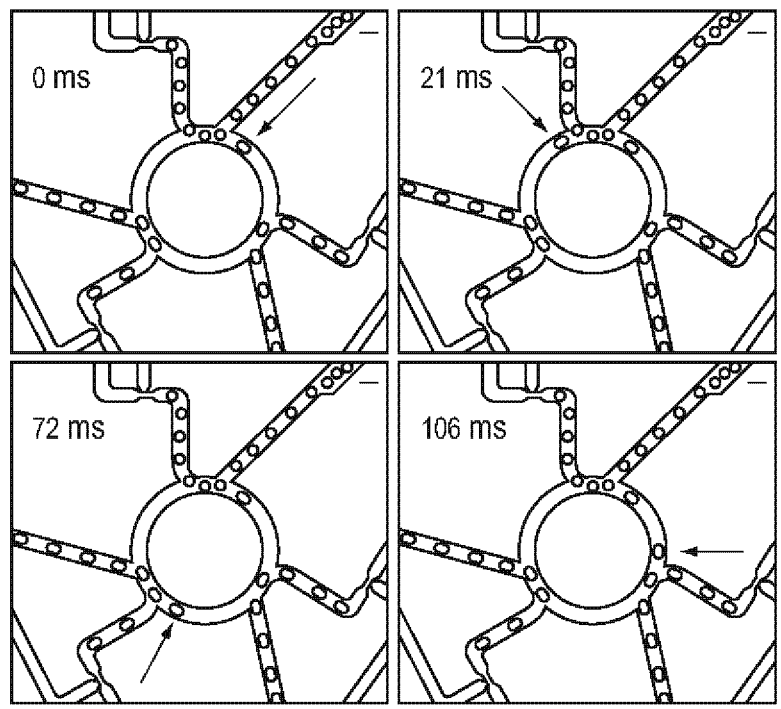
FIG. 33 depicts a ring oscillator in operation, showing bubbles oscillating in a ring configuration, according to one aspect of the present invention.

The usefulness of any logic family depends on cascadability, in order to implement an arbitrary Boolean logic function as a sequence of logic gates. For implementation of a complex close-loop control, feedback is necessary. To show cascading and feedback, a tunable microfluidic ring oscillator was demonstrated, as is common for the characterization of any new logic family. The oscillator consists of three identical AND gates connected via three identical delay lines in a ring structure (FIG. 33). Constant frequency T-junction bubble generators act as inputs to the ring oscillator providing a constant stream of bubbles. A bubble propagating from the ring delay line (FIG. 33, white arrow), increases the resistance of the outgoing channel when it arrives at one of the three AND gates. This generating a pressure pulse that launches another bubble in the delay line as a response. Cascaded switching of three AND gates in a ring structure achieves the function of an oscillator. The oscillation frequency of this device can be written as $f = 1/[3(l/v + \tau\_d)]$, where f is the oscillator frequency, l is the length of delay line, v is the mean velocity of the bubble traveling in the delay line, and $\tau\_d$ is the propagation delay of the AND gate. The frequency of oscillations can be tuned, which is shown experimentally by increasing the flow rate of the continuous phase.

FIG. 33 depicts a ring oscillator in operation, showing bubbles oscillating in a ring configuration. In FIG. 33, three AND gates are connected in a ring configuration via three delay lines to form a ring oscillator depicting feedback and cascadability. Three input ports are driven by T-junction bubble generators with a constant flow (water 2% w/w Tween 20) from syringe pumps (Kent Scientific) and a constant pressure nitrogen line. A bubble in the delay line arrives at an AND gate, causing a sharp increase in the outflow resistance of the gate and hence resulting in a release of another bubble in the delay line. The white arrow in each frame marks bubbles traversing counter-clockwise in the ring. The frequency of oscillation for the device operated at Q=0.5 µl/sec, $P\_0$=0.8 psi is 7.9 Hz. The propagation delay for the AND gate is ~10 ms at a flow rate of Q=0.5 µl/sec. The Ca number for the device is 0.03, with the scale bar at 100 µm.

Figure 34A:
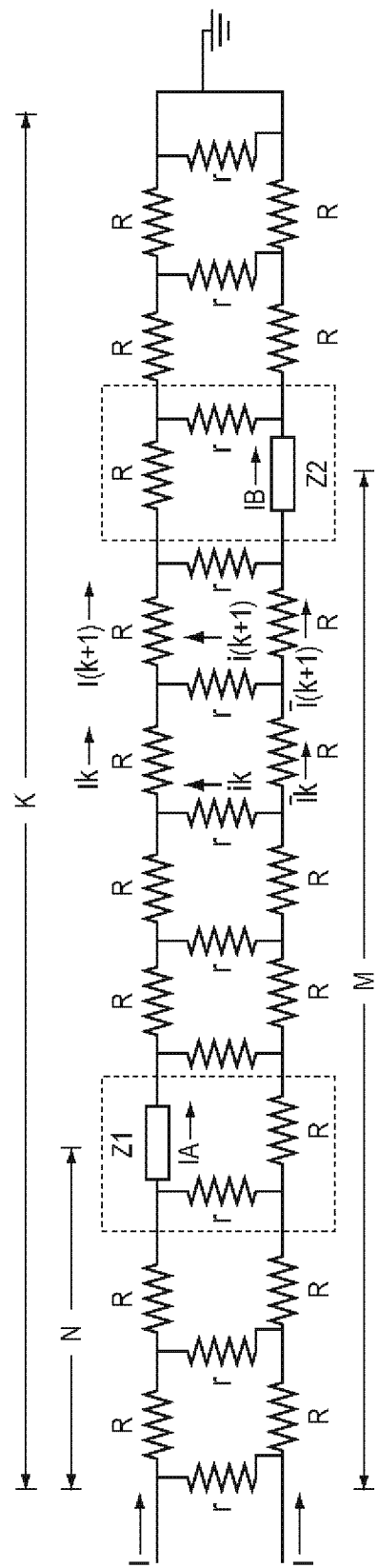
FIG. 34A depicts a lumped element model of a timing restoration device, according to one aspect of the present invention.
Figure 35:
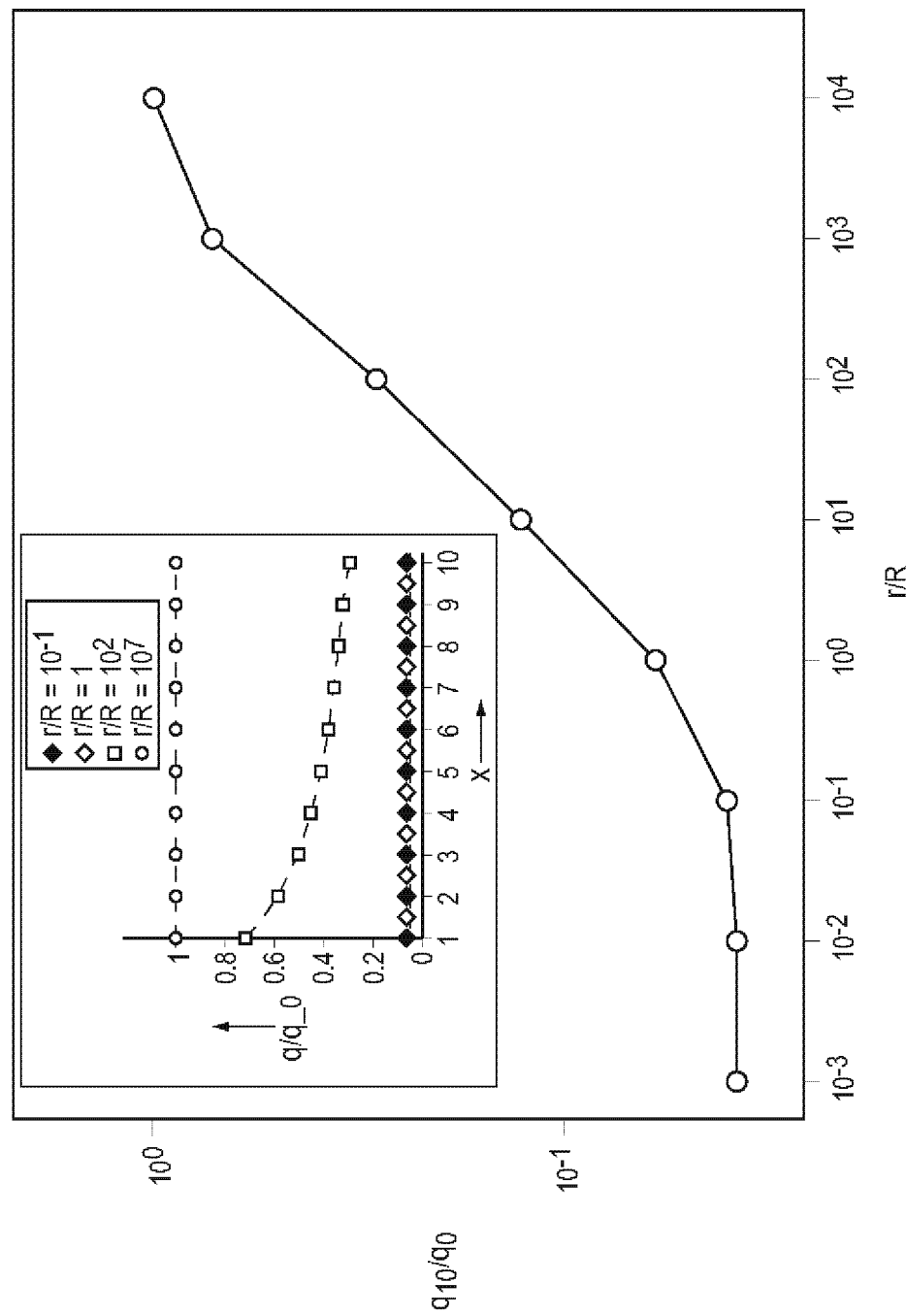
FIG. 35 is a numerical simulation of a single bubble traversing a timing restoration device.
Figure 36:
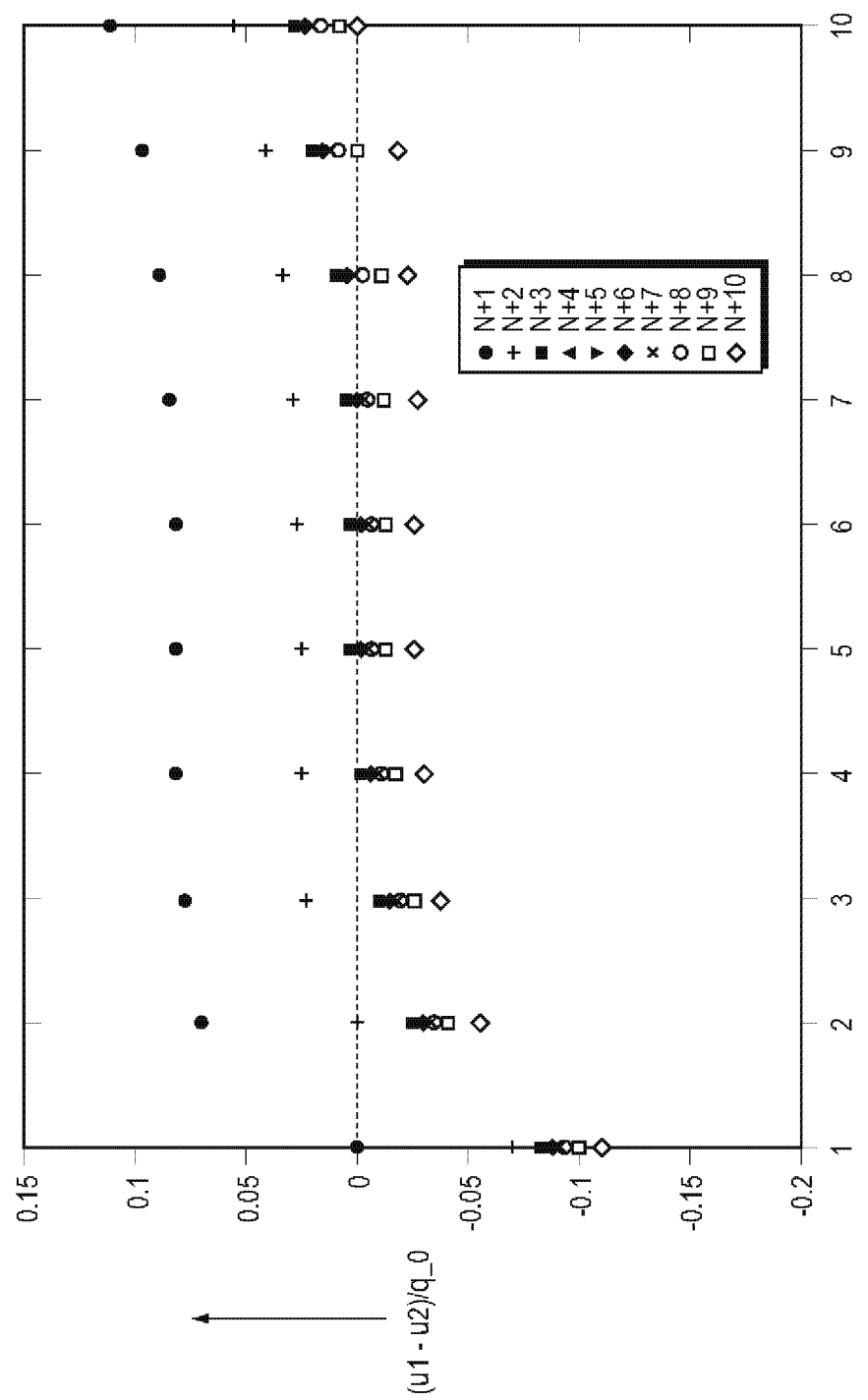
FIG. 36 is a numerical simulation of the relative velocity of a bubble in a top horizontal channel with respect to a bubble in a bottom horizontal channel of a timing restoration device.

For digital systems, where information is encoded in a timed sequence of bits, ability to synchronize two independent data streams is important for scalability. In an analogous manner, arrival time of a bubble at a logic gate governs the behavior of a bubble logic device. Synchronization of two independently generated input bubble streams via a passive fluidic geometry has been demonstrated. Such a timing restoration is also critical for on-chip passive droplet coalescence, which requires two drops to arrive at a junction in a synchronized manner. This timing restoration is achieved via a planar fluidic resistance ladder network. The geometry includes inter-connecting fluid channels (continuous phase flow resistance r) between two data carrying channels (continuous phase flow resistance R, where r>R (FIGS. 34A-B)). A single bubble traversing the ladder geometry is slowed down due to presence of an alternate path (via inter-connecting channels) for the fluid behind the bubble. The total drop in velocity scales with number of inter-connecting channels. When both bubbles are present in the network simultaneously, inter-connecting channels between the two drops allow for net flow from channel with the leading bubble to the one with the lagging bubble. This relative velocity gradient allows for synchronization (FIGS. 35 and 36). Once the bubbles are synchronized in the network, the bubble configuration is symmetric and hence both bubbles travel at the same velocity in a synchronized manner.

Figure 34B:
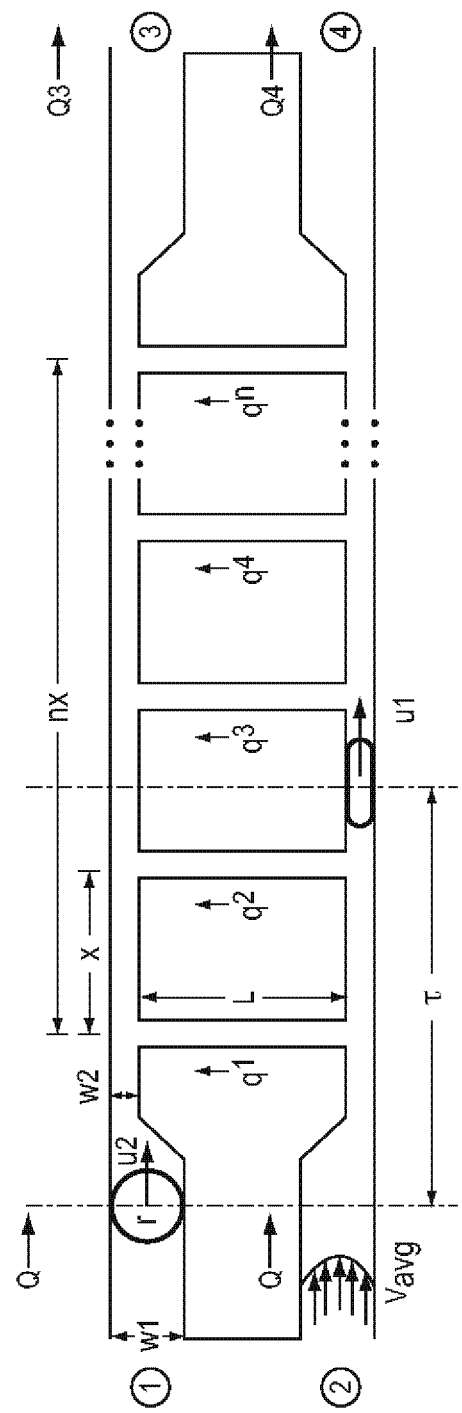
FIG. 34B depicts timing restoration device geometry for bubble synchronization, according to one aspect of the present invention.

FIG. 34B depicts timing restoration (TR) device geometry for bubble synchronization. Bubbles only traverse in horizontal channels while the vertical channels provide flow from one channel to another to achieve synchronization. FIG. 34A depicts a lumped element model of the TR device, where R and r represents linear flow resistance to single—phase flow. $Z1$ and $Z2$ (non-linear resistors) mark the locations of bubbles present in the ladder network at a given point of time. FIG. 35 is a numerical simulation of a single bubble traversing a TR device. The bubble slows down due to alternate flow path present for the fluid behind the bubble. Log scale plot of dimensionless exit flow $Q10/Q0$ is plotted against the ratio of inter-connecting and bubble carrying channels (r/R). Number of inter-connecting channels, K=10. Inset depicts variation in bubble velocity along the device for numerous values of r/R. FIG. 36 is a numerical simulation of relative velocity of the bubble in the top horizontal channel (marked by location N) with respect to a bubble in the bottom horizontal channel (marked by M). Relative bubble velocity $(u1-u2/Q0)$ is plotted for various locations of M and all values of N (where M,N represents a state of the device with bubbles at location M and N along horizontal channels). The relative velocity of top bubble against the bottom bubble is either negative or positive based on which bubble is leading or lagging.

The device physics for bubble logic is governed by physical fluid dynamics of bubbles in static microchannel geometries with no moving parts. Thus, bubble logic chips can be fabricated in a wide variety of materials including silicon and glass, allowing porting of reaction chemistries unsuitable for PDMS channels. Bubble logic devices operate at low Reynolds and Capillary numbers where surface tension and viscous forces are dominant compared to inertial forces, thus further reduction in size is feasible with faster switching times. The device mechanisms do not depend on non-Newtonian fluid properties, hence matching dimensionless flow parameters will allow bubble logic circuits to be designed using different fluids, e.g. water droplets in oil and oil droplets in water.

Universal AND/NOT Bubble Logic Gate.

A universal logic gate with gain (amplification) may be implemented according to one aspect of the present invention. It is universal, since any Boolean logic circuit can be constructed by cascading the described logic gate. The device also exhibits amplification, where amplification is defined as ratio of switched bubble to control bubble diameter. Thus a small control bubble can route a much larger signal bubble. Amplification in bubble logic plays a similar role to pressure amplification in hydraulic or pneumatic circuits. Thus, a series of amplification stages allow transformation of a small bubble signal train into large bubbles that can be used for actuation. In any logic family fan-out, it is necessary for the output signal from one gate to act as an input signal to multiple gates. In the case of bubble logic, this can be implemented by splitting bubbles at a T-junction [D. Link, S. Anna, D. Weitz, H. Stone, *Phys. Rev. Lett.* 92, 054503 (2004)] that reduces the size of the individual bubbles produced (signal is represented as bubble size). Thus, to restore signal levels in a logic family, gain is necessary (where gain is defined as the ratio of the volume of the output to the control bubble).

FIG. 28A depicts an embodiment of a bubble logic AND-NOT gate. The device is a universal logic Boolean gate since it can evaluate both AND and NOT logic functions. Thus, any Boolean logic expression can be evaluated by cascading the above device. The scale bar is 100 microns. Incoming channels marked as A and B act as the input stream, while outgoing channels marked NOT(A).B and A.B compute the output. FIG. 28A depicts an inverter with gain where a small control bubble can switch the output flow direction for a larger bubble. A NOT gate is a non-conservative Boolean operation, hence in bubble logic it is implemented as NOT(A).B gate where the value of B can be set to 1 by applying a constant frequency bubble train. Thus, since the same geometry can implement both AND and NOT, it forms a universal logic gate capable of evaluating any given Boolean logic via cascading the same device. The gate consists of a planar geometry with two competing flow asymmetries. The bottom T-junction consists of an asymmetric bifurcation with a narrow channel NOT(A).B and a wider channel marked A.B. A side flow from the top channel with input A is introduced in the wider bifurcation by a thin channel, connecting the two channels with an offset to the T junction.

Figure 37:
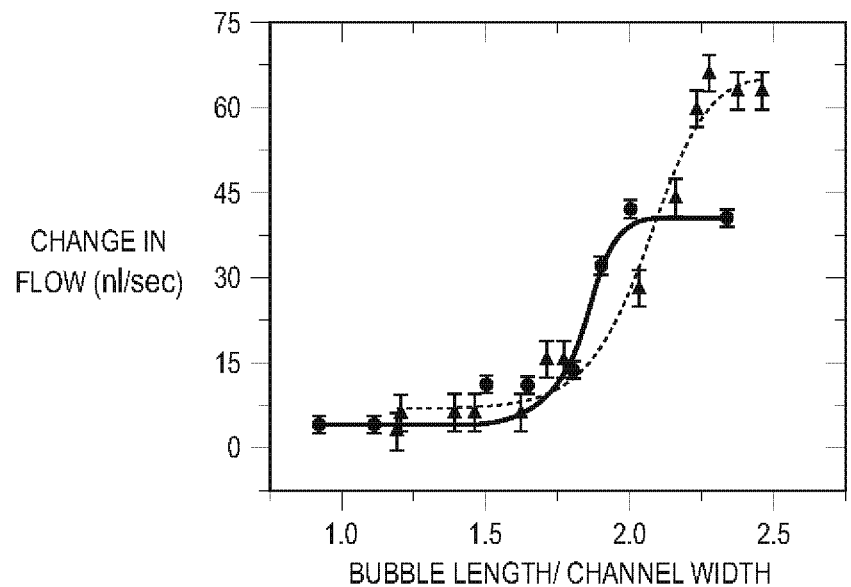
FIG. 37 depicts nonlinearity in an AND-NOT bubble logic gate by plotting change in flow against dimensionless bubble size depicting a threshold.

FIG. 28B depicts an AND-NOT universal bubble logic gate in operation. The top series of micrographs, taken from a high speed video, show A=0 and B=1, evaluating NOT(A).B=1 and A.B=0. For the bottom series of micrographs, A=1 and B=1, evaluating NOT(A).B=0 and A.B=1. The device does not produce or destroy bubbles, hence it conserves the number of bits entering the device. This injected flow can be seen as the dark fluid in a series of micrographs, which forces most of the light colored fluid at the bifurcation to enter the narrow channel. By introducing a bubble in the top channel, the injected side flow may be dynamically turned on and off, and hence the direction of flow of the output bubble arriving at the bifurcation may be controlled. Net change in the flow through the thin connecting channel (Delta Q) is non-linearly related to the size of the input bubble at A, as plotted in FIG. 37 against dimensionless bubble size (bubble length/channel width). In FIG. 37, nonlinearity in the AND-NOT bubble logic gate is demonstrated by plotting change in flow (Delta Q)) against dimensionless bubble size depicting a threshold. For a small bubble size, Delta Q is very small. With increase in the bubble size, Delta Q suddenly increases and saturates at a given value. Solid line depicts Q_A/Q_B=0.6 while dashed line depicts Q_A/Q_B=1.

For a very small bubble in A, the viscous dissipation in the fluid between the bubble walls and confining channels is small (thus small Delta Q). As bubble length is increased, a thin lubrication film is formed around the bubble that increases Delta Q sharply. Beyond a certain critical bubble length, the width of the lubrication film does not vary (the bubble behaves like a semi-infinite bubble traveling in a channel), hence saturating Delta Q at its maximum. This nonlinearity is used as a gain mechanism, where a smaller bubble from A can switch a larger bubble coming from the constant frequency input channel (e.g. FIG. 28B).

Toggle Flip Flop/Ripple Counter/Bubble Latch.

Figure 38:
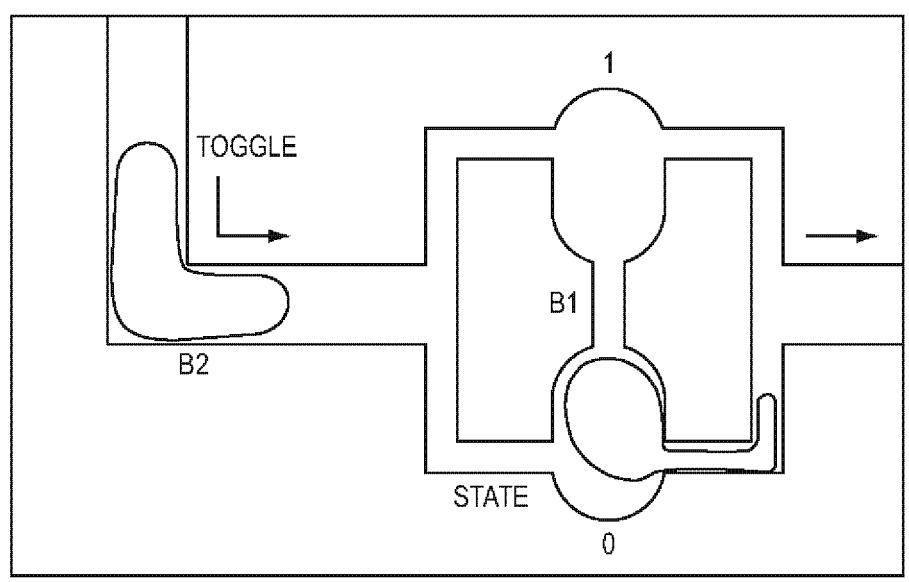
FIG. 38 depicts a toggle flip-flop consisting of a planar geometry formed in micro-channels, according to one aspect of the present invention.

In co-pending U.S. patent application Ser. No. 11/416,449, filed May 2, 2006 and published Jan. 11, 2007 as US 2007-0006926A1, a bistable memory element is described for storing one bit of information/bubble in the device geometry. A non-destructive read-out mechanism for the same is also described. In addition, a toggle flip-flop may be constructed from the bistable mechanism. Similar to electronic flip-flops, the device stores one bit of information in state of the bubble (bubble location in the device), and its state can be toggled as input signal is applied. The described toggle flip-flop consists of a planar geometry formed in micro-channels, as shown in FIG. 38. In FIG. 38, toggle flip-flop geometry, the bubble state is used to store information. Since the arriving bubble is presented with an energy trap, the device can be used to store chemicals or a material payload indefinitely, until a toggle signal is applied which switches the state of the flip-flop.

Figure 39:
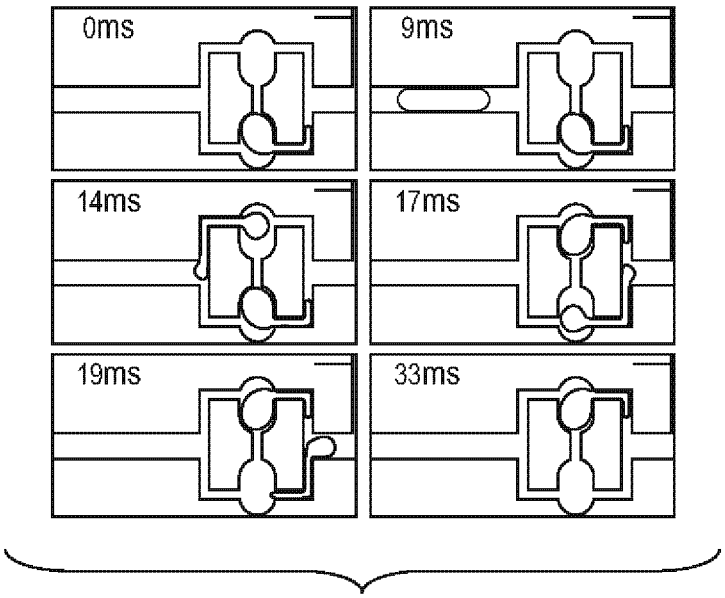
FIG. 39 depicts a toggle flip-flop in operation at 30 Hz, according to one aspect of the present invention.

FIG. 39 depicts a toggle flip-flop in operation at 30 Hz. The device in operation is depicted in a series of micrographs. Since the fluid is presented with an alternate route through the second lobe, this geometry acts like a fluid dynamic bistable trap for a single bubble traveling at low capillary and low Reynolds number. In this representation, the bubble in the lower lobe represents state 0 and the bubble in the upper lobe represents state 1. A toggle event occurs when a bubble arriving from the input flips the state of the device from 0 to 1 and vice versa. The device holds a single bubble indefinitely until another toggle signal arrives. An important feature for the device is a mechanism to dislodge a trapped bubble (B1) once a toggle bubble (B2) arrives, which is done by providing an interconnecting channel between the two lobes. An expanding bubble B2 in a lobe causes a pressure pulse due to flow through the interconnection that dislodges B1 from its energy minima. This allows flow to be redirected to the empty lobe significantly reducing the fluid pressure on B2 itself and hence stabilizing the trap again. Size of the bubble determines the stability of the trap against the surrounding flow. For a small bubble size, the energy barrier to dislodge a bubble is small which is easily overcome by the pressure buildup due to flow in the continuous phase. To evaluate the repeatability and bit error-rate, time traces for operating toggle flip-flop devices for a duration of ~10 seconds were collected.

Figure 40:
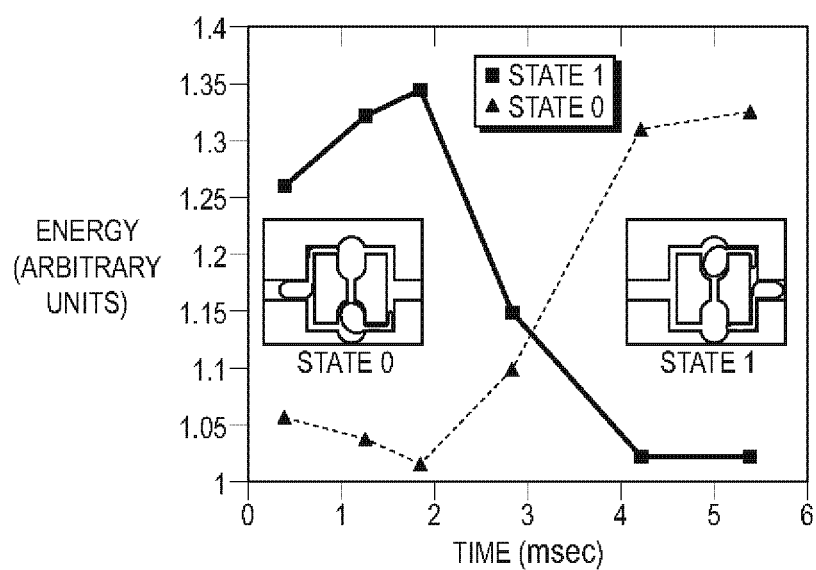
FIG. 40 depicts the energy landscape of the device of FIG. 39 in operation.
Figure 41:
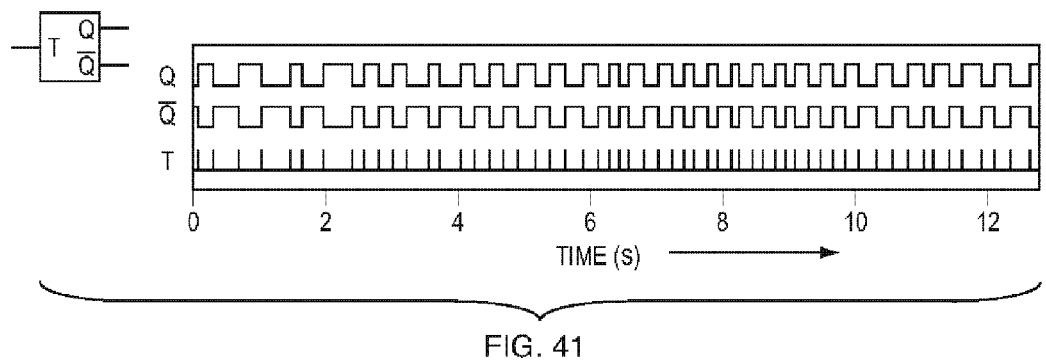
FIG. 41 depicts the repeatability of the device of FIG. 39 from a time trace obtained by optical readout of the memory gate.

FIG. 40 depicts the energy landscape of the device in operation. The toggle flip-flop geometry (FIG. 38) presents an incoming bubble with two elliptical lobes where the surface energy of the bubble is at its minimum, as shown in the plot of energy vs. time of FIG. 40. FIG. 41 depicts the repeatability of the device via a time trace obtained by optical readout of the memory gate for a period of 12 seconds. The time trace is depicted in FIG. 41 for a period of 12 seconds with no bit-error in the sequence.

A bottleneck in current microfluidic devices exists in the rate at which information can be extracted from the microfluidic chip via analysis of components being formed or analyzed on the chip. Since measurement times for various techniques can vary, a bistable trapping mechanism that can hold a droplet/bubble for a programmable duration of time is required. After the measurements have been performed, the trap should be reloaded with new material/chemical set. This is exactly the functionality performed by the toggle flip-flop device. Thus, the toggle flip-flop geometry provides a completely fluid-dynamic bistable trap that can be programmed. This is superior to other electrophoretic of electrostatic traps, since electromagnetic fields can sometimes cause unwanted effects on the sample. The simplicity in implementation and fabrication of the above-described trap permits arraying a large number of toggle flip-flop devices with standard soft-lithography based fabrication techniques.

Figure 42:
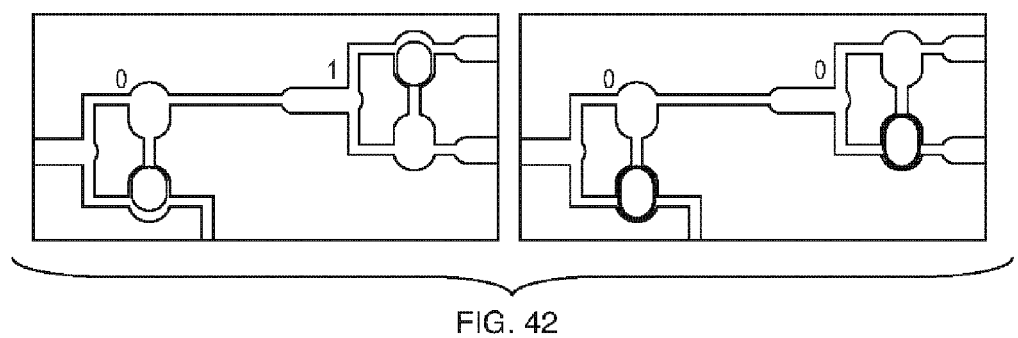
FIG. 42 depicts a ripple counter constructed by cascading two toggle flip-flops in series, according to one aspect of the present invention.

Bistability permits construction of sequential circuits such as counters and memory arrays. It is possible to array and cascade the described toggle flip-flop. FIG. 42 depicts a ripple counter constructed by cascading two toggle flip-flops in series (similar to its electronic counterpart). The device can thus be used to count exact number of bubbles arriving from a serial channel input. Since the device is a fluid dynamic digital counter, the output of the device is precise. Also, the counter shown can be used as a metering device, allowing only a specified volume of fluid into a reaction chamber (based on number of bubbles/droplets). This forms a completely passive way of metering in microfluidic devices. This provides an all-fluidic digital means for delivering small volume fluids in a controlled and a very precise manner, which is useful for various applications in programmed drug delivery and analytical chemistry.

Figure 43:
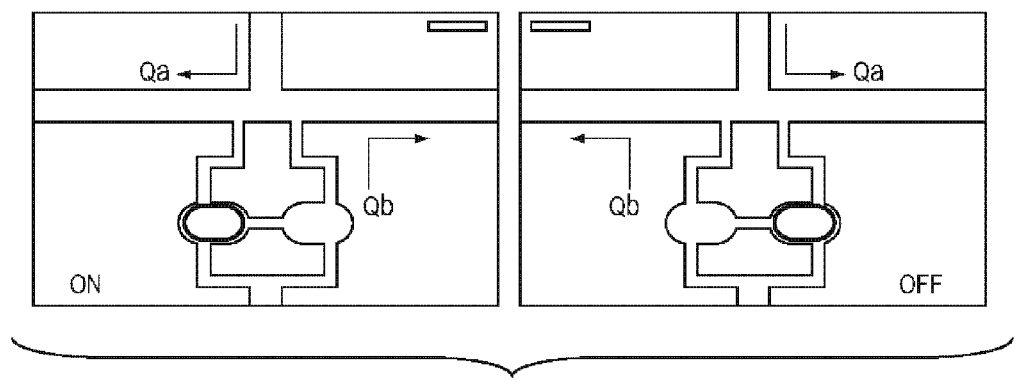
FIG. 43 depicts a microfluidic bubble valve/latch constructed from a modified toggle-flip geometry, according to one aspect of the present invention.

The bistability mechanism has also been used to implement a bistable flow-switch or valve. FIG. 43 depicts a microfluidic bubble valve/latch constructed from a modified toggle-flip geometry. The valve is operating at a flow rate Q_a that is capable of switching another continuous phase fluid (with flow rate Q_b) or a train of bubbles. The valves can be turned ON or OFF by a bubble signal and they store the state of the valve. Thus, a signal is needed only to switch its state, and the flow-switching valve maintains the state stably. Due to its use of microscopic dynamics, switching time for the device in KHz range, which is an order of magnitude faster when compared to other macroscopic elements like external solenoid valves. This permits construction of complex valving architectures for fluid control with higher operating speeds.

Ring Oscillator.

Cascadability and feedback are two important features of digital logic. Cascadability refers to the ability to connect modular components in a complex network, and thus creating a complex functionality from simple parts. Feedback refers to the notion where a signal can act on itself and hence change its state. In U.S. patent application Ser. No. 11/416,449, implementation of a ring oscillator using NOT gates was described.

A ring oscillator formed by three AND gates and three delay lines cascading a ring geometry is also possible.

Figure 44A:
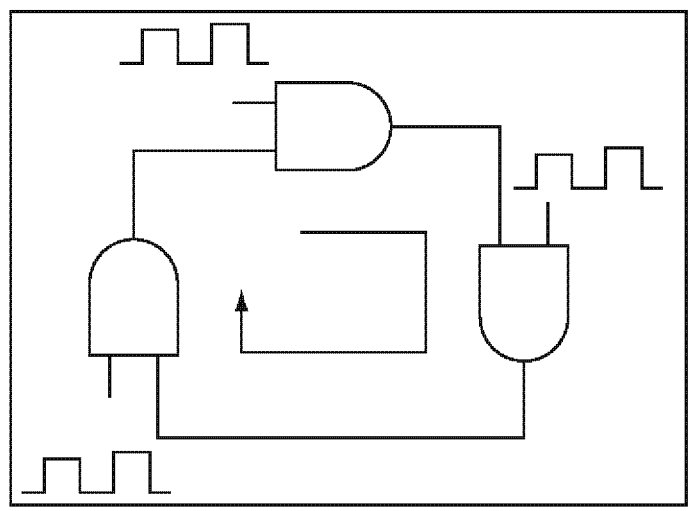
FIG. 44A is a circuit schematic of a ring oscillator using three AND gates and delay line arranged in a ring configuration, according to one aspect of the present invention.
Figure 44B:
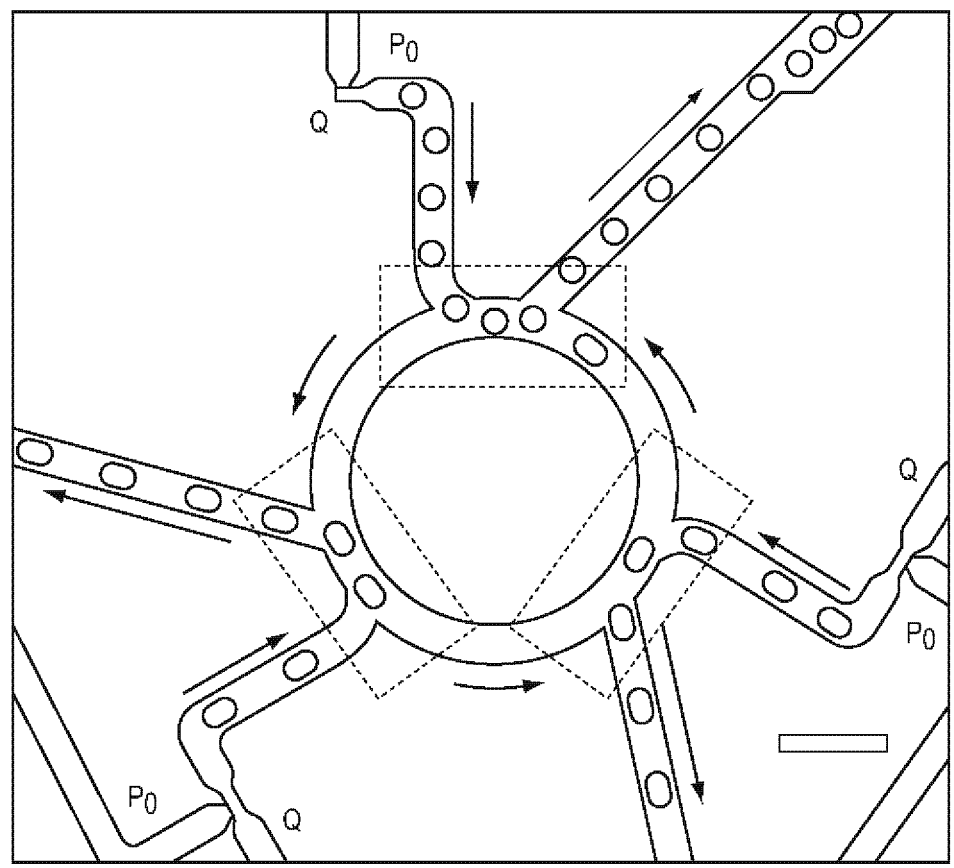
FIG. 44B is a photomicrograph of the channel geometry of the planar microfluidic ring oscillator of FIG. 44A.
Figure 44C:
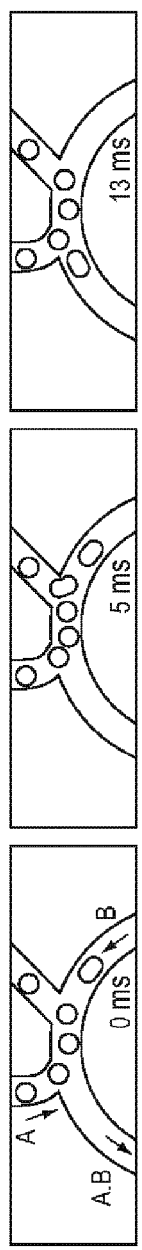
FIG. 44C depicts a zoom in on the mechanism of AND gate operation in the ring oscillator of FIG. 44A.

FIG. 44A is a circuit schematic of a ring oscillator using three AND gates and delay line arranged in a ring configuration. FIG. 44B is a photomicrograph of the channel geometry of a planar microfluidic ring oscillator. FIG. 44C depicts a zoom in on the mechanism of AND gate operation in a ring oscillator. The operation of an individual AND gate is depicted in FIGS. 44D-I. The two inputs for the AND gate are marked as A and B in the first frame of a series of photomicrographs. The output channel is marked A AND B. A bubble propagating from channel B increase the resistance of the output channel for the device generating a pressure pulse that launches a bubble in the delay line. Prior to onset of oscillations, the ring does not contain any bubbles. With any small perturbation in pressure from one of the gas inlet lines, a bubble can be excited to travel to the sink via the ring structure. This is achieved by simply tapping gently on the external inlet connection.

Figure 44D:
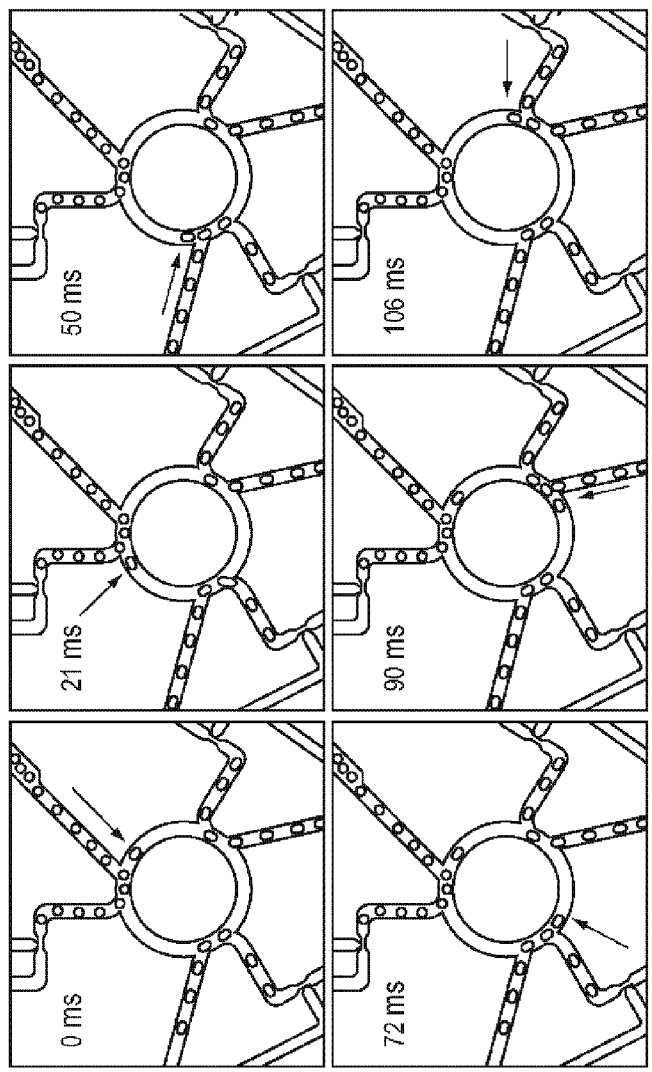
FIGS. 44D is a series of photomicrographs obtained from high speed video imaging of the device of FIG. 44A, showing the operation of the ring oscillator.

The bubble travels in the delay line (one of the three branches of the ring structure) at a velocity much lower than the mean flow velocity in the exit channels. This cascaded switching of AND gates in a ring structure achieves the function of an oscillator. Oscillation frequency of the device can be written as $f \sim 1/[3(l/v+\tau_d)]$, where f is oscillator frequency, l is length of delay line, v is mean velocity of the bubble traveling in the delay line and $\tau_d$ is propagation delay of one of the gates. Thus, frequency of oscillations increase with the net flow rate $Q\_net$ from the inlets. FIG. 44D depicts a single cycle of the oscillator running at 7.9 Hz. In FIGS. 44D-I, the operation of the ring oscillator is shown in a series of photomicrographs obtained from high speed video imaging of the device. For operating flow rate of Q=0.03 ml/min, velocity of the bubble in the delay line is ~2 cm/sec. The Ca number for the device is 0.03. For a flow rate Q=0.03 ml/min, Re is 2. Varying the flow rate increases the oscillation frequency of the ring oscillator.

Figure 45:
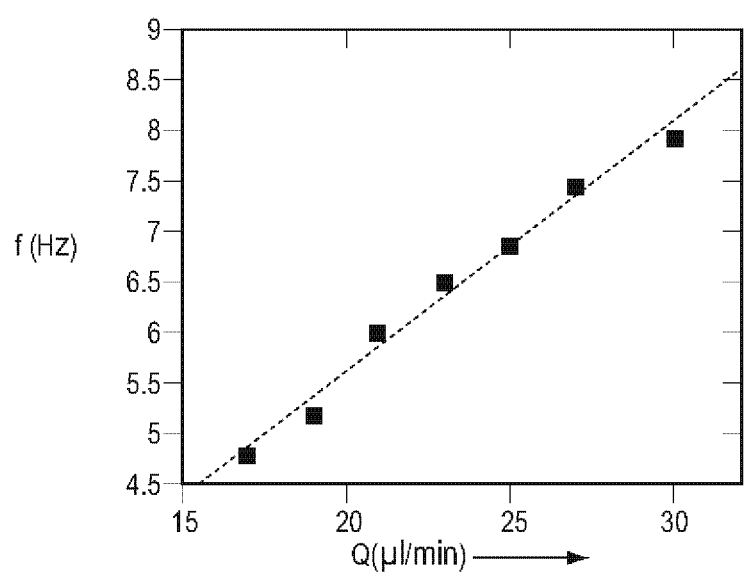
FIG. 45 is a plot of oscillation frequency vs. flow rate depicting tunability of oscillation frequency based on the net flow rate.

FIG. 45 is a plot of oscillation frequency vs. flow rate depicting tunability of oscillation frequency based on the net flow rate. A linear relation between frequency f and flow rate Q is shown. Smaller ring structures will oscillate at higher frequency.

Bubble Synchronizer.

Information in bubble logic devices is encoded in relative timing of streams of bubbles. Thus arrival timing of a bubble at a specified geometry plays an important role. To correct for errors accumulating over time and synchronize bubble streams from two independent generators, the present invention may employ a bubble synchronizer (similar to bit synchronizer in electronic circuits). This is necessary for scalability of the devices forming large-scale integrated systems. The synchronizer can correct for errors at various different stages permitting scaling of the system to large numbers.

For performing chemical reactions inside droplets on a microfluidic chip, it is required to merge droplets/bubbles coming from different sources. This requires droplets/bubbles to arrive in a synchronous manner to a channel geometry. This is achieved by employing the bubble synchronizer in a completely passive way (without use of any active control from outside). The geometry of the device can be tuned to obtain maximum correction in timing required for a given device.

Figure 46:
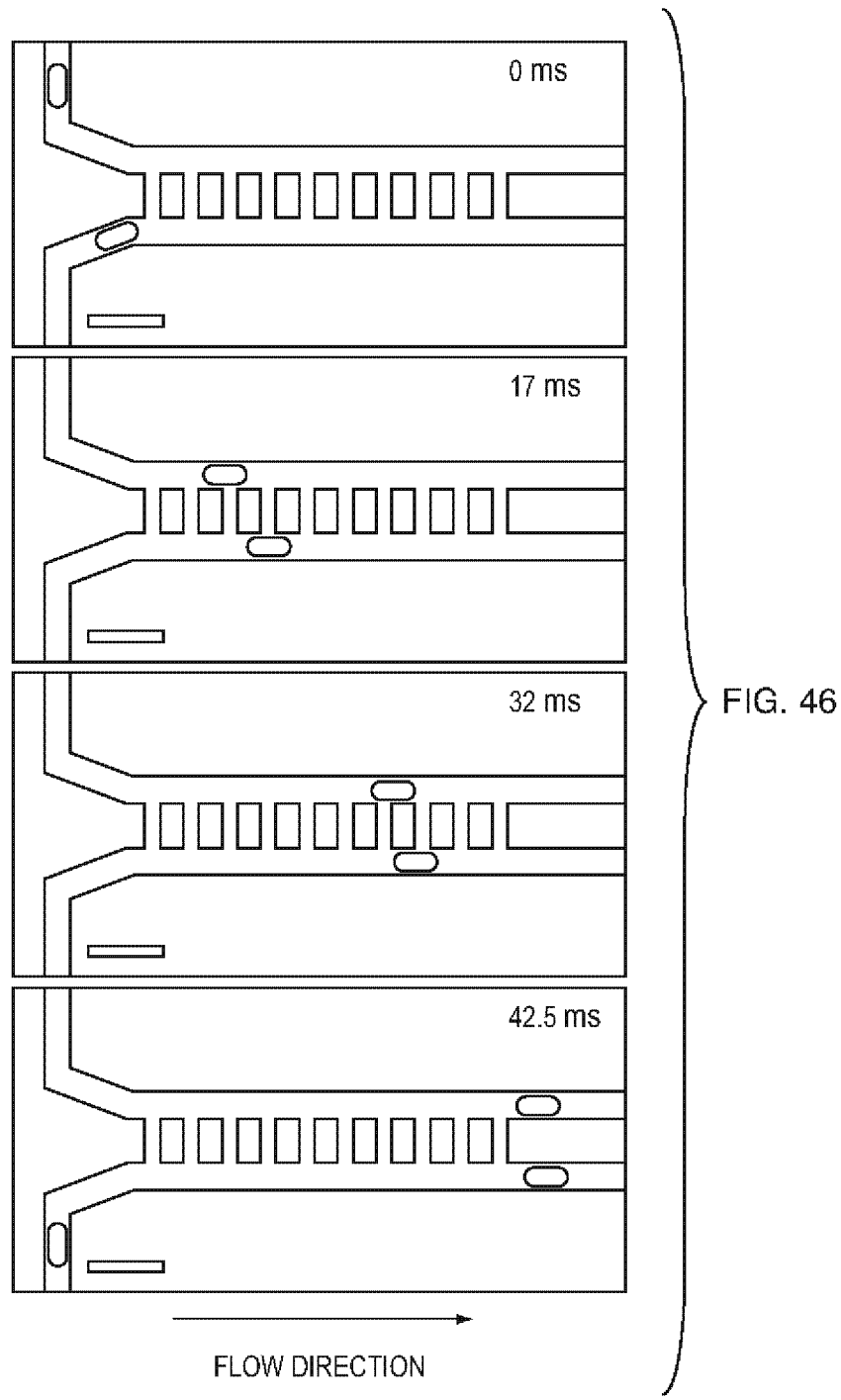
FIG. 46 is a series depicting the operation of the microfluidic bubble/droplet synchronizer of FIGS. 34A and 34B.

FIGS. 34A and 34B depict an embodiment of a bubble synchronizer. The device consists of a microfluidic planar ladder network as shown in the schematic. A non-linear resistor network model of the same can be used to model the device behavior. The bubble synchronizer device geometry consists of a non-linear ladder network formed by microchannels. The two data carrying channels (wider channels, lower fluid resistance) are connected by a series of interconnecting channels (thinner channels, higher fluid resistance). Presence of a bubble in a channel drastically increases the flow resistance of the channel. Thus, the device can be modeled as a non-linear resistor ladder network where the resistance of individual fluidic channels is dependent on the state (position) of bubbles traversing the device. Once a single bubble enters the device geometry, the bubble is slowed down due to the presence of alternative flow path for the continuous phase fluid. For bubbles present in both the channels, an asymmetry is developed where the path of least resistance for the continuous phase fluid is dependent on the number of interconnecting channels between the two bubbles (i.e. distance between the two bubbles). A relative velocity gradient exists between the two bubbles, bringing them closer to each other over the length of the device. Whenever the bubbles become synchronized, the asymmetry is lost and the bubbles move simultaneously. Thus, a timing error can be corrected between two streams of bubbles. FIG. 46 depicts a microfluidic bubble/droplet synchronizer. A series of micrographs from a high speed video camera were made of the operation of the device where bubbles/droplets from two streams are synchronized over a period of time as they traverse through the channel geometry. In FIG. 46, a passive bubble synchronizer for timing restoration, the planar device (channel height 70 μm) consists of a fluidic ladder network with two (50 μm wide) parallel channels with equal flow (driven by constant flow syringe pump, Kent Scientific) and 10 interconnected channels (25 μm wide, 100 μm long, 75 μm pitch). A timing restoration of ~10 ms is achieved between two arriving bubbles over a span of ~40 ms at a flow rate of Q=0.5 μl/sec.

Printing on External Substrates.

Figure 47:
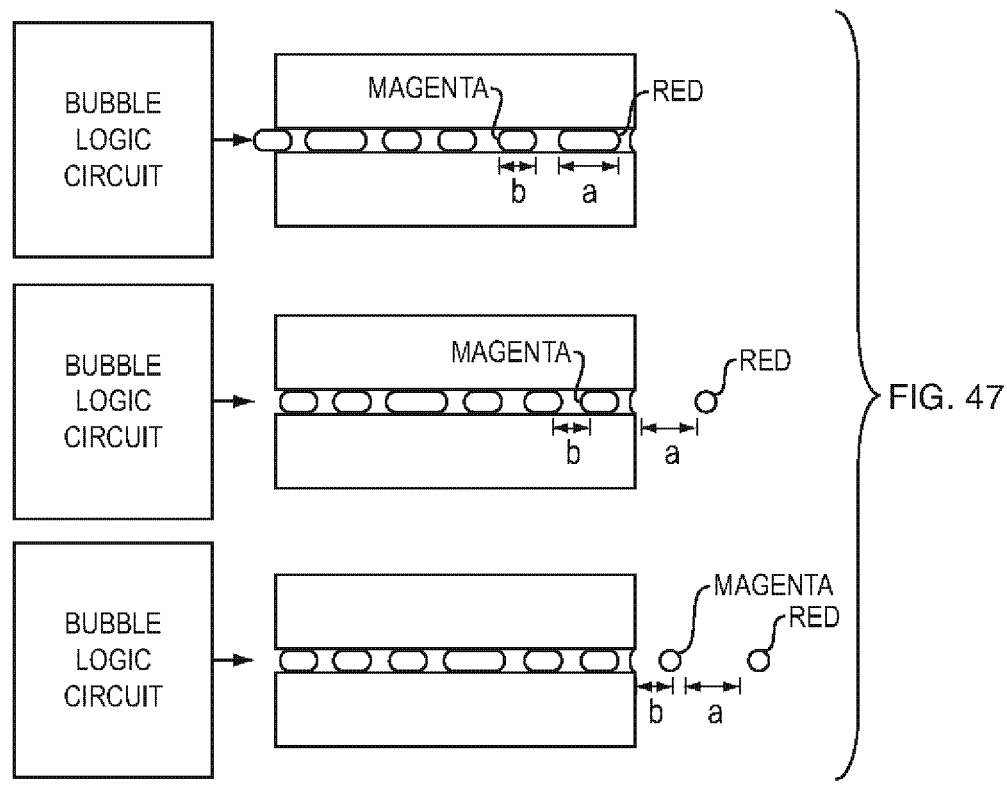
FIG. 47 is a schematic depicting printing using a single microfluidic channel, according to one aspect of the present invention.

Bubble logic provides a new way of building microfluidic printing cartridges for high-throughput, multi-material printing. The basic printing mechanisms consists of a large-scale microfluidic bubble logic chip with multiple sealed channels opening into air. The inkjet nozzle consists of a series of drops/bubbles traveling in a micro-channel. The drops are spaced with air bubbles, thus forming individual ink droplets when they come out of the channels. The mechanism is depicted in FIG. 47. Length of bubbles segmenting the ink droplets determine the time interval between different droplets. Also, numerous colors/inks can be handled at the same time. In FIG. 47, a schematic of printing operation from a single microfluidic channel, the segmented flow allows splits ink droplets in various segments. Length of air bubbles in the segment assigns the duration of time between droplets ejected from the nozzle. By programming the size of the bubble, precise droplet spacing can be defined. Various colors can also be printed at the same time from the same nozzle. A variety of ink formulations can also be formed on the fly.

Figure 48:
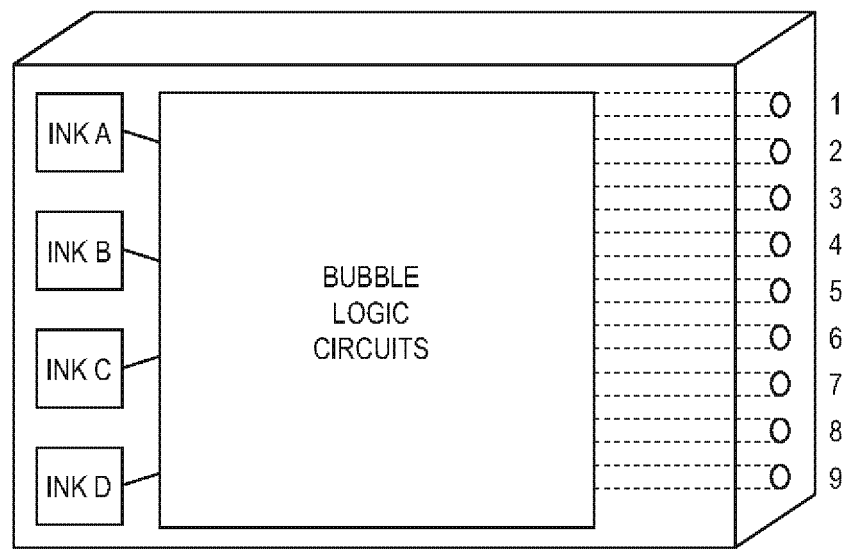
FIG. 48 is a schematic of a bubble logic chip-based print head, according to one aspect of the present invention.

Another important aspect is the implementation of large number of nozzles on the same chip providing higher throughput, as shown in FIG. 48, a schematic of a bubble logic chip-based print head. Various nozzles labeled 1-9 eject pressure/constant flow driven drops from marked channels. A number of ink formulations can be built by mixing a set number of inks in a number of proportions. The bubble logic circuit on the cartridge also provides a means to perform processing like font rendering, color printing and dithering on the fly using bubble logic. The device consists of a large number of nozzles implemented using micro-channel endings, a section of bubble logic circuit controlling the nozzles and numerous number of basic ink reservoirs. Since ink formulations can be made on the fly by material/chemical processing, the number of possible colors available for printing (or other formulations) is large.

Since the individual droplets containing specific material to be printed can be individually routed/manipulated/rearranged on chip before being ejected from the nozzle, a space-time tradeoff may be made in any given printing operation. A print pattern can be obtained by moving a printhead in space and controlling everything sequentially, or a pattern can be formed on the bubble logic chip and simultaneously transferred onto the substrate. Conventional printing techniques are extremely limited in the spatial manipulation of droplets ejected from the print-head nozzle. A bubble logic printhead overcomes this problem with the ability to manipulate individual droplets precisely in space and time. The mechanism of ejection can be either constant pressure or constant flow based. Thus, a stream of droplets ejected from a microfluidic cartridge can deposit a given set of materials on an external substrate. Moreover, spatial rearrangement of the actual drops can also be performed by performing logical operations on the stream, relevant to the pattern of printing required. The printing cartridge therefore has the ability to both spatially organize and eject a stream of droplets. Various operations like color printing by mixing various color drops in different proportions, font rendering, dithering etc. can be performed using bubble logic processor, manipulating both droplets to be printed and information related to the above operations. Various control tasks, such as feedback control on droplet size and other control functionalities, can be performed in the cartridge itself by employing bubble logic circuits on it.

Bubble logic also provides the ability to perform complex chemical/materials processing on a chip. Thus pre-processing of functional materials and biological samples is possible. Various functional materials, biological samples and inks can be printed on a given substrate by the method discussed earlier. Processing of the sample (such as on the fly formulation of a specific type of inks/functional material on chip, fabrication of polymers, and fabrication of fibers) can also be performed on the microfluidic printing cartridge by employing the material handling and processing capabilities of bubble logic chips. Hence, rather than storing all different types of printing materials, as is commonly done, a large number of formulations/materials can be available for printing. This also permits various operations, such as tuning the concentration of printed substrate and optimizing viscosity. Various other material properties can also be tuned on the fly. Because of availability of a very large set of functional materials on the microfluidic chip driving the printing cartridge, it is possible to print electronic materials on a substrate, allowing fabrication of printed electronics on the fly. The simplicity of providing the controls and functionalization of the materials on the chip, making it easier to implement complex chemistries and control sequences without bulky external control.

Printing on external substrates also permits access to the reactants formed on a chip. This allows analysis of reactants produced on-chip. A series of samples can be ejected in a stream of gas for chromatographic analysis. The printing technique can also be used with the bubble logic processors to print reactants on a substrate, which can be analyzed via traditional micro-arrays or florescent detection techniques.

Microfluidic on-the-Fly Sample Collection.

As described earlier, bistable bubble logic memory can store a given sample for indefinite period of time. This sample can be recalled for further analysis. This is possible using a large array of bubble logic memory elements, forming a chemical memory analogous to data memory. Bubble logic elements and memory chips provides an easy way to store a sample at a pre-determined location. For an online-sample collection application, a bubble logic chip is connected to continuous supply of material being tested. The logic chip extracts a sample volume of liquid from the sample stream at a specified time/location that is stored in the memory register. The information about the sample (data/time/location of collection) can also be stored with the sample, thus requiring no other documentation/tagging external to the sample. Bubble logic chips can extract a small amount of sample from a co-flowing stream by encapsulating a small liquid sample inside a droplet. This time-stamped sample can be stored in a memory element at a fixed register location by using bubble logic and bubble memory arrays. This permits sampling of an output stream at a rate defined by the user, where the bubble logic chip takes a sample from the production line and stores that sample for later analysis.

In a preferred embodiment, the on-line analysis chip consists of three parts. First is a bubble logic circuit for encapsulating and collecting a sample from stream of material to be sampled. The sample is encapsulated in an inert fluid that does not react to the material being sampled. Secondly, the sample is routed through a series of logic gates that determine the correct location, where the sample should be stored in the bubble memory chip. The third part is the memory itself, which consists of array of bistable memory elements and bubble logic circuits with the capability to address any location on the memory chip. Thus, the sample is finally stored in a specific location inside the memory. Any other information can also be stored encoded as a string of bubbles (bubble pattern), removing the requirement to catalog any other information externally from the chip.

Therefore, a memory chip provides a clean mechanism for cataloging the location and hence the time of sample collection in a simple manner. The technique allows for analysis of a continuous stream over long periods of time without putting costly analysis equipment inline with the production facility. The bubble logic chip can be transported to an analysis facility. Since a single bubble logic chip can be attached to the production line, a disposable and portable solution can be achieved. A large number of such collection points allows for an automated analysis/quality control of a production facility with numerous cost benefits.

Programmable Assembly of Materials in Bubble Logic Devices.

Bubble logic provides a means for performing both computation and material processing in a highly integrated platform. Thus, not only can materials be arranged in specific structure or geometry, the assembly process can be programmatically controlled by a set of finite state machine running the assembly process. Preferably, the state machine that encodes for the structure to be formed is also implemented using bubble logic. This provides an integrated platform for performing programmable assembly of materials. On-chip micro-assembly of a large number of parts can also be performed in a similar manner, with parts arriving at various geometries at specified times. Local interaction forces between various micro parts allow them to join together in a specified manner. The logic operation ensures the sequence of assembly is controlled, thus allowing only a single unique geometry to be formed. This is currently a problem in self-assembly techniques where a large number of possible interactions allow for error propagation in the assembly process.

Figure 49:
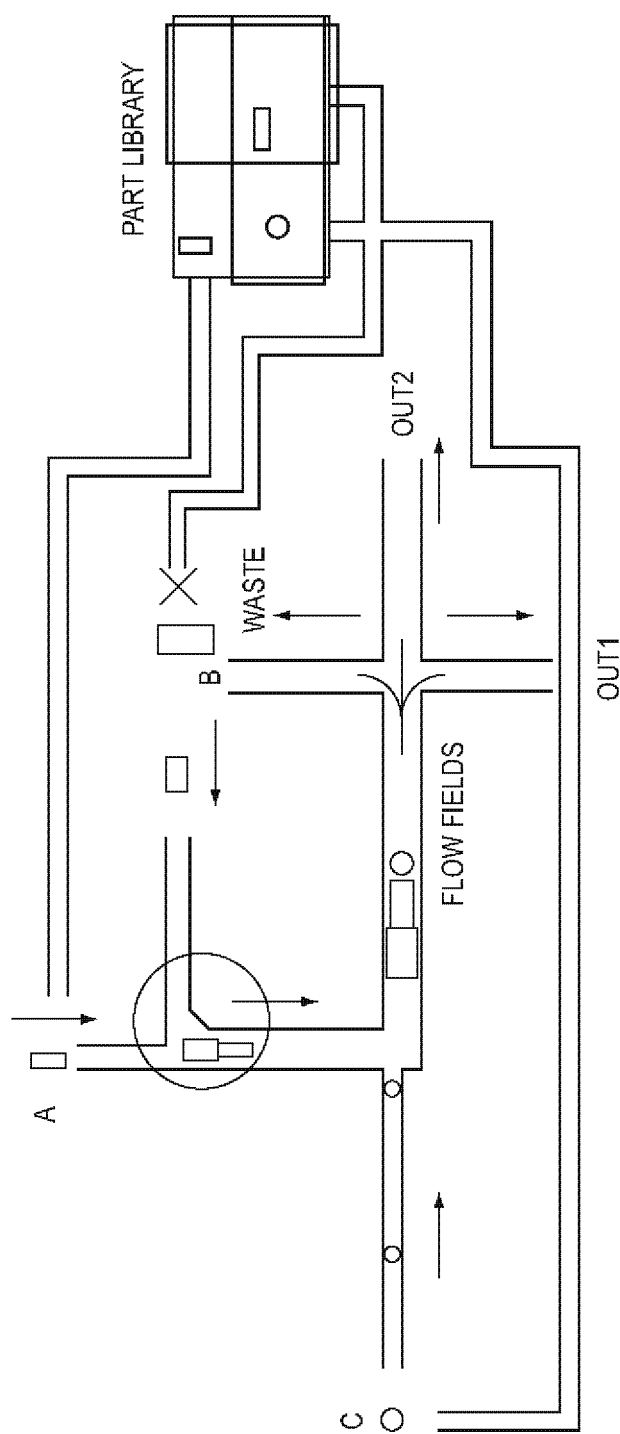
FIG. 49 is a schematic of a microfluidic bubble logic assembly chip, according to one aspect of the present invention.

In one embodiment, a bubble logic-directed assembly technique consists of the following parts: a parts library, logic circuits for storing and accessing the memory bank of parts, bubble logic circuits that assemble the parts in a programmable manner. FIG. 49 is a schematic of a microfluidic bubble logic assembly chip. Parts are captured/encapsulated in droplets/bubbles. The bubbles are routed using bubble logic, thus providing an integrated means to manipulate the trapped objects. Assembly is performed in a localized environment, for example, by merging drops/bubbles in a specific chamber. Parts libraries can be stored in bubble memory devices. As shown in FIG. 49, the parts library can be used to store a large number of parts, encapsulated inside bubbles/drops. The sub-assemblies can also be stored in the parts libraries. Local forces, (such as capillary, magnetic, electric) are used to assemble two parts encapsulated inside two droplets/bubbles. The specific geometry of the device ensures correct mating of parts, including orientation selectivity due to the channel geometry. Only specific binding occurs using these devices, thus making the assembly process controlled and error free. There are numerous domains in which programmable, directed bubble logic assembly system can be used. The device shown in FIG. 49 can also be extended to 3-D. Several examples of complex structures that can be fabricated using bubble logic are suggested herein, but it will be apparent to one of ordinary skill in the art that the present invention may be advantageously employed to fabricate many other such structures.

Electronic Components and Circuits Using Functional Inks.

Numerous ink formulations containing electronically active materials can be fabricated/introduced in bubble logic chip. This permits spatially building complex structures containing conducting, insulating, semi-conducting, light-emitting, sensing and numerous other components in liquid or solid phase on bubble logic chips. This provides a route to build functional electronics using functional material drops on the fly in a continuous fashion using microfluidic bubble logic chips.

Photonic Crystals.

Photonic crystals are currently fabricated by numerous crystallization/optics techniques that provide a means to form regular structures over large length scales. For interesting and designed optical behaviors, it is necessary to encode detailed structure in this crystal lattice, which is currently a challenge. Since numerous materials (for example colloidal particles in the current case) can be organized and arranged programmatically, bubble logic chips can both fabricate regular crystals but also be used to encode desired patterns in the crystals to form functional photonic materials.

Fabrication by folding a linear chain into a 3D geometry can be performed by first encoding information in a linear chain of bubbles/droplets employing bubble logic. This train of bubbles/droplets can be folded into a specific 3D structure by viscous/capillary forces in confined geometries where local force interactions are enhanced over global force interactions. This provides a route to building complex 3D structures at micro-nanometer scales employing simple 1D encoded strings/beads.

Automated Compound Libraries.

Compound libraries play a crucial role in the discovery of novel uses of these molecules as drugs or markers for a disease. With the advent of high-throughput technologies, such libraries provide an opportunity for novel discoveries made via selection of novel classes of compounds from a vast number of similar compounds. This requires liquid handling platforms for storage and random-access of a large number (thousands to millions) of unique compounds. Conventional approaches to compound libraries involve robotic systems that allow for storage of compounds in large user facilities. A few approaches to integrated compound storage have been developed in recent years. A recently published report [Linder et al., "Reagent-loaded cartridges for valveless and automated fluid delivery in microfluidic devices", Anal. Chem., vol. 77, pp. 64-71, 2005] presents storage of droplets with unique compounds in a serial fashion in a long micro-bore tube. Even though a large number of compounds can be stored in this fashion, the access to such a library if linear. This limits the usage of such a library since only a first-in first-out (FIFO) access scheme can be utilized.

Bubble logic facilitates creation of on-chip integrated compound libraries for storage of a large number of chemicals on chip. The compounds are stored in bubble logic memory, which can be accessed randomly. Thus, for a storage scheme in a matrix format, any compound in the array can be accessed at any given time. On-chip compound libraries are portable, and hence can be accessed at remote locations. Distribution of a large number of compounds in such a format also facilitates the development of an integrated solution for transport of diverse compounds, such as is required for any screening operation.

Single-Cell/Single Molecule Analysis Platform.

Mechanisms for generating individual drops and bubbles on demand have been previously described. With a low concentration of cells or molecules in solution, it is possible to encapsulate individual cells or molecules inside droplets and bubbles. This provides a platform to shuttle and manipulate these individual entities on a chip guiding them using bubble logic. This is superior when compared to manipulation of cells or molecules in bulk solution, since no on-chip electrical, mechanical, or optical probes are required to manipulate these small objects.

In one embodiment, the parts of the single cell/single molecule analysis system include a generator for producing droplets or bubbles with a single cell, molecule, or entity trapped inside the droplet/bubble, a sorter for removing unwanted or empty droplets, a bubble logic chip for performing a screening operation, detection/measurement units for specific properties, and a bubble logic storage unit for storing the selected samples at the required location.

A generalized methodology for the manipulation of small objects on-chip can thus be obtained with bubble logic, with no external parts. This provides the ability to analyze and post-process a large population of cells or molecules in an automated fashion. Objects can be stored in bubble logic memory at specified locations, trapped passively to perform measurements on the same, and moved off-chip for further analysis or developing a cell culture by numerous printing routines. Since the object under study is trapped inside a bubble/droplet, measurements and analysis can be performed on individual entities. It is expected that such an automated, high-throughput platform for analysis of large ensemble of cells/molecules has myriad applications in single-cell diagnostics and therapeutics.

The universal logic gates, toggle flip-flop, ripple counter, synchronizer, ring oscillator and electro-bubble modulator of the present invention exhibit nonlinearity, bistability, gain, synchronization, cascading, feedback, and signal encoding. Having shown the required properties of a scalable logic family, they can be used to create complex microfluidic circuits capable of performing arbitrary fluid process control and computation in an integrated fashion. This can reduce the size, cost, and complexity of current microfluidic platforms, and make possible the development of very large-scale microfluidic reactors for use in areas including combinatorial chemistry and drug discovery. Long-term measurements on droplets in segmented flow micro-reactors require a programmable bistable trap for holding drops for arbitrary periods of time. Toggle flip-flop gate presented here can be used as a passive, reusable trap for the same. Bubble synchronizer presented here can also be used to passively remove any skew in arrival timings of droplets at a junction, necessary for on-chip droplet coalescence. The ability to generate bubbles on demand provides a mechanism to encode information and thus program microfluidic bubble circuits. These bubble logic processors, where a bit of information can also carry a chemical payload, merge chemistry and computation.

In the microfluidic bubble logic circuits of the present invention, both information and materials may be processed. Since an information bit (bubble or a droplet) can also carry a payload inside (as dissolved molecules or substances), information processing happens hand in hand with materials processing (reactions). This provides a very powerful way to control chemical/biochemical reaction sequences on chip. Currently there is a lack of scalable control methodology for microfluidic circuits (both single phase or multiple phase droplet systems). The control and logic methodology of the present invention solves this problem by building logic devices that perform both logic operations and thus control in microfluidic geometries. Thus, the system can be scaled up to be orders of magnitude more complex than what is currently possible. This results in VLSI like integration in microfluidic systems. Since a logic family is used to perform both computation and material processing in a microfluidic system, it is possible to build abstract modules to perform various tasks. These modules can be defined by input and output sequences with the desired operation. Moreover, these modules can be cascaded together in serial or parallel manner to provide a complex scaled-up microfluidic circuit. For a designer building a microfluidic integrated circuit, a black box can be employed, so that the designer need not worry about the inner workings of the circuit. Providing these multiple levels of architecture abstraction therefore greatly enhances the possible complexity of microfluidic chips.

In the present invention, the challenges of implementing all-fluidic logic machinery at low Reynolds number and corresponding background are solved. The present invention has been employed to design and fabricate a family of bubble or droplet logic devices, storage elements, valves, counters, synchronizers, sensors, and actuators. Using the present invention, new physical mechanisms and devices that can operate down below the inertial regime from moderate to very low Reynolds numbers may be created. The benefits include the ability to shrink down the device length scales to the micron or nano-size regime. With integrated plumbing and current micro- and nanofluidic fabrication techniques, large-scale integration of proposed all-fluidic micron sized devices is possible. Micro-flow control is essential in variety of fields including chemistry, biomedicine, pharmaceuticals, drug-delivery, medical diagnostics and micro-instrumentation. The problems of scalable control, electric field interference, and the merging of silicon-based technology with PDMS-based soft lithography devices are solved by the all-fluid no-moving part control systems of the present invention. Due to nonlinearity, gain, bistability, synchronization, modulation and fan-out, cascading and integration is further possible to build complex control systems via designing fluidic circuits.

While a preferred embodiment is disclosed, many other implementations will occur to one of ordinary skill in the art and are all within the scope of the invention. Each of the various embodiments described above may be combined with other described embodiments in order to provide multiple features. Furthermore, while the foregoing describes a number of separate embodiments of the apparatus and method of the present invention, what has been described herein is merely illustrative of the application of the principles of the present invention. Other arrangements, methods, modifications, and substitutions by one of ordinary skill in the art are therefore also considered to be within the scope of the present invention, which is not to be limited except by the claims that follow.

What is claimed is:

1. A bubble synchronizer for a fluidic device, comprising:
   a non-linear ladder network, the non-linear ladder network comprising:
      at least two data-carrying channels; and
      at least one interconnecting channel, each interconnecting channel connecting at least two data-carrying channels and being thinner than the data-carrying channels, the data-carrying and interconnecting channels being configured so that the flow of gaseous or liquid bubbles disposed within an immiscible liquid within each data-carrying channel becomes synchronized with the flow of gaseous or liquid bubbles disposed within an immiscible liquid within the other data-carrying channels.

2. The bubble synchronizer of claim 1, wherein the non-linear ladder network, the data-carrying channels, and the interconnecting channels are configured so that the flow, through the channels, of the gaseous or liquid bubbles is controlled by at least one of the group selected from: a resistive or constrictive force caused by interaction between the disposed bubbles and the geometry of the channels or the ladder network, a resistive or constrictive force caused by interaction between the disposed bubbles and the configuration of the ladder network, and the interaction between disposed bubbles.

3. The bubble synchronizer of claim 1, further comprising:
   at least one channel input for accepting the immiscible liquid and disposed gaseous or liquid bubbles into the data-carrying channels; and
   at least one channel output for discharging at least some of the immiscible liquid and disposed gaseous or liquid bubbles from the data-carrying channels.

4. The bubble synchronizer of claim 1, further comprising a bubble generator.

5. The bubble synchronizer of claim 1, further comprising an on-demand bubble annihilator.

6. The bubble synchronizer of claim 1, wherein the synchronizer is cascaded with at least a second fluidic logic device.

7. A timing restoration fluidic device, comprising:
   a non-linear ladder network, the non-linear ladder network comprising:
      at least two data-carrying channels; and
      at least one interconnecting channel, each interconnecting channel connecting at least two data-carrying channels and being thinner than the data-carrying channels, the data-carrying and interconnecting channels being configured so that the flow of gaseous or liquid bubbles disposed within an immiscible liquid within each data-carrying channel becomes synchronized with the flow of gaseous or liquid bubbles disposed within an immiscible liquid within the other data-carrying channels;
   at least one channel input for accepting the immiscible liquid and disposed gaseous or liquid bubbles into the data-carrying channels; and
   at least one channel output for discharging at least some of the immiscible liquid and disposed gaseous or liquid bubbles from the data-carrying channels.

8. The timing restoration fluidic device of claim 7, wherein the non-linear ladder network, the data-carrying channels, and the interconnecting channels are configured so that the flow, through the channels, of the gaseous or liquid bubbles is controlled by at least one of the group selected from: a resistive or constrictive force caused by interaction between the disposed bubbles and the geometry of the channels or the ladder network, a resistive or constrictive force caused by interaction between the disposed bubbles and the configuration of the ladder network, and the interaction between disposed bubbles.

9. The timing restoration fluidic device of claim 7, further comprising a bubble generator.

10. The timing restoration fluidic device of claim 7, further comprising an on-demand bubble annihilator.

11. The timing restoration fluidic device of claim 7, wherein the timing restoration fluidic device is cascaded with at least a second fluidic logic device.

12. The timing restoration fluidic device of claim 7, wherein at least some of the bubbles contain a cell or molecule.

13. The timing restoration fluidic device of claim 12, further comprising a generator configured to encapsulate the cells or molecules in the bubbles.

14. A method for timing restoration in a fluidic device, the method comprising:
- accepting a flow of gaseous or liquid bubbles disposed within an immiscible liquid into a non-linear ladder network, the non-linear ladder network comprising:
  - at least two data-carrying channels; and
  - at least one interconnecting channel, each interconnecting channel connecting at least two data-carrying channels and being thinner than the data-carrying channels, the data-carrying and interconnecting channels being configured so that the flow of gaseous or liquid bubbles disposed within an immiscible liquid within each data-carrying channel becomes synchronized with the flow of gaseous or liquid bubbles disposed within an immiscible liquid within the other data-carrying channels; and
- discharging at least some of the immiscible liquid and synchronized disposed gaseous or liquid bubbles from the data-carrying channels.

15. The method of claim 14, wherein the non-linear ladder network, the data-carrying channels, and the interconnecting channels are configured so that the flow, through the channels, of the gaseous or liquid bubbles is controlled by at least one of the group selected from: a resistive or constrictive force caused by interaction between the disposed bubbles and the geometry of the channels or the ladder network, a resistive or constrictive force caused by interaction between the disposed bubbles and the configuration of the ladder network, and the interaction between disposed bubbles.

16. The method of claim 14, further comprising the step of generating the disposed bubbles for flowing into the non-linear ladder network.

17. The method of claim 14, the step of generating further comprising the step of controlling the disposal of the bubbles in the liquid using a modulator.

18. The method of claim 14, further comprising the step of receiving the bubbles in liquid into a bubble trap as the bubbles are discharged from the data-carrying channels.

19. The method of claim 14, further comprising the step of cascading the non-linear ladder network with at least a second fluidic logic device.

20. The method of claim 14, further comprising the step of annihilating at least some of the bubbles using a bubble annihilator.

* * * * *